US008920559B2

(12) United States Patent
Childs et al.

(10) Patent No.: US 8,920,559 B2
(45) Date of Patent: *Dec. 30, 2014

(54) SCREENING FOR SOLID FORMS BY ULTRASOUND CRYSTALLIZATION AND COCRYSTALLIZATION USING ULTRASOUND

(75) Inventors: Scott L. Childs, Atlanta, GA (US); Patricia M. Mougin-Andres, West Lafayette, IN (US); Barbara C. Stahly, West Lafayette, IN (US)

(73) Assignee: Aptuit (West Lafayette), LLC, West Lafayette, IN (US)

( * ) Notice: Subject to any disclaimer, the term of this patent is extended or adjusted under 35 U.S.C. 154(b) by 1102 days.

This patent is subject to a terminal disclaimer.

(21) Appl. No.: 12/888,052

(22) Filed: Sep. 22, 2010

(65) Prior Publication Data

US 2011/0251426 A1 Oct. 13, 2011

Related U.S. Application Data

(63) Continuation of application No. 10/592,591, filed as application No. PCT/US2005/008746 on Mar. 14, 2005, now abandoned.

(60) Provisional application No. 60/552,479, filed on Mar. 12, 2004, provisional application No. 60/571,248, filed on May 14, 2004.

(51) Int. Cl.
| | |
|---|---|
| *C30B 7/14* | (2006.01) |
| *B01D 9/00* | (2006.01) |
| *C30B 7/00* | (2006.01) |
| *C07C 217/72* | (2006.01) |

(52) U.S. Cl.
CPC .............. *B01D 9/00* (2013.01); *B01D 9/0077* (2013.01); *C30B 7/00* (2013.01); *C07C 217/72* (2013.01)
USPC .................................. 117/68; 117/69; 117/70

(58) Field of Classification Search
USPC ................................................ 117/68, 69, 70
See application file for complete search history.

(56) References Cited

U.S. PATENT DOCUMENTS

| 2,665,277 A | 1/1954 | Homeyer et al. |
| 4,379,177 A | 4/1983 | McCoy et al. |

(Continued)

FOREIGN PATENT DOCUMENTS

| JP | 01-308284 | 12/1989 |
| JP | 2005-535602 | 11/2005 |

(Continued)

OTHER PUBLICATIONS

International Search Report corresponding to International Application Serial No. PCT/US2005/08746, mailed Jul. 7, 2008, 4 pages.

(Continued)

*Primary Examiner* — Bob M Kunemund
(74) *Attorney, Agent, or Firm* — J.A. Lindeman & Co., PLLC

(57) ABSTRACT

The present disclosure relates to crystallizing a chemical substance(s) using ultrasound. Methods are provided for screening a chemical substance according to its solid forms by using ultrasound to generate new or unusual solid forms. Methods are also provided for crystallizing a chemical substance by novel techniques that include sonication. The present disclosure also relates to cocrystallization using ultrasound. Methods are provided for preparing cocrystals of an active agent and a guest by sonicating and crystallizing. Methods are also provided for screening a sample according to solid state phases (such as cocrystals and salts) and include generating a cocrystal from the sample using ultrasound.

5 Claims, 10 Drawing Sheets

(56) References Cited

U.S. PATENT DOCUMENTS

| | | | |
|---|---|---|---|
| 4,943,632 A | 7/1990 | Robinson | |
| 5,080,832 A | 1/1992 | Etter et al. | |
| 5,847,214 A | 12/1998 | Arosio et al. | |
| 6,931,950 B2 | 8/2005 | Malachowski et al. | |
| 7,452,555 B2* | 11/2008 | Childs | 424/666 |
| 8,212,079 B2* | 7/2012 | Childs | 564/347 |
| 8,350,085 B2* | 1/2013 | Childs | 564/347 |
| 2002/0048610 A1 | 4/2002 | Cima et al. | |
| 2003/0224006 A1 | 12/2003 | Zaworotko et al. | |
| 2004/0176335 A1 | 9/2004 | Childs | |
| 2005/0186285 A1 | 8/2005 | Ray et al. | |
| 2009/0281195 A1 | 11/2009 | Childs | |
| 2011/0257430 A1 | 10/2011 | Childs | |

FOREIGN PATENT DOCUMENTS

| | | |
|---|---|---|
| WO | WO 01/92293 A2 | 12/2001 |
| WO | WO 03/101392 | 12/2003 |
| WO | WO 2004/078161 | 9/2004 |

OTHER PUBLICATIONS

Written Opinion of the International Searching Authority corresponding to International Application Serial No. PCT/US2005/08746, mailed Jul. 7, 2008, 8 pages.
Ratsimba et al., "Sonocrystallization. The End of Empiricism? A review on the fundamental investigations and the industrial developments," Kona 17:38-48 (1999).
McCausland et al., "Use the power of sonocrystallization for improved properties" Chem. Engin. Progress 97(7):56-61 (2001).
McCausland et al., "Sonocrystallization—ultrasonically promoted crystallization for the optimal isolation of drug actives," Drug Delivery Systems & Sciences-accentus.co.uk, http://www.accentus.co.uk/articles/c3_ddss_article/pdf 2002.
Ueno et al., "In Situ Studies of Ultrasound-Stimulated Fat Crystallization Using Synchrotron Radiation," J. Phys. Chem. B 107:4927-4935 (2003).
Li et al., "Rapid sonocrystallization in the salting-out process," J. Cryst. Growth 247:192-198 (2003).
U.S. Appl. No. 60/360,768, "Multiple Component Crystalline Phases Containing a Pharmaceutical Component," filed Mar. 1, 2002.
Office Action of Canadian Intellectual Property Office for Application No. 2,514,092 dated Jan. 4, 2011.
A. J. C. Wilson (ed), International Tables for X-ray Crystallography, vol. C. Kynoch, Academic Publishers, Dordrecht, 1992, Tables 6.1.1..4 (pp. 500-502) and 4.2.6.8 (pp. 219-222).
Etter, Margaret C., and Daniel A. Adsmond (1990) "The use of cocrystallization as a method of studying hydrogen bond preferences of 2-aminopyridine," J. Chem. Soc., Chem. Commun. 1990 589-591.
Etter, Margaret C., John C. MacDonald, and Joel Bernstein (1990a) "Graph-set analysis of hydrogen-bond patterns in organic crystals," Acta Crystallogr., Sect. B, Struct. Sci., vol. 846; 256-262.
Etter, Margaret C., Zofia Urbanczyk-Lipkowska, Mohammad Zia-Ebrahimi, and Thomas W. Panunto (1990b) "Hydrogen bond directed cocrystallization and molecular recognition properties of diarylureas," J. Am. Chem. Soc. vol. 112, 8415-8426.
Scott L. Childs, "Non bonded Interactions in Molecular Crystal Structures," Emory Univ., USA, available from UMI, Order No. DA3009424 (288 pp.); Dissertation Abstract—Int. Ref. B2001; 62(3); 1394.
International Search Report and Written Opinion, dated Jul. 18, 2005; from International Application No. PCT/US04/01699.
Gavezzotti Acc. Chem. Res. 1994, 27, 309-314.
Aakeroy, C. B, Acta Crystallogr. Sect. B—Struct. Sci. 1997, 53, 569-586.
Aakeroy, C. B.; Evans; T. A; Seddon, K. R, Palinko, 1. New J. Chem. 1999, 23, 145-152.
Aullon, G.; Bellamy, D.; Brammer, L.; Bruton, E. A; Orpen, A G. Chem. Commun. 1998, 653-654.

Bartoszak-Adamska, E.; Wojciechowski, G.; Jaskoiski, M.; Brzezinski, M,; *Journal of Molecular Structure* 595 (2001) 21-28.
Bettinetti, G.; Caira, M. R; Callegari, A; Medi, M.; Sorrenti, M.; Tadini, C. J. Pharm Sci. 2000, 89, 478-489.
Bettis, J. W.; Lach, J. L.; Hood, J. *American Journal of Hospital Pharmacy* 1973, 30; 240-243.
Bilton, c.; Allen, F H.; Shields, G. P.; Howard, J. A K. *Acta Crystallogr. Sect. 8—Struct. Sci.* 2000, 56, 849-856.
Braga, D.; Cojazzi, G.; Abati, A; Maini, L.; Polito M.: Scaccianoce, L.; Grepioni, F J. *Chem. Soc.-Dalton Trans.* 2000, 3969-3975.
Braga, D.; Draper S. M.; Champeil E.; Grepioni, F; *Journal of Organometallic Chemistry* 573 (1999) 73-77.
Braga, D.; Maini, L.; Polito, M.; Grepioni, F *Chem. Commun.* 2002, 2302-2303.
Cheung, E. Y. et al, J. Am. Chem. Soc., 2003, 125; 14658-59.
Cheung, E. et al. "Direct Structure Determination of a Multicomponent Molecular Crystal Prepared by a Solid-State Grinding Procedure," J. Am. Chem. Soc. XXXX, XXX (2003).
Coe, S.; Kane J. J.; Nguyen, T. L.; Toledo, L. M.; Wininger, E.; Fowler, F W.; Lauher, J. W. *J. Am. Chem. Soc.* 1997, 119, 86-93.
Daihus, B.; Gorbitz, C. H. *Acta Crystallogr. Sect. C—Cryst. Struct. Commun.* 1999, 55, 1547-1555.
Datta, S.; Grant D. J. W.; *Nature* Jan. 2004. vol. 3, 42-57.
Dega-Szafran, Z.; Katrusiak, A; Szafran, M., *J. Mol. Struct.* 2001, 570, 165-174.
Deng, J. et al.; Tetrahedron: *Asymmetry* 11 (2000) 1729-1732.
Desiraju, G. R, The Royal Society of Chemistry, 2003, 466-467.
Dunitz; J.D.; *The Royal Society of Chemistry* 2003, 506.
Edwards, M.R; Jones, W.; Motherwell, W.D.S., *Cryst. Eng.* 2002, 5, 25-36.
Fleischman, S.G.; Kuduva, S.S.; McMahon, J. A; Moulton, B.; Walsh, R.D.B.; Rodriguez-Hornedo, N.; Zaworotko, M.; *J. Cryst. Growth Des.* 2003, 3, 909-919.
Goldberg, I., *J. Am. Chem. Soc.* 1982, 104, 7077-7084.
Gorbitz, CH.; Hersieth, H. P *Acta Crystallogr. Sect. B—Struct Sci.*, 2000, 56; 526-534.
Gorbitz, CH., *Acta Crystallogr Sect. Cryst. Struct. Commun.*, 2000, 56, 500-502.
Hu, Z-Q et al., *Acta Cryst.*, (2002) C58, o612-o614.
Hubschle C B. et al., *Acta Cryst.*, (2002) C58 o540-o542.
Iimura, N.; Ohashi, Y.; Hirata, H. *Bull. Chem. Soc. Jpn.* 2000, 73, 1097-1103.
Karlsson, R, *Acta Cryst.*, (1972) B28, 2358.
Kumar, V.S.S.; Nangia, A; Katz, A.K.; Carrell, H.L. *Cryst. Growth Des.* 2002, 2, 313-318.
Kuroda, R; Imai, Y.; Tajima, N. *Chem. Commun.* 2002, 2848-2849.
Morgan, T.K. et al.; 1986 American Chemical Society, 1398-1405.
Nangia, A; Desiraju, G.R, *Acta Crystallogr. Sect. A*, 1998, 54, 934-944.
O'Dowd, c.; Kennedy, J.D.; Thornton-Pett, M.J., *Organomet. Chem.*, 2002, 657, 20-39.
Orita, A; Jiang, L.S.; Nakano, T.; Ma, N.C; Otera, *J.Chem. Commun.* 2002, 1362-1363.
Oswald, L.D.H.; Alan D.R.; McGregor, P.; Motherwell, W.D.S.; Parsons, S.; Pulham, C.R., *Acta Crystallogr. Sect. B—Struct. Sci*, 2002, 58, 1057-1066.
Pierpont, C.G.; Lanai, S.A., *Acta Crystallogr. Sect. C—Cryst. Struct. Commun.* 1986,42, 1085-1087.
Rai, U. S.; George, S., *Thermochim. Acta* 1994, 243, 17-25.
Reddy, L.S.; Nangia, A; Lynch; V.M., *Crystal Growth & Design*, "Phenyl-Perfluorophenyl Synthon Mediated Cocrystallization of Carboxylic Acids and Amides," XXXX vol. 0, No. 0, 1-6, 2003.
Remenar, J. F et al., *Organic Process Research & Development* 2003, 7, 990-996.
Remenar, J. F; Morissette, S.L.; Peterson, M. L.; Moulton, B.;: MacPhee J.M.; Guzman, H. R.; Almarsson, 0., J. *Am.Chem. Soc.*, 2003, 125, 8456-8457.
Rothenberg; G.; Downie; A. P.; Raskin, C. L.; Scott, J. L. *J. Am. Chem. Soc.* 2001, 123, 8701-8708.
Schauer, C.L. et al., J. *Chem. Soc.*, 1997, 119, 10245-10246.
Shan, N.; Toda, F; Jones, W. *Chem. Commun.* 2002, 2372-2373.
Steiner, T. *Acta Crystallogr. Sect B—Struct. Sci.*, 1998, 54, 456-463.
Steiner, T.; *New J. Chem.* 1998, 22, 1099-1103.

(56) References Cited

OTHER PUBLICATIONS

Thallapally, P. K.; Nangia; A *Crystengcomm* 2001, art. No. 27.
TransForm Pharmaceuticals, Inc. Press Release, Lexington, MA, Nov. 3, 2003.
Videnova-Adrabinska, V. *Acta Cryst.*, 1996, B52, 1048-1056.
Vishweshwar, P.; Nangia, A. Lynch; V. M., *Cryst. Gmwth Des.* 2003, 3, 783-790.
Vishweshwar, P., Nangia; A; Lynch, V. M., *Crystengcomm* 2003 164-168.
Walsh R.D.B.; Bradner, M.W.; Fleischman, S.; Morales, L. A; Moulton, B.; Rodriguez-Homedo, N.; Zaworotko, M.J., *J. Chem. Common.* 2003, 186-187.
Wang, K.W.; Pan, Y.J.; Jin, A.M. Z. *Krist.—New Cryst. Struct.* 2002, 217, 435-436.
Feb. 28, 2012, Office Action in U.S. Appl. No. 13/170,701.
Oct. 17, 2011, Office Action in U.S. Appl. No. 12/234,093.
Sep. 13, 2007, Office Action in U.S. Appl. No. 7,452,555.
Feb. 7, 2007, Office Action in U.S. Appl. No. 7,452,555.

* cited by examiner

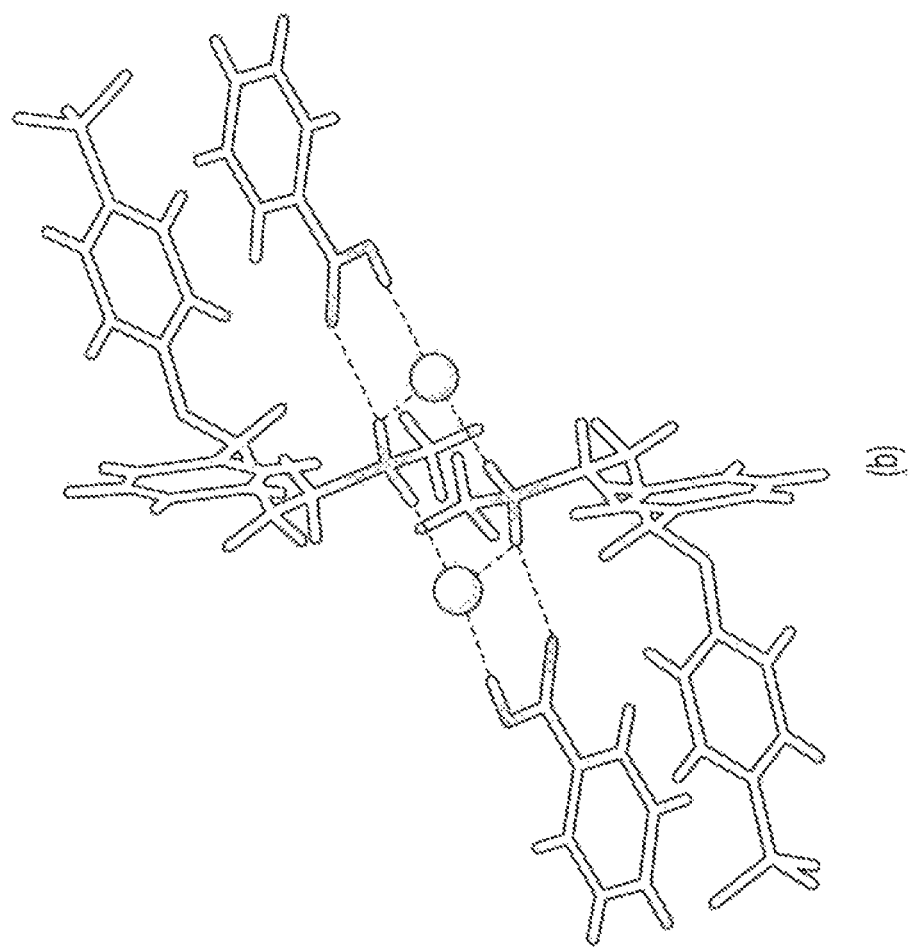
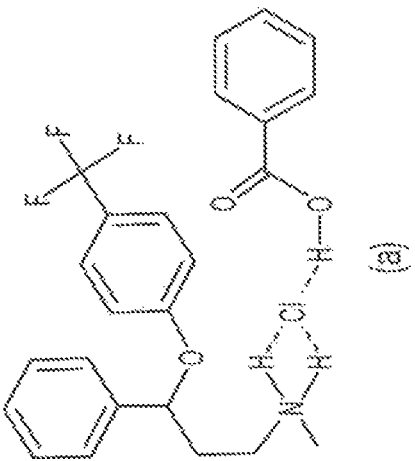
FIG. 9

SCREENING FOR SOLID FORMS BY ULTRASOUND CRYSTALLIZATION AND COCRYSTALLIZATION USING ULTRASOUND

CROSS-REFERENCE TO RELATED APPLICATIONS

This application is a continuation application of U.S. patent application Ser. No. 10/592,591 filed Jul. 25, 2007, which is the national stage of International Application No. PCT/US2005/008746, filed Mar. 14, 2005, which claims priority of U.S. Provisional Patent Application No. 60/552,479, filed Mar. 12, 2004; and U.S. Provisional Patent Application No. 60/571,248, filed May 14, 2004. All of these references are incorporated herein by reference.

FIELD OF THE INVENTION

The present disclosure relates to crystallizing a chemical substance using ultrasound. Methods are provided for screening a chemical substance according to its solid forms by using ultrasound to generate new or unusual solid forms. Methods are also provided for crystallizing a chemical substance by novel techniques that include sonication. The present disclosure also relates to cocrystallization using ultrasound. Methods are provided for preparing cocrystals of an active agent and a guest by sonicating and crystallizing. Methods are also provided for screening a sample according to solid state phases (such as cocrystals and salts) and include generating a cocrystal from the sample using ultrasound.

Chemical substances (compounds, elements, and mixtures) have properties which tend to be unpredictable and variable. Certain chemical substances may have utility for numerous different applications, including vital biological applications, yet a slight change may reduce or eliminate the utility or beneficial purpose. Similarly, certain chemical processes may have better or worse performance based upon minor differences.

An active agent may be provided in a variety of solid state phases. For example, it may be provided as a crystal of the pure compound. Alternatively, the active agent may be provided as a salt. Alternatively, the active agent may be provided as a cocrystal with another compound.

Cocrystals are crystals that contain two or more non-identical components (for example, two non-identical molecules). The properties of cocrystals may be the same or different than the properties of the individual components or mixtures of crystals of the individual components. Examples of cocrystals may be found in the Cambridge Structural Database. Examples of cocrystals may also be found at Etter et al., "The use of cocrystallization as a method of studying hydrogen bond preferences of 2-aminopyridine," *J. Chem. Soc., Chem. Commun.* 589-591 (1990); Etter, et al., "Graph-set analysis of hydrogen-bond patterns in organic crystals," *Acta Crystallogr., Sect. B, Struct. Sci.* B46 256-262 (1990); Etter, et al., "Hydrogen bond directed cocrystallization and molecular recognition properties of diarylureas," *J. Am. Chem. Soc.* 112 8415-8426 (1990); which are incorporated herein by reference in their entireties. The following articles are also incorporated herein by reference in their entireties: Görbotz, et al., "On the inclusion of solvent molecules in the crystal structures of organic compounds," *Acta Cryst.* B56 625-534 (2000); and Kumar, et al., "Molecular Complexes of Some Mono- and Dicarboxylic Acids with trans-1,4-Dithiane-1,4-dioxide," American Chemical Society, Crystal Growth & Design, Vol. 2, No. 4 (2002). Additional information and details regarding cocrystallization may be found in U.S. application Ser. No. 10/763,987, "Novel Cocrystallization," filed Jan. 21, 2004, which is incorporated by reference herein.

A salt is a compound formed when the hydrogen of an acid is replaced by a metal or its equivalent (e.g., an $NH_4^+$ radical). Hawley's Condensed Chemical Dictionary, p. 977 ($14^{th}$ Ed. 2001). In a salt one or more ionic bonds are formed. In a cocrystal, two or more compounds retain their own chemical identities, and no new ionic or covalent bonds are formed, although hydrogen bonds or other interactions may hold different compounds to each other.

The identification of a desirable solid state phase for an active agent is important in the pharmaceutical field, as well as in other fields including nutraceuticals, agricultural chemicals, dyes, explosives, polymer additives, lubricant additives, photographic chemicals, and structural and electronic materials.

In particular, the pharmaceutical industry spends a great deal of time, effort and expense on the identification of particular compounds, mixtures and formulations that will have beneficial effect. Research is done as to whether such compounds, mixtures and formulations will be safe and effective. Slight differences in chemical composition or structure may yield significant differences in biological activity. Thus, researchers frequently test many different compounds, mixtures and formulations for biological activity and other effects as well as testing different processes and conditions for the preparation of such chemical compounds and mixtures.

The process of thorough analysis of different chemical compounds, mixtures, formulations, processes, or structures is commonly referred to as screening. Screening is partially a function of time and effort, with the quality or results of screening being related to the number of samples prepared and/or analyzed as well as the quality of preparation and/or analysis underlying those samples. To that end, it is frequently an objective with screening processes to increase the number of samples and decrease the amount of each sample used for analysis. Screening plays a vital role in the pharmaceutical field, as the most advantageous compound, mixture or formulation is frequently found through successful screening processes.

In some screening processes, variations are introduced in order to see the result(s), if any, of such variations, or to confirm that variations do not lead to substantially different results. Generally, at least two samples of a screened chemical substance (in other words, a compound, element, or mixture that is the subject of the screening process) are subjected to differing parameters, and one or more properties of the samples are determined to see whether the differing parameters caused different results.

Processes have been used for screening chemical compounds according to their solid form. When a compound has different solid forms, the different forms are frequently referred to as polymorphs of that compound. A polymorphic compound as used herein means a compound having more than one solid form. For example, a polymorphic compound may have different forms of its crystalline structure, or it may exist as different hydrates or solvates.

The solid form of a chemical substance may have an impact on biological activity. The same chemical compound may exhibit different properties depending upon whether it is in an amorphous, crystalline or semisolid state. A semisolid as used herein indicates materials like waxes, gels, creams, and ointments. Furthermore, a chemical compound may exist in different solid forms within the different states, and those different solid forms may also exhibit different properties. For example, there may be several different crystalline solid forms of a substance, the different crystalline solid forms having different properties. As another example, a substance may have different amorphous forms, the amorphous forms having different properties. As a result, different solid forms, including different crystalline forms, of a chemical compound may have greater or lesser efficacy for a particular application. The identification of an optimal solid form, or other possible solid forms, is important in the pharmaceutical field, as well as in other fields including nutraceuticals, agricultural chemicals, dyes, explosives, polymer additives, lubricant additives, photographic chemicals, and structural and electronic materials.

It is desirable in the pharmaceutical field as well as other fields to find the solid form of a chemical substance that exhibits desired physical and chemical properties. One form may be more stable or have other properties that make it preferable over other forms. One form of a chemical composition may have better bioavailability, solubility, or absorption characteristics or in other ways be more suitable for delivery of therapeutic doses than other forms. It is frequently desirable within a screening process to generate, or at least search for, all or most of the possible solid forms of a compound. Past attempts to generate a variety of solid forms included flash evaporations, cooling under different conditions and/or the addition of seeds of solid material. However, some materials strongly resist the generation of some of their possible solid forms.

It is desirable in many fields to find a solid state phase of an active agent that exhibits desired physical and chemical properties. One solid state phase may be more stable or have other properties that make it preferable over other solid state phases. One solid state phase may have better bioavailability, solubility, or absorption characteristics or in other ways be more suitable for delivery of therapeutic doses than other forms. It is frequently desirable within a screening process to generate, or at least search for, all or most of the possible solid state phases of a compound.

One or more solid forms may be generated by crystallization of a sample. One or more solid state phases may be generated by cocrystallization of a chemical substance with different guest molecule(s).

Among the phenomena in crystallization are nucleation and growth. Crystal nucleation is the formation of an ordered solid phase from liquids, supersaturated solutions, saturated vapors, or amorphous phases. Growth is the enlargement of crystals caused by deposition of molecules on an existing surface.

Nucleation may be induced by the presence of "seed" crystals. Some solid particle is present to provide a catalytic effect and reduce the energy barrier to formation of a new phase. Crystals may originate on a minute trace of a foreign substance (either impurities or container walls) acting as a nucleation site. Nucleation may also be promoted by external or nonchemical means, such as stirring the crystallization environment, or by applying ultrasound to the crystallization environment.

As mentioned above, ultrasound has been applied to promote nucleation. For example, U.S. Pat. No. 6,630,185 discusses a process for the crystallization of a solid phase from a liquid, characterized in that the liquid during crystallization is subjected to ultrasound in the absence of transient cavitation. According to this patent, it has been known since 1927 that exposing supercooled melts or supersaturated solutions of various substances to ultrasound has an influence on the nucleation and/or the growth of crystals. The effect is referred to as sonocrystallisation. A particular aspect of sonocrystallisation is sononucleation. It deals with the initiation of crystal formation, has been studied extensively with sugar and is applied since the late 1950's. Sonocrystallisation of supercooled water, supercooled metal melts and supersaturated solutions of various inorganic materials are said to have received a lot of attention.

U.S. Patent Application Publication No. 20030051659 A1 discusses a process for crystallizing small particles with a narrow particle size distribution. The crystals are obtained by introducing ultrasound into a solution or suspension of the substance to be crystallized while simultaneously adjusting a specific stirring power. U.S. Patent Application Publication No. 20030166726 A1 discusses a method for reducing the particle size of amino acid crystals using ultrasound.

U.S. Patent Application Publication No. 20020054892 A1 discusses a method of inducing solidification in a fluid composition comprising a cosmetic active, a crystalline organic structurant and a carrier. The method comprises exposing the fluid composition to ultrasound or converting the composition to a soft solid.

U.S. Pat. No. 5,830,418 discusses a method of using ultrasound to promote crystallization of solid substances contained in a flowable material. A flowable material, such as a supercooled melt or supersaturated solution, is dispensed onto a take-up member such as a belt or drum. Either prior to, or after being dispensed onto the take-up member, the material is exposed to ultrasound to promote the crystallization of solid substances in the material.

None of the foregoing references discloses the use of ultrasound as a variable parameter in a screening method to identify the various solid forms of a chemical substance.

There is a continued need to improve screening methods that identify all or a high percentage of possible forms of a chemical substance. There is also a need for improved methods of selectively generating the desired form of a chemical substance.

There is a continued need to improve screening methods that identify all or a high percentage of possible solid state phases of a chemical substance. There is also a need for improved methods of selectively generating solid state phases, including cocrystals, of a chemical substance.

SUMMARY OF THE INVENTION

As one aspect, a method is provided for screening a chemical substance for possible solid forms. The method comprises the steps of providing a chemical substance in a plurality of samples, sonicating at least one of the samples, and solidifying the chemical substance from the samples. The samples will usually be provided as a solution, suspension, melt, or other mixture of the chemical substance in one or more solvents. The screening method may comprise providing a first sample of the chemical substance in a first solvent, and a second sample of the chemical substance in a second solvent. The method may also comprise determining whether one or more solid forms of the chemical substance were generated.

As another aspect, a method is provided for crystallizing a chemical substance. This method is beneficial for searching for and/or generating new or unusual solid forms of a chemical substance. The method comprises forming an emulsion comprising two or more substantially immiscible solvents and the chemical substance by applying ultrasound to a mixture of said solvents and the chemical substance. The chemical substance is in solution in one or both of the solvents. The method also comprises crystallizing the chemical substance from the emulsion.

As yet another aspect, a method of crystallizing a chemical substance is provided. The method comprising the steps of providing a sample of the chemical substance in a solvent, sonicating the solution or suspension at a predetermined supersaturation level, and crystallizing the chemical substance from the sample.

As another aspect, a method is provided for generating the most stable form of a chemical substance. The method comprises the steps of providing a sample of the chemical substance in a solvent, sonicating the sample at a predetermined supersaturation level, and crystallizing the chemical substance from the sample, and the crystallized chemical substance is the most stable solid form of the chemical substance relative to known solid forms of the chemical substance.

As a further aspect, a method is provided for generating a solid form of a chemical substance from a metastable solution (a solution in which the chemical substance remains in solution indefinitely or for relatively long periods). The method comprises forming a metastable solution of the chemical substance in a solvent, sonicating the metastable solution, and crystallizing the chemical substance from the solution.

As yet another aspect, a method is provided for obtaining a substantially pure solid form of a chemical substance. A substantially pure solid form of a chemical substance is a solid that is exclusively or almost exclusively of one solid form or has little or no other solid forms present. The method comprises the steps of providing a sample of the chemical substance in a solvent, sonicating the sample at a predetermined supersaturation level, and crystallizing the chemical substance from the sample, wherein a substantially pure solid form of the chemical substance is crystallized.

As another aspect, a method is provided for preparing a solvate of a chemical substance. The method comprises the steps of providing a sample comprising the chemical substance and a solvent, sonicating the sample, and generating a solid from the sample, wherein the solid comprises a solvate of the chemical substance and the solvent.

In the present methods, the solidifying step and the sonicating step may at least partially overlap. In some embodiments, the solidifying step and the sonicating step may overlap completely or almost completely. For example, where the solidifying step comprises evaporating a solvent from the samples, the method can comprise sonicating at least one of the samples until the solvent is substantially completely evaporated. Alternatively, the solidifying step can comprise at least partially evaporating the solvent from at least one of the samples before sonicating the sample.

In the present methods, a solvent can be evaporated (to a greater or lesser extent) from at least one of the samples before, during, or after the sonicating step. The present methods may comprise the step of cooling at least one of the samples before, during or after the sonicating step. The present methods may comprise the step of crash-cooling at least one of the samples before, during or after the sonicating step. The present methods may comprise a mixture of those actions, for example, the samples may be cooled followed by sonication and evaporation of the solvent.

The sample(s) can be sonicated by sonicating at least once or more than once. In some embodiments, the samples will be sonicated by ultrasound pulses. For example, one or more samples can be sonicated by at least one ultrasound pulse, or by at least 5 ultrasound pulses, or by any number of periodic ultrasound pulses. In some embodiments, the samples will be sonicated for a period of time. For example, one or more samples may be sonicated for about 5 to about 40 seconds, for at least about 5 minutes, or for another suitable time period.

In the present methods, one or more samples may be sonicated at least once during the solidification step. In some embodiments, sonication will be substantially continuous during the solidification step; in other embodiments, sonication will be periodic during the solidification step.

The present methods may also be employed to generate solid solvates and solid hydrates of the chemical substance.

In the present methods, a predetermined supersaturation level of the chemical substance in a solvent may be selected at which to begin sonication. For example, the predetermined supersaturation level may be selected to generate a relatively stable form of the chemical substance, or the most stable form of the chemical substance, as determined by comparison of the known solid forms of the chemical substance. The predetermined supersaturation level can be selected to generate a solvate of the chemical substance.

The present methods may comprise adding an antisolvent to a solution, suspension, emulsion, slurry or other composition of matter.

The present methods increase the likelihood of generating all or a high percentage of possible solid forms of a chemical substance.

As another aspect of the present invention, a method is provided for screening for possible cocrystals comprising an active agent. The method comprises the steps of providing a plurality of samples that contain the active agent. Each sample also contains at least one guest. It is contemplated that the samples may contain the same guest or a different guest. In a screening method, the samples will usually contain several different guests being used to evaluate different cocrystals (different solid state phases). The samples are sonicated, and the active agent and the guest are crystallized from the samples. The method comprises determining whether a cocrystal was generated in one or more of the samples. The method can also comprise analyzing the crystallized samples to determine one or more properties.

As another aspect, a method is provided for preparing a cocrystal comprising an active agent and a guest. The method comprises providing a sample of an active agent and a guest. The sample is sonicated, and a cocrystal of the active agent and the guest is crystallized from the sample.

As yet another aspect, a method is provided for screening for possible solid state phases, including salts, of an ionizable active agent and a counterion and optionally a guest. The method comprises providing an ionizable active agent and a counterion in a plurality of samples. An ionizable agent is an agent that can be ionized or has already been ionized; an ionizable agent is one that can be used to forming an ionic bond with a counterion. The samples are sonicated, and the ionizable active agent and the counterion form a salt and crystallize from the samples. The method further comprises determining whether a salt was generated in one or more of the samples.

As yet another aspect, a method is provided for screening for possible salts comprising an ionizable active agent. The method comprises providing a plurality of samples comprising an ionizable active agent and one or more counterions. The samples are sonicated, and one or more crystallized salt compounds are formed from the samples. The crystallized salt compounds comprise the ionizable active agent and the counterions. The plurality of samples may contain the same or different counterions. For example, at least one sample may contain a different counterion than at least one other sample. As another example, the plurality of samples can comprise a plurality of sets, where the sets differ in having different counterions, and the samples within each set have the same counterion.

The present techniques may be utilized in methods for screening an ionizable active agent according to its possible solid state phases, including cocrystals and/or salts. Such methods can comprise providing an ionizable active agent and one or more counterions in a plurality of samples, sonicating the sample(s), and forming a crystallized salt compound comprising the active agent and counterion. Suitable counterions include but are not limited to the cations or anions set forth in the present disclosure. Using the present techniques provides a greater likelihood of generating possible salts of the ionizable active agent. Moreover, a salt developed by such a method may be employed in connection with the methods described herein which relate to cocrystals comprising a salt and a guest.

As yet another aspect, a method is provided for cocrystallizing two or more components, such as an active agent and a guest. The method comprises determining a concentration for two or more components in a sample effective for cocrystallization of the components. A sample is prepared which comprise the components, in an effective volume and an effective concentration. The sample is sonicated and a cocrystal is generated from the sample. The cocrystal comprises the components.

The present methods may be used to form at least one new solid state phase of an active agent, including new solid state phases of active pharmaceutical ingredients. This can provide substantial benefits to the pharmaceutical industry and the public at large.

In the foregoing methods, the sonicating step and the crystallizing step will usually overlap at least partially. The samples may become supersaturated with respect to at least one of the active agent and the guest before, during or after the sonicating step. In the present methods, each of the samples may comprise more than one solvent, more than one active agent, and/or more than one guest.

BRIEF DESCRIPTION OF THE FIGURES

FIGS. 9 (a) and (b) are drawings of two-dimensional and three-dimensional models of a cocrystal of fluoxetine HCl and benzoic acid (1:1).

DETAILED DESCRIPTION OF PREFERRED EMBODIMENTS

Figure 1:
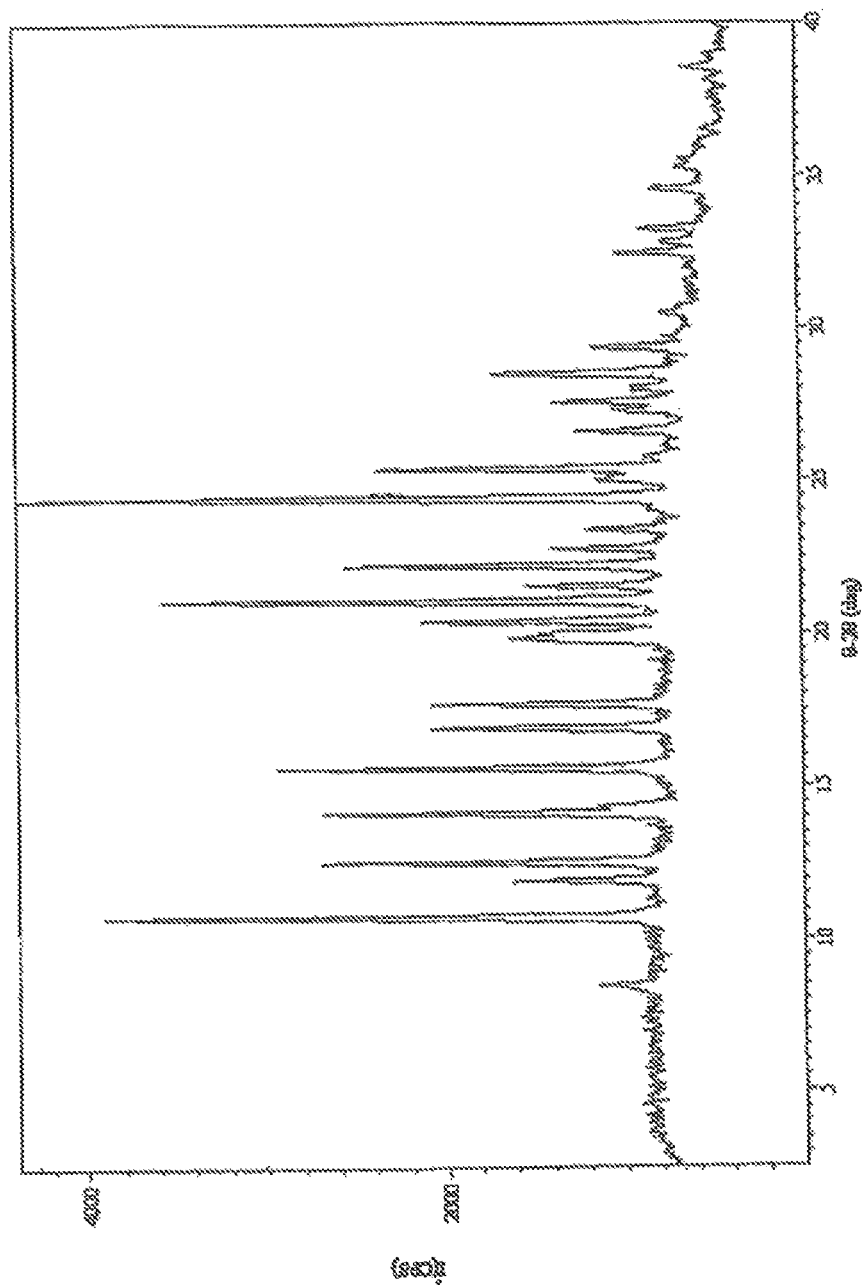
FIG. 1 is an x-ray powder diffraction (XRPD) pattern of sulfathiazole solidified from an acetonitrile solution which was sonicated.

Ultrasound generally refers to sound vibrations beyond the limit of audible frequencies. Ultrasound is often used to refer to sound vibrations having a frequency of about 20 kHz or more. In many applications where ultrasound is used, the frequencies are in the range of 20 kHz to 5 MHz. However, the definition of ultrasound as having a frequency greater than 20 kHz is related to the average perception limit of the human ear rather than to industrial applications. The benefits of the present methods may be obtained with frequencies below 20 kHz. In the context of the present specification, ultrasound refers to sound vibrations having a frequency in the range of from about 10 kHz to about 10 MHz. However, for certain applications, ultrasound having frequencies in narrower ranges (such as, for example, from about 20 kHz to about 5 MHz or from about 40 kHz to about 2.5 MHz) may be desired.

The terms sonicate and sonication are frequently used to refer to the application of ultrasound. A sample (for example, a solution or suspension) may be sonicated in a variety of ways, and may be sonicated continuously or by one or more pulses. For example, a sample may be sonicated by a series of ultrasound pulses, each pulse having a duration of from about 0.1 second to about 10 seconds. As another example, the sample may be sonicated at least once for at least about 5 minutes. In the present methods, where a method requires sonication or sonicating, it requires at least one pulse of ultrasonic energy which is generally on the order of seconds (for example, applying ultrasonic energy for 1 second or less, 5 seconds, 10 seconds or more). When a solution, suspension, solvent or other composition is sonicated "while" or "during" some other step or time period, it means at least one pulse is applied—it does not necessarily mean there is sonication over the entire step or period, although in some circumstances, it can be desirable to sonicate periodically or continuously throughout substantially an entire step or over substantially all of a time period, or for some portion of the step or period. For example, in some of the present techniques, it is stated that a solution is sonicated while a solvent is evaporated. Sonication in this situation may be a single pulse (for example, 5 seconds) to a solution, as well as multiple pulses or continuous sonication of a solution over substantially the entire time period of evaporation, or any application of ultrasound in between.

Ultrasound can be applied to a chemical substance or a sample by conventional techniques such as by immersing a receptacle containing the chemical substance or the sample in an ultrasonic bath, or by placing the tip of an ultrasonic probe directly into the sample. Sonication may toe performed using commercially available equipment. For example, a quarter-inch diameter (6 mm) ultrasonic probe operating at 20 kHz and a power input of 130 watts has been found convenient, but there will be many other commercially available devices which are suitable. Lower power ultrasound, apparatus may also be suitable for crystallization. Suitable ultrasound devices are advertised by Cole-Palmer Instrument Co., of Vernon Hills, Ill., or Misonix Corporation, of Farmingdale, N.Y. For larger scale operations, a sonoreactor is advertised by AEA Technologies of the United Kingdom. Techniques and equipment include the use of ultrasonic probes or transducers, which techniques will be familiar to those skilled in the art.

Where the samples are provided in a well plate, a well-plate sonicator may be used to sonicate the samples. Sonication of the sample may be performed using commercially available equipment. For example, a quarter-inch diameter (6 mm) ultrasonic probe operating at 20 kHz and a power input of 130 watts has been found convenient, but there will be many other commercially available devices which are suitable. As another example, a probe sonicator may be used for 2-5 seconds at 40 mW of power using a ⅛-inch probe. Lower power ultrasound apparatus may also be suitable for crystallization. The amount of time and power of the sonication are variable. In the example described below, sonication times of about 10 to 15 seconds applied every 5 minutes or so were used with a Misonix well-plate sonicator at medium power.

The application of ultrasound to a sample containing a chemical substance to be crystallized can reduce the Metastable Zone Width for the sample (for example, a solution containing the chemical substance and solvent). For example, the sample may have a metastable zone, and the metastable zone has a width of at least about 1° C., alternatively at least about 2° C., alternatively at least about 5° C., alternatively at least about 10° C. The application of ultrasound to the sample may narrow the metastable zone, for example from a width of greater than about 10° C. to a width of at most about 5° C., or by reducing it by at least about 1° C. A reduction of the Metastable Zone Width offers a way to limit the level of supersaturation at which nucleation occurs. For a chemical substance that has two unsolvated polymorphic forms, where one is stable and one is metastable at a given temperature, the polymorph of higher free energy (that is, lower stability) has a higher solubility in any solvent compared to the polymorph of lower energy. If there is sufficient reduction of the Metastable Zone Width by application of ultrasound, such that the system becomes supersaturated with respect to the most stable form while being undersaturated with respect to the other form, then polymorphic selection favoring the most stable form will occur. This "zone of action" may be used in order to increase the chances to generate the most stable form of a chemical substance. In practice, as ultrasound does not typically reduce the Metastable Zone Width to zero, cases may occur where two polymorphs of similar of energy can be formed. Ultrasound can therefore be used as a tool to increase the probability of generating the most stable form, when working under low levels of supersaturation, or selectively crystallizing the more stable of two solid forms.

Sometimes the most stable solid form is more difficult to generate than a less stable form. For example, with the compound WAY, the yellow form is frequently the first and most common form generated in screening method using small-scale crystallization and a variety of solvent mixtures. This may be explained by a faster nucleation and/or growth rate of the less stable form, compared to the more stable form.

The application of ultrasound to a chemical substance to be crystallized from a solution can induce nucleation of supersaturated solutions in cases where the substance otherwise remains indefinitely or for relatively long periods in solution (in other words, in metastable solution). In this respect, the application of ultrasound is of considerable interest to find new solid forms difficult to find due to difficult conditions of crystallization. For example, the present techniques are beneficial for crystallization and finding new solid forms from viscous solutions, or from systems having a large Metastable Zone Width.

Sonication generally increases the rate of nucleation in samples that are sufficiently supersaturated relative to the desired multi-component phase (the active agent(s) and the guest(s)). For example, sonication may increase the rate of cocrystallization by at least about 25%, alternatively at least about 100%, alternatively at least about 200%. Sonication generally reduces the activation barrier to nucleation and increases the number of successfully nucleated samples. The precise nature of the physical perturbations that cause nucleation when a sample is sonicated are not known with certainty. While the inventor does not intend to be bound by theory, it is presently theorized that entropic contributions may be more significant in multi-component samples because the independent components must be organized not only on a molecular level via aggregation through hydrogen bonding, but also in terms of mass transport. The growth of a cocrystal requires a consistent addition of a 1:1 mixture (or other fixed ratio) of the components to the cocrystal structure. Accordingly, local concentration gradients within the sample are undesirable. Sonication has a homogenizing effect and may assist in generating a more homogeneous distribution of the components in the sample. Thus, sonication is especially well-suited for methods of screening cocrystals where multiple compounds are to be brought together in a crystal. Sonication is also well-suited for methods of screening salts where an ionizable active agent and a counterion are to be brought together in a crystal.

Ultrasound may be particularly beneficial where multi-component crystal growth is nucleation-limited. A system is nucleation-limited where crystals are generally not observed if nucleation does not occur during evaporation, and an amorphous solid results instead. In a nucleation-limited system, if nucleation occurs, then subsequent growth occurs efficiently and substantially completely. For example, a combination of fluoxetine HCl and benzoic acid in a 1:1 molar ratio is nucleation-limited in solutions of acetonitrile. This is a difficult system to nucleate and a minimum desired supersaturation level has been identified for cocrystallization. The minimum desired supersaturation level for fluoxetine HCl and benzoic acid in a 1:1 ratio in acetonitrite is about 35 mg/ml. Using the technique disclosed herein, minimum desired supersaturation levels for other systems can also be found.

It has also been discovered that, even with ultrasound, it is desirable to maintain certain levels of supersaturation in the sample. In experiments using fluoxetine hydrochloride and benzoic acid in samples that included acetonitrile as a solvent, it was observed that sonication had a positive effect on cocrystallization. When concentrations of above 200 mg/ml of the mixture of active agent and guest in acetonitrile were used, sonication consistently nucleated the cocrystal. Between 35 and 100 mg/ml, nucleation could be caused by sonication, but nucleation was not observed spontaneously in unsonicated samples with concentrations below 100 mg/ml. Sonication provides a clear advantage in this case with respect to intermediate concentrations.

Experiments at a concentration of about 200 mg/ml nucleated with sonication using either a probe or a well-plate sonicator. About 50% of wells nucleated and about 98% of the solids were cocrystals. In a control experiment without sonication, only about 15% of the wells nucleated, and the solid was benzoic acid rather than a cocrystal of fluoxetine HCl and benzoic acid.

The application of ultrasound to the solution or suspension may narrow the metastable zone, for example, reducing it to less than 1° C. or from a width of greater than about 10° C. to a width of at most about 5° C. It appears that sonication reduces the metastable zone width, causing nucleation at lower supersaturation levels compared to slow evaporation (SE) results.

Sonication can increase the rate of nucleation in systems where nucleation is slow. Among the advantages of sonication are that nucleation can occur faster, more completely, and can be initiated at lower concentrations. In addition, the rapid nature of the growth is more likely to produce a consistent form (the first form that nucleates) because of the massive secondary nucleation that occurs during sonication—one seed becomes many very quickly due to sonication. Ultrasound can therefore be used as a tool to increase the probability of generating a cocrystal, to generate cocrystals more rapidly, and/or to generate cocrystals at relatively low levels of supersaturation.

Ultrasound may also be useful as a tool to increase the probability of generating—a crystallized salt, to generate salts more rapidly, and/or to generate crystallized salts at relatively low levels of supersaturation.

The present methods are useful for the generation of new solid forms as well as for screening a chemical substance according to its solid forms. The chemical substance may be a compound, element, or mixture. Chemical substances include organic and inorganic substances. Examples of chemical substances for use in the present techniques include, but are not limited to, pharmaceuticals, dietary supplements, alternative medicines, nutraceuticals, agricultural chemicals, dyes, explosives, polymer additives, lubricant additives, photographic chemicals, and structural and electronic materials. Preferably, the chemical substance is a pharmaceutical agent. Pharmaceutical agents suitable for use in the present technique include known pharmaceutical agents as well as those which may be developed. A pharmaceutical agent can be a large molecule (in other words, a molecule having a molecular weight of greater than about 1000 g/mol), such as oligonucleotides, polynucleotides, oligonucleotide conjugates, polynucleotide conjugates, proteins, peptides, peptidomimetics, or polysaccharides. A pharmaceutical agent can be a small molecule (in other words, a molecule having a molecular weight of about 1000 g/mol or less), such as hormones, steroids, nucleotides, nucleosides, or aminoacids. Examples of suitable small molecule pharmaceuticals include, but are not limited to, cardiovascular pharmaceuticals; anti-infective components; psychotherapeutic components; gastrointestinal products; respiratory therapies; cholesterol reducers; cancer and cancer-related therapies; blood modifiers; antiarthritic components; AIDS and AIDS-related pharmaceuticals; diabetes and diabetes-related therapies; biologicals; hormones; analgesics; dermatological products; anesthetics; migraine therapies; sedatives and hypnotics; imaging components; and diagnostic and contrast components.

The chemical substances can have any utility, including utility as a pharmaceutical agent or other active agent. The present methods increase the likelihood of determining whether a chemical substance is polymorphic. A polymorphic chemical substance is a compound, element, or mixture having more than one solid form. The form of a compound, element, or mixture refers to the arrangement of molecules in the solid. The term solid form herein includes semisolids. Semisolids are materials like waxes, suspensions, gels, creams, and ointments. The forms which may be sought or generated may include amorphous forms, mixtures of amorphous forms, eutectic mixtures, mixed crystal forms, solid solutions, co-crystals, and other forms.

A chemical compound, element, or mixture may be amorphous, meaning that it is not characterized by a long-range order of the molecules. Alternatively (or even to a limited extent within a mostly amorphous form), a compound, element, or mixture may be arranged in a crystalline state, where the molecules exist in fixed conformations and are arranged in a regular way. The same compound, element, or mixture may exhibit different properties depending upon which solid form that compound, element or mixture is in.

Examples of compounds having more than one solid form include 5-methyl-2-[(2-nitrophenyl)amino]-3-thiophenecarbonitrile and 4-methyl-2-nitroacetanilide, each of which has different colors in connection with different forms. Carbon, novobiocin, and furosemide are also examples of substances having more than one solid form.

The present disclosure provides techniques for preparing cocrystals and for screening a chemical substance according to its possible solid state phases, in which one or more active agents are cocrystallized with one or more guests. It has been found that ultrasound may be used to facilitate cocrystallization and screening.

Figure 8:
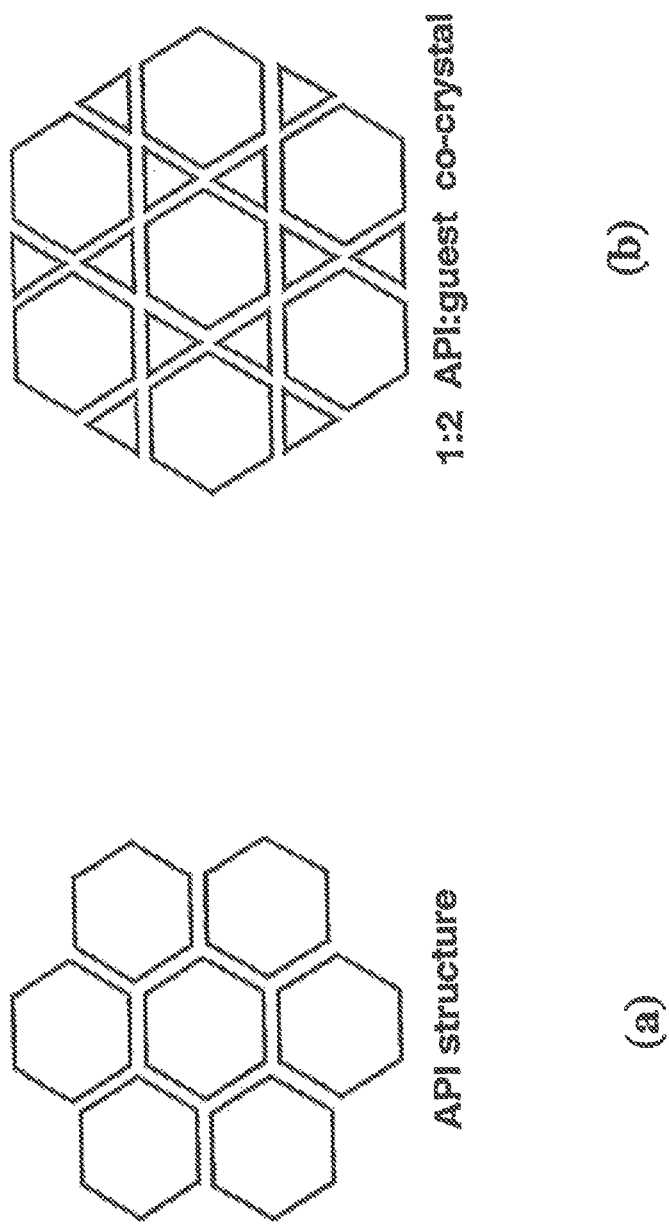
FIGS. 8 (a) and (b) illustrate a crystal structure of an active agent and a cocrystal structure containing the same active agent with a guest.

Cocrystals are crystals that contain two or more non-identical molecules (two or more components) such as an active agent and a guest. FIGS. 8($a$) and ($b$) illustrate a crystal structure of an active agent (a one-component crystal) and a cocrystal structure containing the same active agent with a guest (a two-component crystal), respectively.

Generating a variety of solid forms is an object of screening. A sufficient number of diverse processes and parameters should be employed to maximize the likelihood that a high percentage of possible solid forms of a chemical substance is generated. Samples should be generated under various thermodynamic and kinetic conditions. In the present methods, sonication is another parameter that is varied as part of the screening process.

A compound is a substance composed of atoms or ions in chemical combination. A compound usually is composed of two or more elements, though as used in accordance with the present methods, a compound may be composed of one element.

A mixture is a heterogeneous association of compounds or elements. The components of a mixture may or may not be uniformly dispersed.

The present methods include providing samples comprising the chemical substance(s). In some embodiments, the samples may contain the chemical substance(s) alone, for example, in a melt or a physical mixture. More commonly, the sample will also contain a solvent(s) in which the active agent(s) and the guest(s) are dissolved, dispersed or otherwise disposed. The active agent(s) and the guest(s) may be completely or partially soluble in the solvent(s) or one or more of them may be substantially insoluble in the solvents. Accordingly, the sample may be in a solution, suspension, dispersion, mixture, slurry or emulsion, or other physical state. The sample's physical state going into the present methods is not critical to the broader applicability of the present methods, though in some embodiments, use of particular physical states for samples can be beneficial, as described in more detail herein. For example, the present methods may have additional benefits when the samples are metastable solutions, viscous solutions, emulsions or slurries.

In the present methods, the chemical substance is solidified from the sample using a suitable solidification technique. As used herein, solidification includes any suitable technique for preparing a solid from the sample including but not limited to crystallization.

The solidification technique(s) employed will depend in part on the sample(s). The samples may be provided as solutions, suspensions, melts, slurries, emulsions, or any other composition of matter which includes the chemical substance.

Suitable crystallization (solidification) techniques include cooling, heating, evaporation, addition of an antisolvent, reactive crystallization, and using supercritical fluids as solvents. A fluid is an antisolvent with respect to a given solution of a chemical substance when the chemical substance is less soluble in that fluid than in the solvent used to form the solution; preferably, an antisolvent is a fluid in which the chemical substance is essentially insoluble or has a low solubility. Reactive crystallization refers to processes where means a chemical substance is formed from reactants and crystallized substantially simultaneously, for example, where the reaction is a driving force toward crystallization. A supercritical fluid is a fluid above its critical temperature and critical pressure which combines properties of gases and liquids.

Examples of compounds employed as supercritical fluids include xenon, ethane and carbon dioxide.

Alternatively, the mechanism by which crystallization is accomplished may include gel diffusion methods, thin-layer deposition methods, or other suitable methods. Other thermodynamic and kinetic conditions may be employed to solidify the compound or mixture. Slow cooling of a saturated solution is a typical thermodynamic condition. An addition of a solution of the compound or mixture to an excess of cold anti-solvent is a typical kinetic condition.

Additionally, melt crystallization techniques may be used to generate a solid form. Through such techniques, the use of a solvent can be avoided. In such techniques, formation of crystalline material is from a melt of the crystallizing species rather than a solution. Additionally, the crystallization process may be done through sublimation techniques.

In many embodiments, the samples will comprise the chemical substance in a solvent. Any suitable solvent can be used. Suitable solvents include acetone, acetonitrile, chloroform, dioxane, ethanol, ethyl acetate, heptane, butanone, methanol, nitromethane, tetrahydrofuran, toluene, water, dichloromethane, diethyl ether, isopropyl ether, cyclohexane, methyleyelohexane, isopropyl alcohol, isopropyl acetate, trimethylpentane, n-octane, trichloroethane, trifluoroethanol, pyridine, propanol, butanol, tetrachloroethylene, chlorobenzene, xylene, dibutyl ether, methyl-tert-butyl ether, tetrachloroethane, p-cymene, dimethyl sulfoxide, formamide, and dimethylformamide. It is also contemplated that the samples may be provided as the chemical substance in two or more solvents, either as a homogeneous solution or as an emulsion.

In the solidifying step, the chemical substance is generally separated from the solvent though solids such as hydrates or solvates may be formed which include some solvent molecules. For example, the solvent may be evaporated either slowly (for example, evaporating to dryness over a time period of four days, alternatively two days or more) or quickly (for example, evaporating to dryness over a time period of 24 hours, alternatively under two days). By varying the rate of evaporation, one can introduce desired variability into a screening method. For example, in a screening method, a first portion of samples can be subjected to relatively slow evaporation, and a second portion of the samples can be subjected to relatively fast evaporation.

In the present methods, ultrasound may be applied at different stages of a screening process or a crystallization process (or other solidification process). For example, a solution which comprises a solute to be crystallized can be sonicated at some point during the screening process. One may sonicate such a solution before, during, or after the initiation of cooling of the solution from an undersaturated, saturated, or supersaturated state. As other examples, one may sonicate a solution before, during, or after the beginning of evaporation of solvent, or before, during, or after the addition of an immiscible antisolvent to the solution.

In the present methods, the solidifying step and the sonicating step can overlap. For example, where the samples are provided as a solution of the chemical substance in a solvent, the solidifying step may be performed by evaporating the solvent, and the sample may be sonicated during that evaporation. Furthermore, the sonication can be periodic during the evaporation. For example, the sample can be periodically sonicated for about 20 seconds, and the periods can be about 30 minutes (in other words, the sample is sonicated for about 20 seconds every 30 minutes). Furthermore, the sonication can be a single pulse. For example, the sonication could be carried out one time for 5 to 40 seconds or multiple times for a like period, or for other suitable period(s).

In the present methods, the samples can comprise a solution, suspension, or melt of the chemical substance. Such a solution, suspension, or melt will typically be prepared by heating above room temperature to achieve supersaturation. It may be desirable to begin cooling the samples (for example, to room temperature) before the sonicating step. Alternatively, the samples may be cooled and sonicated at the same time. Alternatively, the method can include crash-cooling the samples (rapidly lowering the temperature, for example, by immersing in an ice bath) before the sonicating step. Alternatively, the samples may be crash-cooled and sonicated at the same time.

The present methods can include the step of adding a second solvent to a solution containing the chemical substance. For example, the second solvent may be added to facilitate solidification.

The solidification step can be initiated by sonication, and/or it may be initiated by seed materials or other techniques. In the various embodiments of the present methods, solidification may start before, during, or after the application of ultrasound. Frequently solidification will start during sonication and continue after sonication ceases. In many cases, the solidification and sonication steps will overlap. For example, sonication may begin before solidification but continue even after solidification begins. As another example, solidification may begin before sonication. As yet another example, the chemical substance may be sonicated in a pulsing manner throughout the solidification process. Alternatively, sonication may be employed to initiate solidification and be discontinued when solidification (such as nucleation) begins.

As a broad example, solidification may be performed as follows: A solution containing a solvent and a chemical substance (such as a compound, element, or mixture) to be solidified is disposed in a receptacle, such as a vial, well-plate (such a 96 well plate) or capillary tube. The solution may be formed in the receptacle or formed outside the receptacle and then placed in it. The chemical substance can be present in a solution below, at or above its saturation point at a given temperature at the time it is placed in the receptacle. Through evaporation, the use of an antisolvent, temperature variation, and/or other suitable means, the solution reaches a point of supersaturation. The solution is sonicated, and further evaporation, the use of an antisolvent, temperature variation, and/or other suitable solidification technique may be employed. After a suitable amount of time, solidification progresses until a sufficient amount of solid or semisolid appears, and is ready for analysis to determine the solid form.

The most preferred solidification techniques foster crystallization of the chemical substance. Suitable crystallization techniques may be employed with and without ultrasound in the present methods. Indeed, in a screening method, it may be desirable that some samples are sonicated and other samples are unsonicated.

Crystallization may be performed as a seeded operation or an unseeded operation. In a seeded operation, a selected quantity of seed crystals is included in the system. The characteristics of the seed crystals typically influence the characteristics of the crystals generated from the system. Crystallization may be performed by heterogeneous or homogeneous mechanisms. However, it is noted that ultrasound may be applied as a way of omitting the presence of seed crystals.

In other embodiments of the present methods, solids are generated other than by crystallization. The sample may be provided as a melt that is then added to the receptacle or may be provided within the receptacle and melted therein and allowed to solidify in an amorphous form.

Another technique for crystallizing a chemical substance employs an emulsion. An emulsion is a mixture of two or more immiscible liquids where one liquid is in a discontinuous phase within the other liquid. Emulsions are frequently formed and/or stabilized by the use of agents called emulsifiers. However, sonication of an immiscible mixture of solvents also allows the generation of emulsions.

The present methods may also include the step of forming an emulsion comprising two or more substantially immiscible solvents and the chemical substance. The emulsion can be formed during the sonicating step, wherein an immiscible mixture of said solvents is sonicated to form the emulsion. Alternatively, the emulsion can be formed before the sonicating step. Where an emulsion is employed, the chemical substance can be substantially soluble in one of the immiscible solvents and substantially insoluble in another of the immiscible solvents. The chemical substance is in solution in one or both of the solvents.

Emulsions can be employed as part of a screening method and/or solidification method to generate additional solid forms of a chemical substance. Emulsions can allow interface between the two solvents over a high surface area. At such interfaces, nucleation and/or growth of some polymorphs may be favored, based on the influence of each solvent on the growth of each polymorph.

An emulsion may be prepared by combining a solution of a chemical substance in a first solvent with a second solvent, wherein the first solvent and the second solvent are substantially immiscible with each other. The combined solvents may then be sonicated while evaporating, cooling, adding antisolvent, or using other solidification techniques until a precipitate containing the chemical substance appears.

Another technique for crystallizing a chemical substance employs a slurry. A slurry is a dispersion of solid particles in a liquid phase. The liquid phase comprises one or more solvents in which the chemical substance is not completely soluble. The process of slurrying a metastable form of a chemical substance, aiming at finding a form of lower solubility in the solvent used, in other words, a form of lower energy (in the case of the transition between two unsolvated polymorphs) or a solvated form (in the case of a transition between an unsolvated form or solvated form from a different solvent to a solvated form), is foreseen to be accelerated by the use of ultrasound during the slurrying process.

The present methods may also include the step of forming a slurry comprising a solvent and the chemical substance. The slurry can be formed during the sonicating step, wherein a mixture of the chemical substance and the solvent are sonicated to form the slurry. Alternatively, the slurry can be formed before the sonicating step.

It is preferable in a screening method that the generation of solid forms is carried out under a wide variety of conditions. For example, solids should be generated in the presence and absence of various solvents, as the solvent may play a role in the formation of certain forms, and with and without sonication. As another example it is also preferable to prepare solid forms under different conditions of temperature and pressure, as different solid forms may be favored by different conditions. In some embodiments of the screening method, at least one sample is unsonicated so that the effect of ultrasound, on solid form for that chemical substance can be determined.

It is also contemplated that the present methods are advantageous for generating solid forms from viscous solutions. For example, the present methods may be used with samples that are solutions having a viscosity greater than about 5 cPoise, alternatively greater than 10 cPoise, alternatively greater than 20 cPoise, before the solution is sonicated.

It is also contemplated that the present methods are advantageous for generating solid forms from amorphous forms of the chemical substance. Samples can be formed or provided by preparing a solution from an amorphous solid comprising the chemical substance and a solvent. The solvent may be sonicated while the amorphous solid is added to the solvent.

It is contemplated that, in the context of a comprehensive screening method, the samples can be divided into subsamples or sets of subsamples. A multiplicity of subsamples and sets are useful so that more than one parameter may be varied and the cumulative effect of multiple varied parameters may be assessed. For example, a first sample (and/or a second sample) may be divided into subsamples, such as a first set of subsamples, a second set, a third set, and a fourth set. The first set and the second set can comprise a solution of the chemical substance in a first solvent, such as acetone, while the third set and the fourth set comprise a solution of the chemical substance in a second solvent, such as tetrahydrofuran. The first set and the third set can be sonicated, and the second set and the fourth set can be unsonicated. The benefit of this method is that the effects of ultrasonic crystallization on acetone and tetrahydrofuran solutions can be analyzed and compared.

Solid forms generated after the solidification and sonication steps may be identified by any suitable method, including but not limited to visual analysis (such as when different forms exhibit different colors), microscopic analysis including electron microscopy (such as when, different forms happen to have different morphologies), thermal analysis (such as determining the melting points), conducting diffraction analysis (such as x-ray diffraction analysis, electron diffraction analysis, neutron diffraction analysis, as well as others), conducting Raman or infrared spectroscopic analysis, or conducting other spectroscopic analysis. Any appropriate analytical technique that is used to differentiate structural, energetic, or performance characteristics may be used in connection with the present methods.

In a preferred embodiment, the samples are placed in a well plate and then sonicated. The chemical substances solidify in the wells of the well plate. The solidified chemical substances are then analyzed in the well plate or a portion of the well plate. The solidified chemical substances can be analyzed by any one of the foregoing analysis techniques, preferably by x-ray diffraction (such as transmission x-ray diffraction or reflection x-ray diffraction) and/or by Raman spectroscopy. Well plates may be used which have a detachable portion, such as a detachable bottom portion. For example, well plates may be used which have polymer films, glass plates, or other substrates that are detachable from another portion of the well plates. Solidified chemical substances can be analyzed in the well plate or the detachable portion of the well plate. In particular, x-ray diffraction techniques such as transmission or reflection x-ray diffraction may be used to analyze the solidified chemical substances in well plates or the detachable portion of well plates (for example, the polymer film, glass plate, or other substrate).

A synchrotron may be used as the source of radiation for conducting diffraction analyses. A synchrotron is a type of particle accelerator, which emits high energy, focused radiation. Synchrotron radiation is the byproduct of circulating electrons or positrons at speeds very close to the speed of light. Synchrotron radiation contains all the wavelengths of the electromagnetic spectrum and comprises the most intense source of wavelengths available in the x-ray and ultraviolet region. Synchrotron radiation allows analysis of smaller quantities of sample that would be difficult to analyze using other sources of x-ray radiation.

One location for research using synchrotron radiation is the Stanford Synchrotron Radiation Laboratory (SSRL), which is funded by the Department of Energy as a national user facility. Another location is Argonne National Laboratory, which is available to outside users on a fee basis.

Synchrotron radiation may be used to study structural details of solid samples with a resolution not practically attainable using traditional x-ray instrumentation. This may enable differentiation between different polymorphic forms or compounds that is not attainable with other x-ray radiation sources.

The present methods can significantly assist in the identification of the solid form of a chemical substance that is most stable or has other properties that make it preferable over other forms. For example, the present methods can be used as part of a screening method and can improve the likelihood of identifying a form having biological activity such as better stability, bioavailability, solubility, or absorption characteristics. In some cases, an identified form may have better activity as an active agent.

After a chemical substance (including a solution, melt, emulsion, slurry, suspension, or mixture containing the chemical substance) is placed in a receptacle, the receptacle may be centrifuged. Centrifugation may be employed for a variety of reasons. First, use of a centrifugal evaporator may assist evaporation while concentrating solid or semisolid material at one end of a capillary space. This has advantages in connection with in-situ analysis, in that the generated form will be located at a consistent place in the receptacle. Also or alternatively, centrifuging may be used to provide additional environmental variation, which is desirable in a screening method.

The application of ultrasound to solutions containing multiple components to be crystallized can induce nucleation in cases where the components otherwise remain indefinitely or for relatively long periods in solution (in other words, in metastable solution). In this respect, the application of ultrasound is of considerable interest to find new cocrystals and salts which are otherwise difficult to find. For example, the present techniques are beneficial for cocrystallization from viscous solutions, or from systems having a large Metastable Zone Width.

The present techniques are applicable to cocrystallize two or more active agents. (It is contemplated that more than one active agent may be employed in a cocrystal.) An active agent is a molecule whose activity is desirable or the object of interest. For example, where the active agent is an active pharmaceutical ingredient, the pharmaceutical activity of the active agent is desired or the object of interest. Active agents include organic and inorganic substances. Examples of active agents for use in the present techniques include, but are not limited to, pharmaceuticals, dietary supplements, alternative medicines, nutraceuticals, agricultural chemicals, dyes, explosives, polymer additives, lubricant additives, photographic chemicals, and structural and electronic materials. Preferably, the active agent is an active pharmaceutical ingredient (API). Pharmaceutical agents suitable for use in the present technique include known pharmaceutical agents as well as those which may be developed. A pharmaceutical agent can be a large molecule (in other words, a molecule having a molecular weight of greater than about 1000 g/mol), such as oligonucleotides, polynucleotides, oligonucleotide conjugates, polynucleotide conjugates, proteins, peptides, peptidomimetics, or polysaccharides. A pharmaceutical agent can be a small molecule (in other words, a molecule having a molecular weight of about 1000 g/mol or less), such as hormones, steroids, nucleotides, nucleosides, aminoacids, acetaminophen, nonsteroidal anti-inflammatory drugs, and others. Examples of suitable small molecule pharmaceuticals include, but are not limited to, cardiovascular pharmaceuticals; anti-infective components; psychotherapeutic components; gastrointestinal products; respiratory therapies; cholesterol reducers; cancer and cancer-related therapies; blood modifiers; antiarthritic components; AIDS and AIDS-related pharmaceuticals; diabetes and diabetes-related therapies; biologicals; hormones; analgesics; dermatological products; anesthetics; migraine therapies; sedatives and hypnotics; imaging components; and diagnostic and contrast components.

The active agent may be provided as a salt. It is contemplated that one or more salts may be employed in a cocrystal, according to any of the present techniques. The salt may be prepared from an ionizable active agent or obtained from a commercial source. Hydrochloride salts of active pharmaceutical ingredients, especially of amine APIs, are especially preferred in the pharmaceutical industry.

In general, it is contemplated that the present techniques will have particularly good results as applied to amine HCl salts as well as other ammonium salts as described in more detail herein. In ammonium acid salts, the active agent has at least one amine moiety which is relatively basic (at least one relatively basic nitrogen), and a salt is formed with an acid that reacts with the amine moiety. Cocrystals may be then formed between the ammonium salts and guests which act as hydrogen-bond donors to the salts. Cocrystals may be formed, of chloride salts of APIs, for example buspirone hydrochloride and fluoxetine hydrochloride.

While the inventors do not wish to be bound to theory, it is believed that excellent cocrystals may be formed using hydrochloride salts and similar salts which are strong hydrogen bond acceptors yet contain relatively undercoordinated ions. "Undercoordinated" in this case refers to ions, for example a chloride ion, that are able to form a number of strong hydrogen bonds. An undercoordinated counterion may have hydrogen bonds within a crystal of that salt, but it could form additional hydrogen bonds in a cocrystal and/or form relatively stronger hydrogen bonds in a cocrystal with a guest. An ion is "undercoordinated" when the system is limited in the number of hydrogen bond donors that are available and bonded to the ion. In these cases, the extra hydrogen bond acceptor sites are typically filled by weakly interacting donors such as C—H groups. Chloride ions are strong hydrogen bond acceptors in a crystal structure. In a crystal structure such as fluoxetine hydrochloride, the chloride ion coordinates to the two strong hydrogen bond donors available in the system, and the chloride ion also has three weaker CH—Cl interactions resulting in a pseudo-octahedral coordination environment. There is an opportunity for bonding with these coordination sites, by displacing the weak CH donors that the chloride has recruited to fill its coordination sphere with somewhat stronger hydrogen bond donors from a guest such as benzoic acid, succinic acid, fumaric acid, or another carboxylic acid.

It is useful in forming cocrystals to recognize that relatively weak interactions may be replaced by stronger interactions, even though those stronger interactions may be relatively weak themselves, compared to other interactions. For example, an undercoordinated chloride may have one strong hydrogen bond donor and several weak hydrogen bond donors or two strong hydrogen bond donors and several weak hydrogen bond donors. In a cocrystal, weaker interactions may be replaced by stronger interactions, although those stronger interactions may still be weaker than the strong interactions (charge-assisted hydrogen bonds) present in fluoxetine HCl crystals. The strongest interactions involving chloride ions in crystal structures of organic salts are the charge assisted hydrogen bonds that invariably form between the protonated nitrogen base and the chloride ion. The strongest interactions between neutral molecular groups and the chloride ion involve acids and the chloride ion. Carboxylic acids, for instance, have strong interactions with chloride ions. It can be seen that a combination of carboxylic acids and hydrochloride salts of nitrogen containing bases are especially well suited to cocrystal formation (as demonstrated by the examples included). Furthermore, it can be anticipated that different combinations of these elements could lead to other cocrystals. For example, the active molecule of interest may contain either the neutral carboxylic acid moiety or the protonated nitrogen. The potential exists to cocrystallize an API having a neutral carboxylic acid moiety with a guest that is a hydrochloride salt of a nitrogen-containing organic base.

It is further contemplated that the nature of the protonated nitrogen base will affect the potential for cocrystallization. Numerous strong hydrogen bond donor groups will compete with the carboxylic acid guest for the open acceptor sites on the chloride ion. In order to favor cocrystal formation, the nitrogen base is preferably a tertiary amine because this presents a situation where only one strong charged hydrogen bond donor exists and thus will only occupy one site on the chloride acceptor. Additionally, systems that have only this one tertiary amine and no other strong donors present an especially favorable system for potential cocrystallization. Protonated secondary amines with two N—H donor groups are also favored, although protonated primary amines may also be used. Special consideration must be taken for systems with additional strong hydrogen bond donor and acceptor sites in order to determine the potential for cocrystallization and the optimal guest molecule type for cocrystallization. The potential for cocrystallization involving a carboxylic acid and a hydrochloride salt may be reduced as the number of available strong donors in the system is increased. Additional guidance as to evaluating undercoordination particularly in its discussion of nonbonded motifs may be found in: Scott L. Childs, "Nonbonded Interactions In Molecular Crystal Structures," Emory Univ., USA, available from UMI, Order No. DA3009424 (288 pp.), Dissertation Abstract Int. Ref. B2001, 62(3), 1394 (which is incorporated by reference herein). In some circumstances, the undercoordination can be determined by measuring distances, comparing profiles in the Cambridge Structural Database, measuring the pKa of the donors and acceptors, or evaluating the ratio of strong hydrogen bond donors to available acceptors. Other crystal engineering theories may also be used.

By cocrystallizing an active agent with a guest, one can create new solid state phases which may have improved properties over existing solid state phases of that active agent. For example, new drug formulations comprising salt of active pharmaceutical ingredients may have superior properties over existing drug formulations. The active agent and guest will vary depending on the industry. For example, in the pharmaceutical field, the active agent or guest may be an API, and the other component of the salt must be a pharmaceutically acceptable compound. The present techniques are also applicable to active agents from other fields including nutraceuticals, agricultural chemicals, pigments, dyes, explosives, polymer additives, lubricant additives, photographic chemicals, and structural and electronic materials.

The present techniques may be employed to generate a wide variety of cocrystals of active agents and guests. For example, the present techniques may be used to generate cocrystals of a salt of an active agent, such as a salt of an active pharmaceutical ingredient, with a neutral guest. Alternatively, a cocrystal of a neutral or zwitterionic active agent (or a salt of an active agent) may be generated with a guest salt, which includes a positive ion and a negative ion of its own. Where the active agent is provided in a salt, it may be positively or negatively charged and have a negative or positive counterion. As an example, for fluoxetine HCl, the active agent fluoxetine is positively charged by virtue of accepting a proton from HCl to form a protonated amine, and chloride is present as a negative counterion. Furthermore, some of the present methods may be employed with a neutral or zwitterionic active agent to form a cocrystal with a neutral guest or ionic guest.

The present techniques provide an opportunity to create a stable solid state phase of a hydrochloride salt of an API (or other active agents) that was previously found to have properties that were unsuitable for development. Opportunities for continued development in such a situation have often relied on the fortuitous formation of a stable hydrate or solvate, but the present techniques present the ability to systematically examine alternative formulations of the hydrochloride salt by cocrystallizing the hydrochloride salt of the API with appropriate guest molecules.

Cocrystallization may be an attractive technique for salts of APIs that have been rejected due to problems relating to physical properties. Since cocrystals may have different physical properties than the individual components, APIs with unfavorable physical properties can be cocrystallized with suitable guest molecules and the physical properties of the resulting crystalline solids can be evaluated.

Cocrystals of fluoxetine HCl provide examples of the modification of a physical property (solubility) of an API salt. Cocrystals of fluoxetine HCl:benzoic acid are less soluble and have a lower dissolution rate than crystals of fluoxetine HCl, while cocrystals of fluoxetine HCl:succinic acid are more soluble and have a faster dissolution rate than crystals of fluoxetine HCl.

Other physical properties of APIs or their salts that may be modified by forming a cocrystal include: melting point, density, tiygroscopicity, crystal morphology, loading volume, compressibility, and shelf life. Furthermore, other properties such as bioavailability, toxicity, taste, physical stability, chemical stability, production costs, and manufacturing method may be modified by the use of the present cocrystallization techniques.

An active agent can be screened for possible cocrystals where polymorphic forms, hydrates or solvates are especially problematic. A neutral compound that can only be isolated as amorphous material could be cocrystallized. Forming a cocrystal may improve the performance of a drug formulation of an active pharmaceutical ingredient by changing physical properties. Some APIs are problematic during wet granulation and compression stages. A bioequivalent cocrystal could rectify this problem.

An active agent can also be screened, for possible salts. Forming a salt may improve the performance of a drug formulation by changing physical properties. A salt screen refers to a screening method in which one attempts to make one or more salts comprising an active agent under a variety of conditions and/or parameters, preferably including a variety of different counterions.

A cocrystal or salt can be used to isolate or purify an active agent during manufacturing. If it is desirable to identify the solid state phases of an active pharmaceutical ingredient, then cocrystallization and/or salt formation may be particularly desirable.

The present techniques provide new methods of developing and screening active pharmaceutical ingredients or other active agents. Non-toxic cocrystalline forms of neutral active pharmaceutical ingredients may be prepared, screened, tested, and commercialized. Furthermore, new types of HCl salt structures may be prepared. The properties of hydrochloride salts can be tuned and perfected. New, unique, stable, and marketable phases of hydrochloride salts may be prepared. One can choose whether to make the formulation more soluble or less soluble.

As another aspect, the present techniques may also be used to remove or reduce the water of hydration, and/or to prepare a cocrystal substantially free of water of hydration. Water and guest acids perform a similar role in the stabilization of the crystal structure. In fact, about 28% of the hydrochloride salts of API in the Cambridge Structure Database are hydrates, compared to about 8% of all other organic structures. This indicates an affinity for hydration. The present techniques both capitalize and rectify this affinity, in that an affinity for cocrystallization (as evidence by hydration) is likely indicated, and this affinity for cocrystallization may be employed for the formation of cocrystals with a suitable guest, such as an acid, for example a carboxylic acid. Indeed, in many cocrystals, an acid may have stronger interactions than water molecules and may displace the water of hydration during the formation of the cocrystal. Accordingly, the present techniques provide a method of preparing a cocrystal from a hydrate. A hydrate of a salt is provided, and the hydrate comprises water of hydration. A guest is selected to coordinate with the counterion. Preferably, the guest coordinates more strongly with the counterion than the water of hydration does. A solution, melt or physical mixture is prepared which comprises the hydrate and the guest. The solution or melt is subjected to a crystallization process, or the physical mixture is subjected to grinding, and a cocrystal comprising the salt of the active agent and the guest is formed, and the salt comprises the active agent and a counterion. Similarly, the present techniques provide a method of preparing a cocrystal from a solvate. A solvate of a salt is provided, and the solvate comprises solvent molecules coordinated with the salt. A guest is selected to coordinate with the counterion. Preferably, the guest coordinates more strongly with the counterion than the solvent does. A solution, melt or physical mixture is prepared comprising the solvate and the guest. The solution or melt is subjected to a crystallization process, or the physical mixture is subjected to grinding, and a cocrystal comprising the salt of the active agent and the guest is formed. The salt comprises the active agent and a counterion.

FIGS. 9(a) and (b) are drawings of two-dimensional and three-dimensional models of a cocrystal of fluoxetine HCl and benzoic acid (1:1). FIG. 9(a) shows a two-dimensional model in which the chloride ion interacts with the hydrogens of the amine group of fluoxetine and of the hydroxyl group of benzoic acid. Through these interactions, which may be characterized as hydrogen bonding, fluoxetine hydrochloride and benzoic acid form a supramolecular structure that may be the basis of a cocrystal. FIG. 9(b) shows a three-dimensional model of the supramolecular organization of fluoxetine hydrochloride and benzoic acid.

The present cocrystals may comprise salts other than chloride salts—the hydrochloride API salts that are listed above are only a sampling of the relevant compounds because the starting material need not be a known hydrochloride. Indeed, many relevant APIs are salts that are not HCl salts because the HCl salt was not believed to be an appropriate material and a different salt was commercialized instead. The present techniques may enable one to employ an HCl salt of an API that is marketed as another type of salt. Alternatively, it may be desirable to employ a salt other than an HCl salt, by replacing the HCl or by forming a salt comprising an active agent that acts as a base with an acid other than HCl. The following acids provide anionic counterions that would be used to replace chlorine. These are relatively strong acids, and include but are not limited to mineral acids, and the carboxylic acid guest is expected to form one or more hydrogen bonds with a hydrogen bond acceptor on the anionic counterion. The list is the conjugate acid that would react with a basic active agent to form a salt:

sulfuric acid
phosphoric acid
hydrobromic acid
nitric acid
pyrophosphoric acid
methanesulfonic acid
thiocyanic acid
naphthalene-2-sulfonic acid
1,5-naphthalenedisulfonic acid
cyclamic acid
p-toluenesulfonic acid
maleic acid
L-aspartic acid
2-hydroxy-ethanesulfonic acid
glycerophosphoric acid
ethanesulfonic acid
hydroiodic acid The present techniques also extend beyond salts as starting materials and also include many weak bases that may have been marketed as neutral forms because the known salts did not have appropriate properties. These salts could be revisited and attempts could be made to cocrystallize the HCl salt. For example, a drug formulation marketed as a tartrate salt of an API could be reformulated by cocrystallizing the HCl salt of the active molecule with an appropriate guest molecule. Thus, cocrystallization could make a useful HCl cocrystal out of the API that is currently marketed as a tartrate, sulfate, or other salt formulation. For this reason the present disclosure includes APIs that are not HCl salts as starting materials.

Furthermore, the present techniques relate to salts other than chloride salts. It is contemplated that hydrobromide salts and sodium salts of APIs may especially benefit from the present techniques, since they form relatively strong non-bonded interactions. For example, the hydrobromide salts citalopram hydrobromide and galantamine hydrobromide are contemplated for cocrystallization with benzoic acid, succinic acid, and other guests compatible with hydrochloride salts.

The present techniques may be employed to form cocrystals of sodium salts of APIs such as, for example, naproxen sodium, tolmetin sodium, and warfarin sodium. When a sodium salt (or other salt of an API having a positive counterion) is employed, different guests are expected to be suitable for cocrystallization than when a hydrochloride salt (or other anionic salt) of an API is employed.

Anions and Cations

As one aspect, the active agent is provided as a salt. The salt of the active agent may be formed as part of sample preparation or separately. Alternatively or additionally, the guest is provided as a salt or a salt of the guest is formed. The salt may comprise the active agent and a counterion that is either a cation or an anion. Among the preferred cations (including cations as well as compounds that can form cations) are aluminum, ammonium, benzathine, calcium, diethanolamine, diethylamine, dimeglumine, disodium, lithium, lysine, magnesium, meglumine, potassium, sodium, and zinc.

Among the preferred anions are acetate, L-aspartate, besylate, bicarbonate, carbonate, D-camsylate, L-camsylate, citrate, edisylate, fumarate, gluconate, hydrobromide/bromide, hydrochloride/chloride, D-lactate, L-lactate, DL-lactate, D,L-malate, L-malate, mesylate, pamoate, phosphate, succinate, sulfate, D-tartrate, L-tartrate, D,L-tartrate, meso-tartrate, benzoate, gluceptate, D-glucuronate, hybenzate, isethionate, malonate, methylsulfate, 2-napsylate, nicotinate, nitrate, orotate, stearate, tosylate, acefyllinate, aceturate, aminosalicylate, ascorbate, ascorbate, borate, butyrate, camphorate, camphocarbonate, decanoate, hexanoate, cholate, cypionate, dichloroacetate, edentate, ethyl sulfate, furate, fusidate, galactarate (mucate), galacturonate, gallate, gentisate, glutamate, glutamate, glutarate, glycerophosphate, heptanoate (enanthate), hydroxybenzoate, hippurate, phenylpropionate, iodide, xinafoate, lactobionate, laurate, maleate, mandelate, methanesulfonate, myristate, napadisilate, oleate, oxalate, palmitate, picrate, pivalate, propionate, pyrophosphate, salicylate, salicylsulfate, sulfosalicylate, sulfosalicylate, tannate, terephthalate, thiosalicylate, tribrophenate, valerate, valproate, adipate, 4-acetamidobenzoate, camsylate, octanoate, estolate, esylate, glycolate, thiocyanate, and undecylenate.

When a metal cation is employed as a counterion of the active agent, the interaction between guest and cation is not a hydrogen bond but rather is an intermolecular interaction between an electron rich group such as a carbonyl and the metal cation. This interaction is often not as strong as a hydrogen bond, but is still a favorable interaction and thus can contribute to the stabilization of a cocrystal.

The HCl salt of an active pharmaceutical ingredient is especially preferred to create a new type of cocrystal. In this type of solid state phase, one can cocrystallize the HCl salt with a neutral guest molecule. By doing this one can create solid state phases with specific properties. For instance one can make a solid comprising an active pharmaceutical ingredient having greater or lesser intrinsic solubility and/or a faster or slower dissolution rate, depending on the guest compound that is chosen.

The present techniques may be utilized in methods for screening an ionizable active agent according to its possible salts or for preparing a salt comprising an ionizable active agent and a guest. Such methods can comprise providing a plurality of samples comprising the active agent and one or more counterions; sonicating the sample(s); and forming crystallized salt compounds comprising the active agent and counterions. The counterions may be any of the cations or anions set forth above or elsewhere in the present disclosure. Using the present techniques provides a greater likelihood of generating possible salts of the ionizable active agent. Moreover, a salt developed by such a method may be employed in connection with the methods described herein which relating to cocrystals comprising a salt and a guest.

Guests

The guest is present in order to form the cocrystal with the active agent. It is contemplated that one or more guests may be employed in a cocrystal, according to any of the present techniques. Accordingly, the guest is not required to have an activity of its own, although it may have some activity that does not overly derogate from the desired activity of the active agent. In some situations, the guest may have the same activity as or an activity complementary to that of the active agent. The guest may be another API. For example, some guests may facilitate the therapeutic effect of an active pharmaceutical ingredient. For pharmaceutical formulations, the guest may be any pharmaceutically acceptable molecule(s) that forms a cocrystal with the API or its salt. The RTECS database is a useful source for toxicology information, and the GRAS list contains about 2500 relevant compounds.

Figure 10:
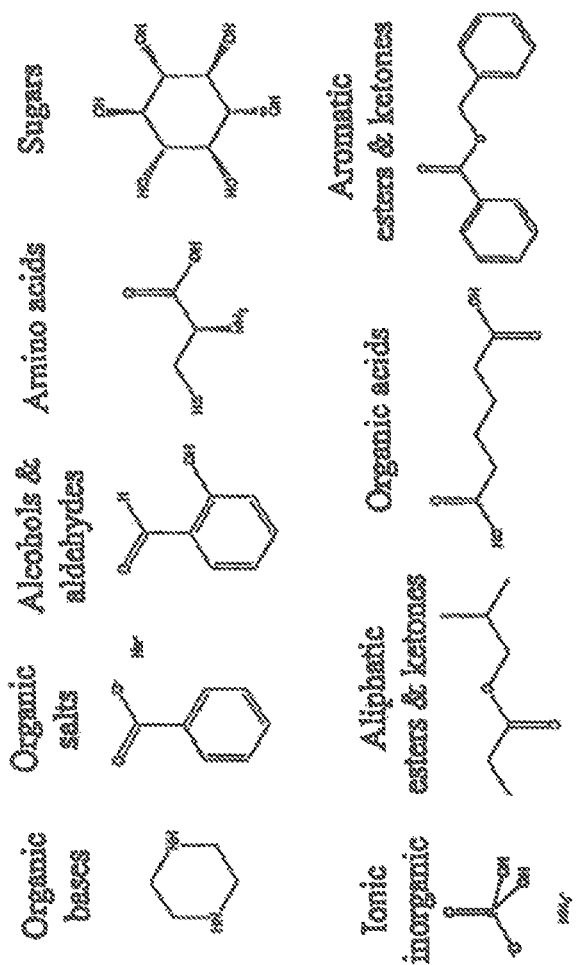
FIG. 10 shows examples of general classes of guests.

The guest may be neutral (such as benzoic acid and succinic acid in the examples below) or ionic (such as sodium benzoate or sodium succinate). Neutral guests are nonionic guests. Ionic guests are compounds or complexes having ionic bonds. FIG. 10 shows several general classes of guests (organic bases, organic salts, alcohols & aldehydes, amino acids, sugars, ionic inorganics, aliphatic esters & ketones, organic acids, and aromatic esters & ketones).

The guest may be an acid that forms hydrogen bonds with the chloride (or other anion). For example, suitable guests which are acids include (but are not limited to):
    ascorbic acid
    glucoheptonic acid
    sebacic acid
    alginic acid
    cyclamic acid
    ethane-1,2-disulfonic acid
    2-hydroxyethanesulfonic acid
    2-oxo-glutaric acid
    naphthalene-1,5-disulfonic acid
    nicotinic acid
    pyroglutamic acid
    4-acetamidobenzoic acid Table 8 sets forth a group of presently preferred guests. It is contemplated that the guests set forth in the Table may be arranged in subgroups based upon molecular structure and/or physiological effect. Furthermore, the foregoing list is intended to prov±de a written description of any sublist that omits one or more guests.

Table 9 sets forth another group of preferred guests. It is contemplated that the guests set forth in the Table may be arranged in subgroups based upon molecular structure and/or physiological effect. Furthermore, the foregoing list is intended to prov±de a written description of any sublist that omits one or more guests.

Table 10 sets forth the group comprising molecules believed at present to be suitable guests. It is contemplated that the guests set forth in the Table may be arranged in subgroups based upon molecular structure and/or physiological effect. Furthermore, the foregoing list is intended to provide a written description of any sublist that omits one or more guests.

Ionic guests are salts themselves, and may be formed from bases and acids prior to being used to form cocrystals. For example, the following bases and acids may be reacted to form ionic guests:

Bases
    Ammonia
    L-Arginine
    Benethamine
    Benzathine
    Betaine
    Calcium Hydroxide
    Choline
    Deanol
    Diethanolamine
    Diethylamine
    2-(Diethylamino)ethanol
    2-Aminoethanol
    Ethylenediamine
    N-Methylglucamine
    Hydrabamine
    1H-Imidazole
    Lysine
    Magnesium Hydroxide Morpholine
4-(2-Hydroxyethyl)Morpholine
Piperazine
Potassium Hydroxide
Pyrrolidine
1-(2-Hydroxyethyl)Pyrrolidine
Sodium Hydroxide
Triethanolamine
Tromethamine
Zinc Hydroxide Acids
(+)-L-Tartaric Acid
1,2,2-Trimethyl-1,3-cyclopentanedicarboxylic Acid
10-Undecylenic Acid
1-Hydroxy-2-naphthoic Acid
(+)-Camphor-10-sulfonic Acid
2,5-Dihydroxybenzoic Acid
2-Furancarboxylic Acid
2-Mercaptobenzoic Acid
3-Cyclopentylpropionic Acid
3-Phenylpropionic Acid
4-Aminosalicylic Acid
4-Hydroxybenzoic Acid
Acetic Acid
Adipic Acid
alpha-Hydroxypropionic Acid
Benzenesulfonic Acid
Benzoic Acid
Carbonic Acid
Cholic Acid
Citric Acid
(−)-D-Tartaric Acid
(+)-D-Camphoric Acid
(+)-D-Malic Acid
(+)-L-Malic Acid
2,2-Dichloroacetic Acid
DL-10-Camphor sulfonic Acid
DL-Glutamic Acid
DL-Mac Acid
DL-Tartaric Acid
Dodecylsulfuric Acid
Ethanesulfuric Acid
Ethylenediaminetetraacetic Acid
Ethylsulfuric Acid
Fumaric Acid
Galactaric Acid
Gallic Acid
Gluconic Acid
Glutaric Acid
Glycolic Acid
Hippuric Acid
Hydriodic Acid
Hydrobromic Acid
Hydrochloric Acid
(−)-L-Apple Acid
(+)-L-Lactic Acid
(+)-L-Tartaric Acid
D,L-Lactic Acid
Lactobionic Acid
L-Aspartic Acid
Lauric Acid
L-Glutamic Acid
Maleic Acid
(−)-L-Malic Acid
Malonic Acid
D,L-Mandelic Acid
Methanesulfonic Acid
Naphthalene-2-sulfonic acid
n-Butyric Acid
n-Decanoic Acid
n-Hexanoic Acid
Nitric acid
n-Tetradecanoic Acid
Octanoic Acid
Oleic Acid
Orotic Acid
Orthoboric Acid
Oxalic Acid
4-Acetamidobenzoic Acid
Palmitic Acid
Pamoic Acid
Phosphoric Acid
Picric Acid
Pivalic Acid
Propionic Acid
p-Toluenesulfonic Acid
Pyrophosphoric Acid
Salicylic Acid
Stearic Acid
Succinic Acid
Sulfosalicylic Acid
Sulfuric Acid
Terephthalic Acid
Thiocyanic Acid
Valeric Acid
Valproic Acid Typically, suitable guests will have complementary ability to noncovalently bond to the active agent or its salt, for example the ability to form hydrogen bonds with the active agent or its salt. Suitable guests for active agents having negative counterions include, but are not limited to, compounds having alcohol, ketone, ester, and/or carboxylic acid functionalities. Suitable guests may include organic acids, organic bases, organic salts, alcohols, aldehydes, amino acids, sugars, ionic inorganic compounds, aliphatic esters and ketones, and aromatic esters and ketones.

Among the presently preferred neutral guests are those which are not liquids at room temperature. Also among the presently preferred neutral guests are carboxylic acids having at least three carbon atoms, alternatively at least four carbon atoms, and which do not form solvates. For example, if the following acids were combined with active agents, the combination would more properly be considered a solvate than a cocrystal: acetic acid, propionic acid, and butyric acid. However, in certain embodiments of the present invention (for example, in certain cocrystals, cocrystallization methods, and screening methods), the use of solvents and solvates may still be desirable, and the use of solvents and solvates is not excluded from the scope of any cocrystal or method except where explicitly stated.

In the present methods, the active agent(s) and guest(s) to be cocrystallized are provided as one or more samples to be used within the present techniques. The samples may be provided by being formed, created or prepared as an initial step in the present methods, or they may be obtained ready-to-use from another source.

In some embodiments, the samples may contain the active agent(s) and the guest(s) alone, for example, in a melt or a physical mixture. Alternatively, the sample will also contain a solvent(s) in which the active agent(s) and the guest(s) are dissolved, dispersed or otherwise disposed. The active agent(s) and the guest(s) may be completely or partially soluble in the solvent(s) or one or more of them may be substantially insoluble in the solvents. Accordingly, the sample may be in a solution, dispersion, suspension, mixture, slurry or emulsion, or other physical state. The sample's physical state going into the present methods is not critical to the broader applicability of the present methods, though in some embodiments, use of particular physical states for samples can be beneficial, as described in more detail herein. For example, the present methods may have additional benefits when the samples are metastable solutions, viscous solutions, emulsions or slurries.

Cocrystallization

In the present methods, the active agent and the guest are cocrystallized from the sample using a suitable crystallization technique. As used herein, crystallization includes any suitable technique for preparing a crystal from the sample.

The crystallization technique(s) employed will depend in part on the sample(s). Suitable crystallization techniques include cooling, heating, evaporation, addition of an antisolvent, reactive crystallization, and using supercritical fluids as solvents. A fluid is an antisolvent with respect to a given solution of components to be cocrystallized when at least one component is less soluble in that fluid than in the solvent used to form the solution; preferably, an antisolvent is a fluid in which both components are essentially insoluble or have a low solubility. Reactive crystallization refers to processes where a chemical compound is formed from reactants and crystallized substantially simultaneously, for example, where the reaction is a driving force toward crystallization. A supercritical fluid is a fluid above its critical temperature and critical pressure which combines properties of gases and liquids. Examples of compounds employed as supercritical fluids include xenon, ethane and carbon dioxide.

Alternatively, the mechanism by which crystallization is accomplished may include gel diffusion methods, thin-layer deposition methods, or other suitable methods. Other thermodynamic and kinetic conditions may be employed for cocrystallization. Slow cooling of a saturated solution is a typical thermodynamic condition. An addition of a solution of the components to be cocrystallized to an excess of cold antisolvent is a typical kinetic condition.

Additionally, melt crystallization techniques may be used to generate a cocrystal. Through such techniques, the use of a solvent can be avoided. In such techniques, formation of crystalline material is from a melt of the crystallizing components rather than a solution. Additionally, the crystallization process may be done through sublimation techniques.

In many embodiments, the samples will comprise a solvent. Any suitable solvent can be used. Suitable solvents include acetone, acetonitrile, chloroform, 1,4-dioxane, ethanol, ethyl acetate, heptane, 2-butanone, methanol, nitromethane, tetrahydrofuran, toluene, water, dichloromethane, diethyl ether, isopropyl ether, cyclohexane, methylcyclohexane, isopropyl alcohol, trimethylpentane, n-octane, trichloroethane, trifluoroethanol, pyridine, 1-butanol, tetrachloroethylene, chlorobenzene, xylene, dibutyl ether, tetrachloroethane, p-cymene, dimethyl sulfoxide, formamide, and dimethylformamide. It is also contemplated that the samples may comprise the components to be cocrystallized in two or more solvents, either as a homogeneous solution, as an emulsion, or in another physical state.

The crystallization may be accomplished in a variety of ways, and preferably includes evaporation of the solvent(s). For example, the solvent may be evaporated either slowly (for example, evaporating to dryness over a time period of four days, alternatively two days or more) or quickly (for example, evaporating to dryness over a time period of 24 hours, alternatively under two days). By varying the rate of evaporation among separate samples, one can introduce desired variability into a screening method. For example, in a screening method, a first portion of samples can be subjected to relatively slow evaporation, and a second portion of the samples can be subjected to relatively fast evaporation.

In the present methods, ultrasound may be applied at different stages of a screening process or a crystallization process. For example, a solution which comprises the components to be cocrystallized can be sonicated at some point during the screening process. One may sonicate such a solution before, during, or after the initiation of cooling of the solution from an undersaturated, saturated, or supersaturated state. As other examples, one may sonicate a solution before, during, or after the beginning of evaporation of solvent, or before, during, or after the addition of an immiscible antisolvent to the solution.

In the present methods, the crystallizing step and the sonicating step can overlap. For example, where the samples are provided as a solution of the components to be cocrystallized in a solvent, the crystallizing step may be performed by evaporating the solvent, and the sample may be sonicated during that evaporation. Furthermore, the sonication can be periodic during the evaporation. For example, the sample can be periodically sonicated for about 20 seconds, and the periods can be about 30 minutes (in other words, the sample is sonicated for about 20 seconds every 30 minutes). Furthermore, the sonication can be a single pulse. For example, the sonication could be carried out one time for 5 to 40 seconds or multiple times for a liked period, or for other suitable period(s).

In the present methods, the samples can comprise a solution, suspension (such as a melt), or other mixture of the components to be cocrystallized. The sample will typically be prepared by heating above room temperature to achieve supersaturation of the components. It may be desirable to begin cooling the samples (for example, to room temperature) before the sonicating step. Alternatively, the samples may be cooled and sonicated at the same time. Alternatively, the method can include crash-cooling the samples (rapidly lowering the temperature, for example, by immersing in an ice bath) before the sonicating step. Alternatively, the samples may be crash-cooled and sonicated at the same time.

The present methods can include the step of adding a second solvent to a solution containing the components to be cocrystallized. For example, the second solvent may be added to facilitate crystallization.

The crystallization step can be initiated by sonication, and it may additionally be initiated by seed materials or other techniques. In the various embodiments of the present methods, crystallization may start before, during, or after the application of ultrasound. In many cases, the crystallization and sonication steps will overlap. For example, sonication may begin before crystallization but continue even after crystallization begins. As another example, crystallization may begin before sonication. As yet another example, the samples may be sonicated in a pulsing manner throughout the crystallization process. Alternatively, sonication may be employed to initiate crystallization and be discontinued when crystallization (such as nucleation) begins.

The sample containing two or more components to be cocrystallized is provided in a receptacle suitable for crystallization, such as a vial, well-plate or capillary tube. The sample may be formed in the receptacle or formed outside the receptacle and then placed in it. The components can initially be present in the sample below, at or above the point of saturation at a given temperature at the time of placement in the receptacle. Through evaporation, the use of an antisolvent, temperature variation, and/or other suitable means, the sample will reach a point where crystallization begins. After a suitable amount of time, when a solid or semisolid appears, the resulting sample (more particularly, the solid formed from the sample) is ready for analysis.

Crystallization may be performed as a seeded operation or an unseeded operation. In a seeded operation, a selected quantity of seed crystals is included in the system. The characteristics of the seed crystals typically influence the characteristics of the crystals generated from the system. Crystallization may be performed by heterogeneous or homogeneous mechanisms. However, it is noted that ultrasound may be applied as a way of omitting the presence of seed crystals.

Another technique for cocrystallizing chemical substances employs an emulsion. An emulsion is a mixture of two or more immiscible liquids where one liquid is in a discontinuous phase within the other liquid. Emulsions are frequently formed and/or stabilized by the use of agents called emulsifiers. However, sonication of an immiscible mixture of solvents also allows the generation of emulsions.

The present methods may also include the step of forming an emulsion comprising two or more substantially immiscible solvents and the components to be cocrystallized. The emulsion can be formed during the sonicating step, wherein an immiscible mixture of said solvents is sonicated to form the emulsion. Alternatively, the emulsion can be formed before the sonicating step.

Emulsions can be employed as part of a screening method and/or solidification method to generate additional solid state phases of an active agent. Emulsions can allow interface between the two solvents over a high surface area. At such interfaces, nucleation and/or growth of some solid state phases may be favored, based on the influence of each solvent on the growth of each solid state phase.

An emulsion may be prepared by combining a solution of an active agent and a guest in a first solvent with a second solvent, wherein the first solvent and the second solvent are substantially immiscible with each other. The combined solvents may then be sonicated while evaporating cooling, adding and antisolvent, or using other solidification techniques until a precipitate containing the active agent and the guest appears.

Another technique for cocrystallizing employs a slurry. A slurry is a dispersion of solid particles in a liquid phase. The liquid pHiase comprises one or more solvents in which at least one of the active agent and a guest is not completely soluble. The process of slurrying a metastable form of an active agent and/or guest, aiming at finding a cocrystal or a solvated form, is foreseen to be accelerated by the use of ultrasound during the slurrying process.

The present methods may also include the step of forming a slurry comprising a solvent and the active agent and the guest. The slurry can be formed during the sonicating step, wherein a mixture of the active agent and the guest and the solvent are sonicated to form the slurry. Alternatively, the slurry can be formed before the sonicating step.

Generating a variety of solid state phases is an important object of screening. A sufficient number of diverse processes and parameters should be employed to maximize the likelihood that a high percentage of possible solid state phases is generated. Samples should be generated under various thermodynamic and kinetic conditions.

It is preferable that the generation, of solid state phases is carried out under a wide variety of conditions. For example, solids should be generated in the presence and absence of various solvents, as the solvent may play a role in the formation of certain forms, and with and without sonication. As another example it is also preferable to prepare solid forms under different conditions of temperature and pressure, as different solid forms may be favored by different conditions.

It is also contemplated that the present methods are advantageous for generating solid state phases from viscous solutions. For example, the present methods may be used with samples that are solutions having a viscosity greater than about 0.9 poise before the solution is sonicated.

It is also contemplated that the present methods are advantageous for generating solid state phases from amorphous forms of the active agent. Samples can be formed or provided by preparing a solution from a solvent and an amorphous solid comprising the active agent. The solvent may be sonicated while the amorphous solid is added to the solvent.

It is contemplated that, in the context of a comprehensive screening method, a plurality of samples can be divided into a large number of sets and subsets. A multiplicity of sets and subsets are useful so that more than one parameter may be varied and the cumulative effect of multiple varied parameters may be assessed. For example, a plurality of samples may be divided into a first set, a second set, a third set, and a fourth set. The first set and the second set can comprise a solution of the active agent in a first solvent or with a first guest, while the third set and the fourth set comprise a solution of the active agent in a second solvent or with a second guest. The first set and the third set can be sonicated, and the second set and the fourth set can be unsonicated. The benefit of this method is that the effects of ultrasonic crystallization with different solvents and/or different guests can be analyzed and compared.

Detection of Cocrystals and Crystals

Cocrystals (as well as other crystals) may be detected by x-ray diffraction analysis, Raman analysis, or other suitable techniques. The observation of physical properties of a solid (particularly its melting point) which differ from the physical properties of the starting materials and the polymorphs and/or solvates and/or hydrates of the starting materials, is an indicator that a cocrystal has been formed.

Cocrystals and other crystals generated after crystallization and sonication steps may be identified by any suitable method, including but not limited to visual analysis (such as when different forms exhibit different colors), microscopic analysis including electron microscopy (such as when different forms happen to have different morphologies), thermal analysis (such as determining the melting points), conducting diffraction analysis (such as x-ray diffraction analysis, electron diffraction analysis, neutron diffraction analysis, as well as others), conducting Raman or infrared spectroscopic analysis, or conducting other spectroscopic analysis. Any appropriate analytical technique that is used to differentiate structural, energetic, or performance characteristics may be used in connection with the present methods.

In a preferred embodiment, the samples are placed in a well plate and then sonicated. The chemical substances solidify in the wells of the well plate (for example, a 96-well plate or 384-well plate). The solidified chemical substances are then analyzed in the well plate by one of the foregoing analysis techniques, preferably by x-ray diffraction (such as transmission x-ray diffraction) and/or by Raman spectroscopy. A synchrotron may be used as the source of radiation for conducting diffraction analyses.

Synchrotron radiation may be used to study structural details of solid samples with a resolution not practically attainable using traditional x-ray instrumentation. This may enable differentiation between different solid state phases that is not attainable with other x-ray radiation sources.

The present methods can significantly assist in the identification of the possible cocrystals of a chemical substance(s). For example, the present methods can be used as part of a screening method and can improve the likelihood of identifying a solid state phase having properties such as better stability, bioavailability, solubility, or absorption characteristics. In some cases, an identified cocrystal of an active agent and a guest may have better biological activity than a crystal of the active agent.

After samples (including a solution, emulsion, slurry, or mixture containing the active agent and guest) are placed in a receptacle, the receptacle may be centrifuged. Centrifugation may be employed for a variety of reasons. First, use of a centrifugal evaporator may assist evaporation while concentrating solid or semisolid material at one end of a capillary space. This has advantages in connection with in-situ analysis, in that the generated form will be located at a consistent place in the receptacle. Also or alternatively, centrifuging may be used to provide additional environmental variation, which is desirable in a screening method.

EXAMPLE 1

In this Example, a new solid form of sulfathiazole was prepared from solution in acetonitrile using sonication. This form was not seen without sonication under the same conditions. Form II of sulfathiazole was generated without sonication.

Figure 2:
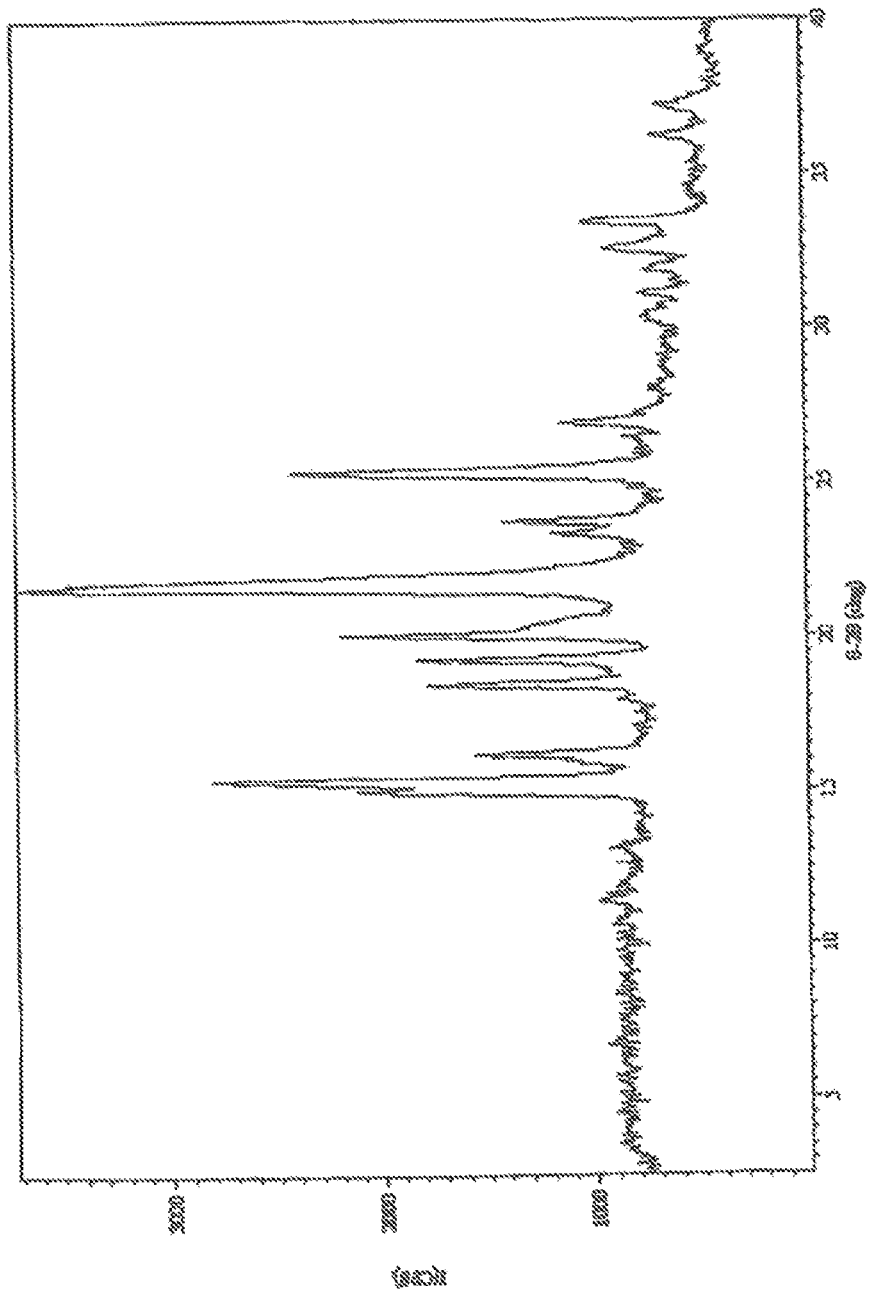
FIG. 2 is an XRPD pattern of sulfathiazole solidified from an acetonitrile solution which was not sonicated.

A saturated solution of sulfathiazole in acetonitrile at 45° C. was prepared, filtered hot and split between two pre-heated 1-dram vials (about 1 ml each). The samples were left to slowly cool to room temperature. One sample was then nucleated by ultrasound treatment using 5 pulses of one second each at 20 kHz, amplitude control set at 40, using a Cole Palmer ultrasonic processor CP130 fitted with a 6 mm tip stainless steel probe, while the other sample was left undisturbed (unsonicated). Both samples were then left to evaporate slowly to dryness. XRPD patterns of the sonicated and unsonicated samples showed that the sonicated sample gave an unknown pattern (FIG. 1) whereas the unsonicated sample yielded the known Form II of sulfathiazole (FIG. 2). The sonicated sample is believed to be a novel solid form of sulfathiazole.

EXAMPLE 2

In this Example, an unusual solid form of an acetone solvate of sulfathiazole was prepared. Without sonication, this form was only seen in a mixture with the known form of an acetone solvate of sulfathiazole.

Figure 3:
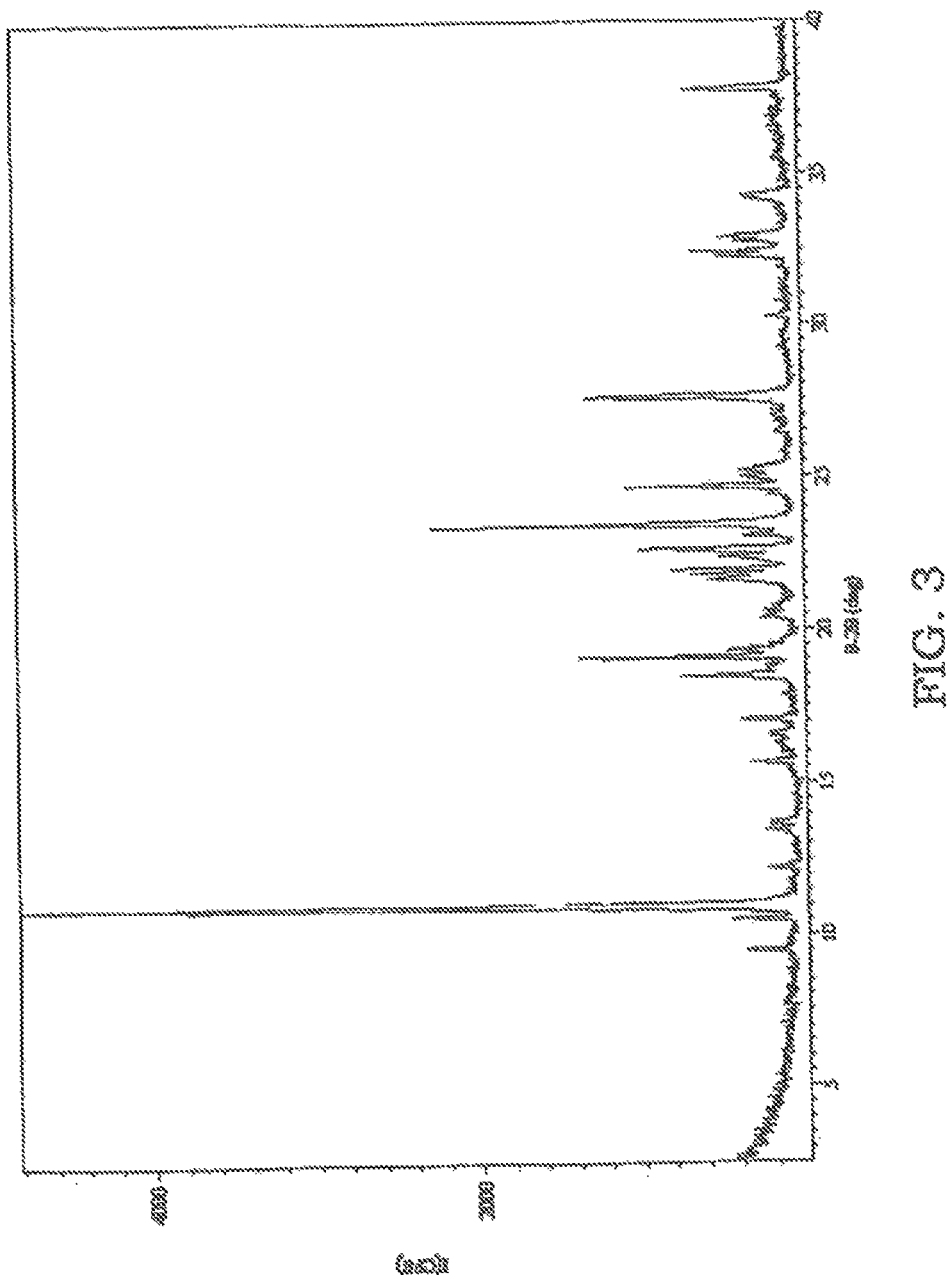
FIG. 3 is an XRPD pattern of sulfathiazole solidified from an acetone solution which was sonicated.
Figure 4:
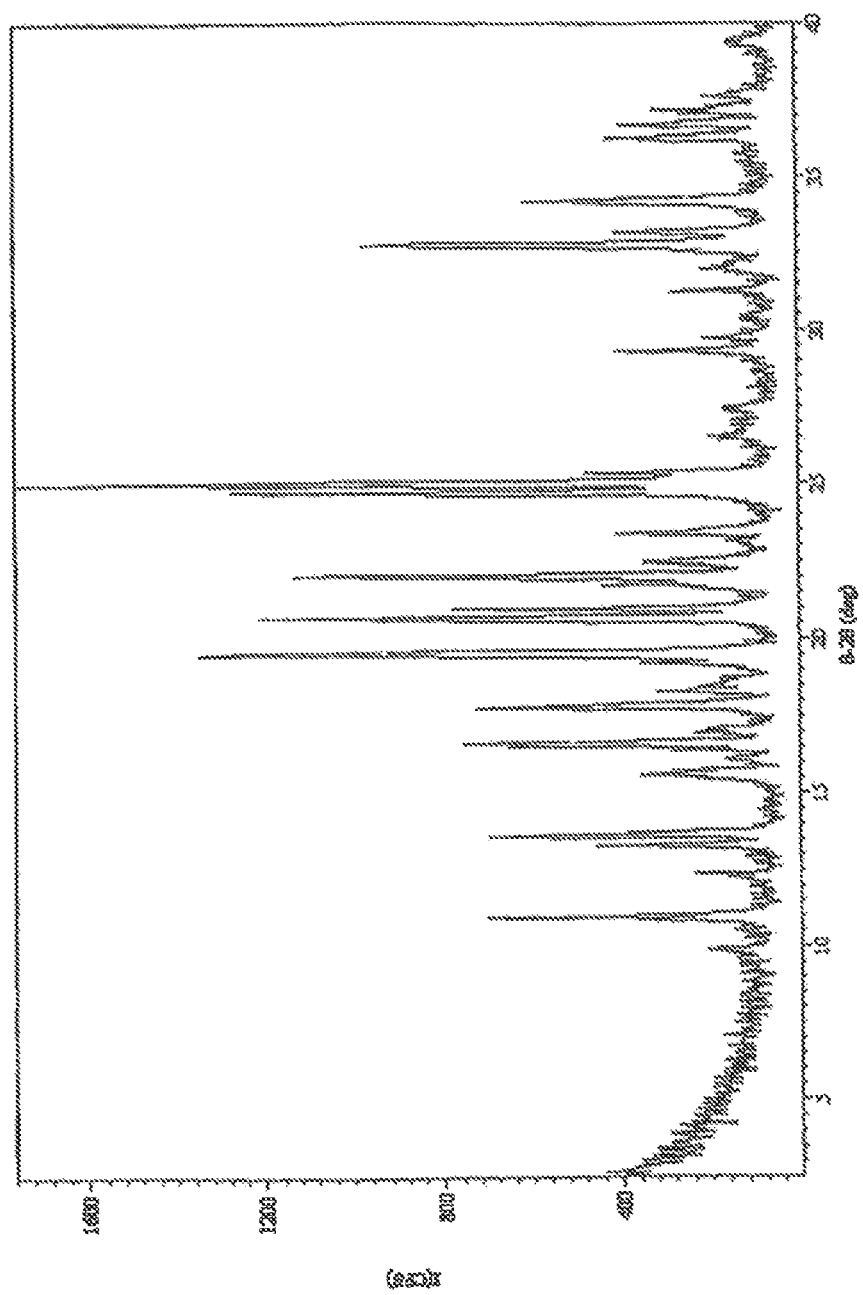
FIG. 4 is an XRPD pattern of sulfathiazole solidified from an acetone solution which was not sonicated.

A saturated solution of sulfathiazole in acetone at 45° C. was prepared, filtered hot and split between two pre-heated 1-dram vials (about 1 ml each). The samples were left to slowly cool to room temperature. One sample was then nucleated by ultrasound treatment using 5 pulses of one second each at 20 kHz, amplitude control set at 40, using a Cole Palmer ultrasonic processor CP130 fitted with a 6 mm tip stainless steel probe, while the other sample was left undisturbed (unsonicated). Both samples were then left to evaporate slowly to dryness. XRPD patterns of the sonicated and unsonicated patterns showed that the sonicated sample gave an unknown pattern (FIG. 3) whereas the unsonicated sample yielded a mixture of this same form with the known acetone solvate of sulfathiazole (FIG. 4). The sonicated sample is believed to contain an unusual solid form which is novel in its purity.

EXAMPLE 3

In this Example, a new DMSO solvate of carbamazepine was prepared.

Figure 5:
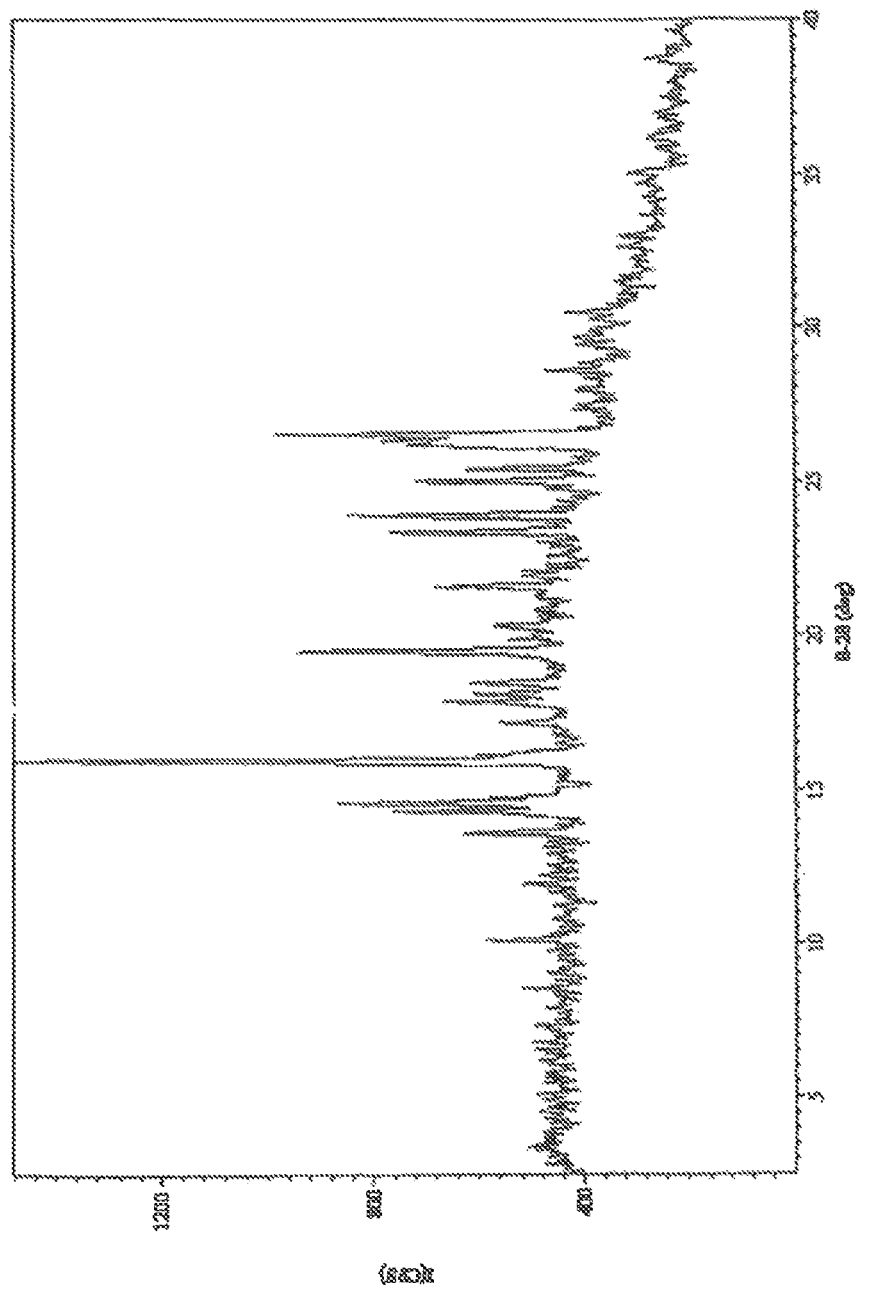
FIG. 5 is an XRPD pattern of carbamazepine solidified from a DMSO solution which was sonicated.

Three 100 µl samples of a saturated solution of carbamazepine in DMSO at 50° C. were placed in 3 pre-heated HPLC vials. The samples were allowed to cool to ambient temperature. One sample was nucleated by ultrasound treatment (5 one-second pulses, 20 kHz, amplitude control set at 40, using the Cole Palmer ultrasonic processor with a 3 mm tip stainless steel probe), while another was stirred using a stir bar and the other was left undisturbed (unsonicated). While the sonicated sample yielded a new DMSO solvate, the other samples remained as solutions indefinitely. The XRPD pattern of the new DMSO solvate is shown in FIG. 5.

EXAMPLE 4

In this Example, a new form of sulfathiazole was made from a sonicated supersaturated solution in methylethylketone.

Figure 6:
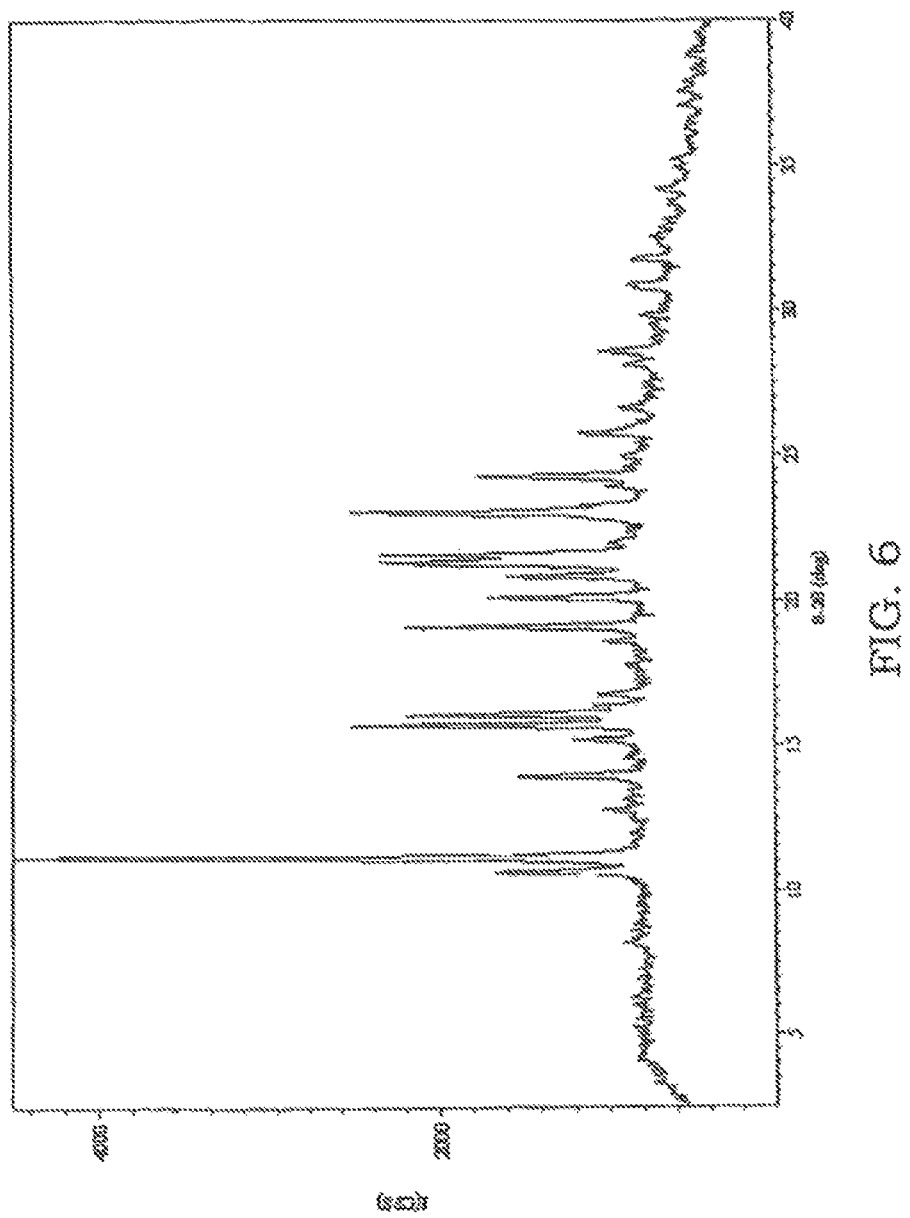
FIG. 6 is an XRPD pattern of sulfathiazole solidified from a methylethylketone solution which was sonicated.

A saturated solution of sulfathiazole in methylethylketone at 55° C. was split in 3 pre-heated vials (about 0.5-1 ml each). The samples were crash-cooled by placing them in an ice/water bath. One sample was then sonicated for five minutes (amplitude 20 kHz, amplitude control set at 40, using the Cole Palmer ultrasonic processor with a 6 mm probe), while another was stirred using a magnetic stir bar. The last sample was left undisturbed. The three samples were then placed in the refrigerator (5-6° C.). While the sonicated sample was found to have crystallized, the unsonicated samples remained indefinitely as solutions (still solutions after three weeks). The solids in the sonicated sample were filtered and an XRPD pattern taken (FIG. 6), indicative of an unknown form, and it was determined that this solid was unsolvated according to TGA and DSC scans.

EXAMPLE 5

In this Example, crystallization of the most stable form of 4-methyl-2-nitroacetanilide was performed on a small scale. The compound 4-methyl-2-nitroacetanilide is known to crystallize in three polymorphic forms, White, Amber, or Yellow. The compound is known as "WAY" due to the colors of its forms. The relative stability of the three forms has been studied and it was demonstrated that the white form was the most stable form, and the yellow form was more stable than the amber form. (See, for example, Yeadon, PhD thesis, Burnel University, West Yorkshire, UK (1985), and Xiaorong He, "Thermodynamic and kinetic control of the crystallization of polymorphs", PhD thesis, Purdue University, West Lafayette, Ind. USA (2000)). The least stable amber form has rarely been seen. All three crystal structures have been solved and published. (See, for example, Moore et al., "Yellow and white forms", J. Cryst. Spect. Res., 13, 279 (1983), and Moore et al., "Amber form", J. Cryst. Spect. Res., 14, 283 (1984).

Sixty-four evaporative experiments in various solvents and combinations of solvents (32 sonicated samples and 32 unsonicated samples) were carried out on the compound WAY.

A weighed amount of the compound WAY was placed in a vial and a measured volume (V) of solvent added (solvent 1), so as to dissolve the solids. In some samples, an additional volume of a second solvent (solvent 2) was added to the solution. All solutions were filtered using a 0.2 µm nylon filter and split 4-ways into 4 1-dram vials. The vials were then covered individually with aluminum foil. The aluminum foil was pierced with one hole for slow evaporations (SE) and 5 holes for fast evaporations (FE). Half of the vials were then sonicated twice a day, every day, until complete evaporation of the solvents. The other half of the vials were left to evaporate undisturbed. Table 1 summarizes the solvent conditions used for these evaporations, each set of solvent conditions being used for four vials (two for samples to be sonicated while evaporating (SE and FE), two for control experiments without sonication (SE and FE)).

TABLE 1

Solutions used for crystallization of 4-methyl-2-nitroacetanilide

| WAY (mg) | Solvent 1 | V (S1) | Solvent 2 | V (S2) |
|---|---|---|---|---|
| 146.3 | 1,4-dioxane | 3 ml | — | — |
| 149.8 | acetone | 3 ml | — | — |
| 155.2 | tetrahydrofuran | 3 ml | — | — |
| 149.9 | ethanol | 10 ml | — | — |
| 147.7 | 2-butanone | 3 ml | — | — |
| 155.6 | dichoromethane | 1 ml | — | — |
| 146.2 | chloroform | 1 ml | — | — |
| 155.0 | trifluroethanol | 1 ml | — | — |
| 151.0 | ethyl acetate | 3 ml | — | — |
| 148.9 | dichloroethane | 1 ml | — | — |
| 149.1 | pyridine | 1 ml | — | — |
| 156.5 | methanol | 5 ml | — | — |
| 150.2 | acetonitrile | 2 ml | — | — |
| 144.9 | dichloromethane | 2 ml | nitromethane | 2 ml |
| 155.5 | dichloromethane | 2 ml | heptane | 2 ml |
| 146.7 | trifluoroethanol | 2 ml | water | 2 ml |
| 154.3 | acetone | 3 ml | toluene | 1 ml |
| 146.4 | acetone | 3 ml | water | 1 ml |

The results are presented in Table 2, showing the occurrences of mixtures of the white and yellow solid forms and of the most stable solid form of the compound, the white form of WAY. All other solids were the faster growing, less stable yellow form. These results show that using ultrasound as part of a screening process can increase the likelihood of obtaining the possible solid forms of a chemical substance. These results also show that using ultrasound in a crystallization process can facilitate the generation of the most stable form of the chemical substance.

TABLE 2

|  | Sonicated | Sonicated | Unsonicated | Unsonicated |
|---|---|---|---|---|
| Evaporative conditions | SE | FE | SE | FE |
| # of samples | 16 | 16 | 16 | 16 |

TABLE 2-continued

|  | Sonicated | Sonicated | Unsonicated | Unsonicated |
|---|---|---|---|---|
| Solids | 16 | 16 | 14 | 16 |
| White + yellow mixture | 5 | 3 | 1 | 1 |
| Pure White Form | 4 | 2 | 0 | 1 |

EXAMPLE 6

In this Example, a micro-scale crystallization study was performed to yield the most stable form of 4-methyl-2-nitroacetanilide (WAY).

Solutions of WAY were prepared in various solvents by dissolution of a weighed amount of the solid compound in a measured volume of solvent (solvent 1). These solutions were then filtered using a 0.2 μm nylon filter. The weights and volumes used to prepare each solutions are summarized in Table 3.

TABLE 3

Summary Table Of Experimental Conditions For The Preparation Of Solutions Of Way

| WAY (mg) | Solvent | V (ml) |
|---|---|---|
| 103.2 | chloroform | 5.16 |
| 107.7 | 1,4-dioxane | 5.37 |
| 101.9 | acetone | 5.1 |
| 100.8 | tetrahydrofuran | 5.04 |
| 112.7 | ethanol | 11.3 |
| 105.7 | 2-butanone | 5.27 |
| 108.6 | acetonitrile | 5.43 |
| 94.0 | methanol | 4.7 |

Each solution was then used directly or was diluted with a second solvent in a 3:1 ratio of the first solvent to the second solvent. Aliquots of 200 μl of the solutions were placed in wells of a flat bottom polypropylene 96-well plate and covered by a polypropylene mat. The mat was pierced to provide one hole per well. Two identical plates were prepared. The solvent(s) used in each of the wells are shown in Table 4. One plate was sonicated for 20 seconds every 30 minutes until evaporation to dryness of all or the majority of the samples in each well. Sonication was performed using a Misonix 3000 sonicator with microplate horn. The second plate was kept undisturbed (unsonicated) during the time of the evaporation.

TABLE 4

Solvent Conditions Used For Individual Wells Of The 96-Well Plate Evaporation Experiment

|  | 1 | 2 | 3 | 4 | 5 | 6 | 7 | 8 | 9 | 10 | 11 | 12 |
|---|---|---|---|---|---|---|---|---|---|---|---|---|
| A | CH | CH | CH:WA 3:1 | CH:WA 3:1 | CH:NM 3:1 | CH:NM 3:1 | CH:TO 3:1 | CH:TO 3:1 | CH:EA 3:1 | CH:EA 3:1 | CH:HE 3:1 | CH:HE 3: |
| B | DX | DX | DX:WA 3:1 | DX:WA 3:1 | DX:NM 3:1 | DX:NM 3:1 | DX:TO 3:1 | DX:TO 3:1 | DX:EA 3:1 | DX:EA 3:1 | DX:HE 3:1 | DX:HE 3: |
| C | AC | AC | AC:WA 3:1 | AC:WA 3:1 | AC:NM 3:1 | AC:NM 3:1 | AC:TO 3:1 | AC:TO 3:1 | AC:EA 3:1 | AC:EA 3:1 | AC:HE 3:1 | AC:HE 3:1 |
| D | TH | TH | TH:WA 3:1 | TH:WA 3:1 | TH:NM 3:1 | TH:NM 3:1 | TH:TO 3:1 | TH:TO 3:1 | TH:EA 3:1 | TH:EA 3:1 | TH:HE 3:1 | TH:HE 3:1 |
| E | EO | EO | EO:WA 3:1 | EO:WA 3:1 | EO:NM 3:1 | EO:NM 3:1 | EO:TO 3:1 | EO:TO 3:1 | EO:EA 3:1 | EO:EA 3:1 | EO:HE 3:1 | EO:HE 3:1 |
| F | MK | MK | MK:WA 3:1 | MK:WA 3:1 | MK:NM 3:1 | MK:NM 3:1 | MK:TO 3:1 | MK:TO 3:1 | MK:EA 3:1 | MK:EA 3:1 | MK:HE 3:1 | MK:HE 3:1 |
| G | AN | AN | AN:WA 3:1 | AN:WA 3:1 | AN:NM 3:1 | AN:NM 3:1 | AN:TO 3:1 | AN:TO 3:1 | AN:EA 3:1 | AN:EA 3:1 | AN:HE 3:1 | AN:HE 3:1 |

TABLE 4-continued

Solvent Conditions Used For Individual Wells Of The 96-Well Plate Evaporation Experiment

| | 1 | 2 | 3 | 4 | 5 | 6 | 7 | 8 | 9 | 10 | 11 | 12 |
|---|---|---|---|---|---|---|---|---|---|---|---|---|
| H | MO | MO | MO:WA 3:1 | MO:WA 3:1 | MO:NM 3:1 | MO:NM 3:1 | MO:TO 3:1 | MO:TO 3:1 | MO:EA 3:1 | MO:EA 3:1 | MO:HE 3:1 | MO:HE 3:1 | in Table 4, the solvent mixtures are described as X:Y volume:volume ratio of solvents. In Table 4, the following abbreviations are used: AC=acetone; AN=acetonitrile; CH=chloroform; DX=1,4-dioxane; EO=ethanol; EA=ethyl acetate; HE=heptane; MK=2-butanone; MO=methanol; NI=nitromethane; TH=tetrahydrofuran; TO=toluene; WA=water.

TABLE 5

Summary Table Of Results Obtained For The Sonicated Plate

| | 1 | 2 | 3 | 4 | 5 | 6 | 7 | 8 | 9 | 10 | 11 | 12 |
|---|---|---|---|---|---|---|---|---|---|---|---|---|
| A | Y | W | Y | Y | Y | Y | Y | Y | Y | Y | Y | Y |
| B | NC | NC | N | N | NC | NC | NC | NC | NC | NC | NC | NC |
| C | W | W | Y | Y | NC | W | W | W | Y | Y | W | W |
| D | W | W | W | W | Y | Y | W | W | W | W | W | Y |
| E | NC | NC | NC | NC | NC | Y | NC | Y | NC | NC | NC | NC |
| F | W | NC | W | NC | W | W | W | Y | W | Y | W | W |
| G | Y | W | W | NC | NC | W | W | NC | W | NC | Y | Y |
| H | W | W | W | W | W | Y | W | W | NC | W | Y | Y |

Table 5 shows which solid form of WAY was generated in each of the wells of the 96-well plate that was sonicated.

In Table 5, the following abbreviations are used: Y=Yellow form; W=White form; N=Nucleated=mostly liquid with a small fraction of indeterminate solids; NC=Not Crystallized.

TABLE 6

Summary Table Of Results Obtained For The Unsonicated Plate

| | 1 | 2 | 3 | 4 | 5 | 6 | 7 | 8 | 9 | 10 | 11 | 12 |
|---|---|---|---|---|---|---|---|---|---|---|---|---|
| A | Y | Y | Y | Y | Y | Y | Y | Y | Y | Y | W | Y |
| B | NC | NC | N | N | NC | NC | NC | NC | NC | NC | NC | NC |
| C | Y | Y | Y | Y | Y | NC | Y | Y | Y | Y | Y | Y |
| D | Y | Y | Y | Y | Y | Y | Y | Y | Y | Y | Y | Y |
| E | NC | NC | NC | NC | NC | NC | Y | Y | NC | Y | NC | NC |
| F | Y | Y | Y | Y | NC | NC | NC | NC | Y | Y | Y | NC |
| G | Y | Y | Y | Y | NC | Y | Y | Y | Y | Y | Y | Y |
| H | Y | Y | Y | Y | Y | Y | Y | Y | NC | Y | Y | Y |

Table 6 shows which solid form of WAY was generated in each of the wells of the 96-well plate that was not sonicated.

In Table 6, the following abbreviations are used: Y=Yellow form; W=White form; N=Nucleated=mostly liquid with a small fraction of indeterminate solids; NC=Not Crystallized.

This shows that a screening process in which samples are sonicated yielded more occurrences of the most stable (but less-frequently generated) white form.

EXAMPLE 7

In this Example, a micro-scale crystallization study of sulfamerazine was performed. The study showed that sonication facilitated the generation of a difficult-to-make more stable form.

Sulfamerazine is known to crystallize in two polymorphic forms, Form I and Form II, with Form I being the most commonly encountered form. Despite the elusive character of Form II, it has been demonstrated that Form II was the most stable form at room temperature. Zhang et al., J. Phare. Sci., 91(4), 1089-1100 (2002).

Solutions of sulfamerazine at a concentration of 10 mg/ml were prepared in acetone and in tetrahydrofuran by dissolution of a weighed amount of sulfamerazine in a measured volume of solvent. The solutions were then filtered using a 0.2 μm nylon filter. Aliquots of 150 μl of solution (acetone or tetrahydrofuran) were added to 50 μl of a second solvent in the wells of a flat bottom polypropylene 96-well plate. The plate was covered by a polypropylene mat, and the mat was pierced with one hole per well. Two identical plates were prepared. One of the plates was sonicated for 20 seconds every 30 minutes until evaporation to dryness of all samples in each well. Sonication was performed using a Misonix 3000 sonicator with microplate horn. The second plate was kept undisturbed (umsonicated), during the time of the evaporation. Table 7 summarizes the results obtained for the sonicated and unsonicated plates for each condition of evaporation. The difficult-to-make but more stable Form II was found in the sonicated plate but not in the unsonicated plate.

TABLE 7

Conditions Of Evaporations From Mixture Of Solvents

| Solvent 1 | Solvent 2 | Sonicated Form | Non-sonicated Form |
|---|---|---|---|
| acetone | Acetonitrile | II[a] | I[a] |
| acetone | Chloroform | I | I |
| acetone | 1,4-dioxane | I | A[c] |
| acetone | Ethanol | I | I |
| acetone | ethyl acetate | I | I |
| acetone | Heptane | I | I |
| acetone | 2-butanone | I | I |
| acetone | Methanol | I | I |
| acetone | Nitromethane | II[b] | I[a] |
| acetone | Tetrahydrofuran | I | I |
| acetone | Toluene | I | I |
| acetone | Water | I | I |
| tetrahydrofuran | Acetone | I | I |
| tetrahydrofuran | Acetonitrile | I | I |
| tetrahydrofuran | Chloroform | I | I |
| tetrahydrofuran | 1,4-dioxane | I | A[c] |
| tetrahydrofuran | Ethanol | I | I |
| tetrahydrofuran | ethyl acetate | I | I |
| tetrahydrofuran | heptane | I | I |
| tetrahydrofuran | 2-butanone | I | I |
| tetrahydrofuran | methanol | I | I |
| tetrahydrofuran | nitromethane | I | I |
| tetrahydrofuran | toluene | I | I |
| tetrahydrofuran | Water | I | I |

[a]duplicate experiment gave the same result
[b]duplicate experiment gave form I
[c]new form In this example, the elusive, more stable Form II of sulfamerazine was generated by a crystallization process that included ultrasound application, but was not generated without ultrasound application. This example shows that a screening process that includes sonication is more likely to generate the more stable solid forms of the chemical substance. This example also demonstrates that it may be desirable to include some unsonicated samples in a screening process, as this can increase the likelihood of obtaining the possible solid forms of the chemical substance.

EXAMPLE 8

In this Example, the difficult-to-make Form I of sulfathiazole was generated by crystallization from a solvent mixture with sonication used to form an emulsion.

Sulfathiazole Form I is a disappearing polymorph, today rarely seen crystallized directly from solution. This result is of interest for polymorph screening purposes. Blagden et al., "Crystal structure and solvent effects in polymorphic systems: sulfathiazole," J. Chem. Soc. Faraday, 94, 1035-1045 (1998).

Figure 7:
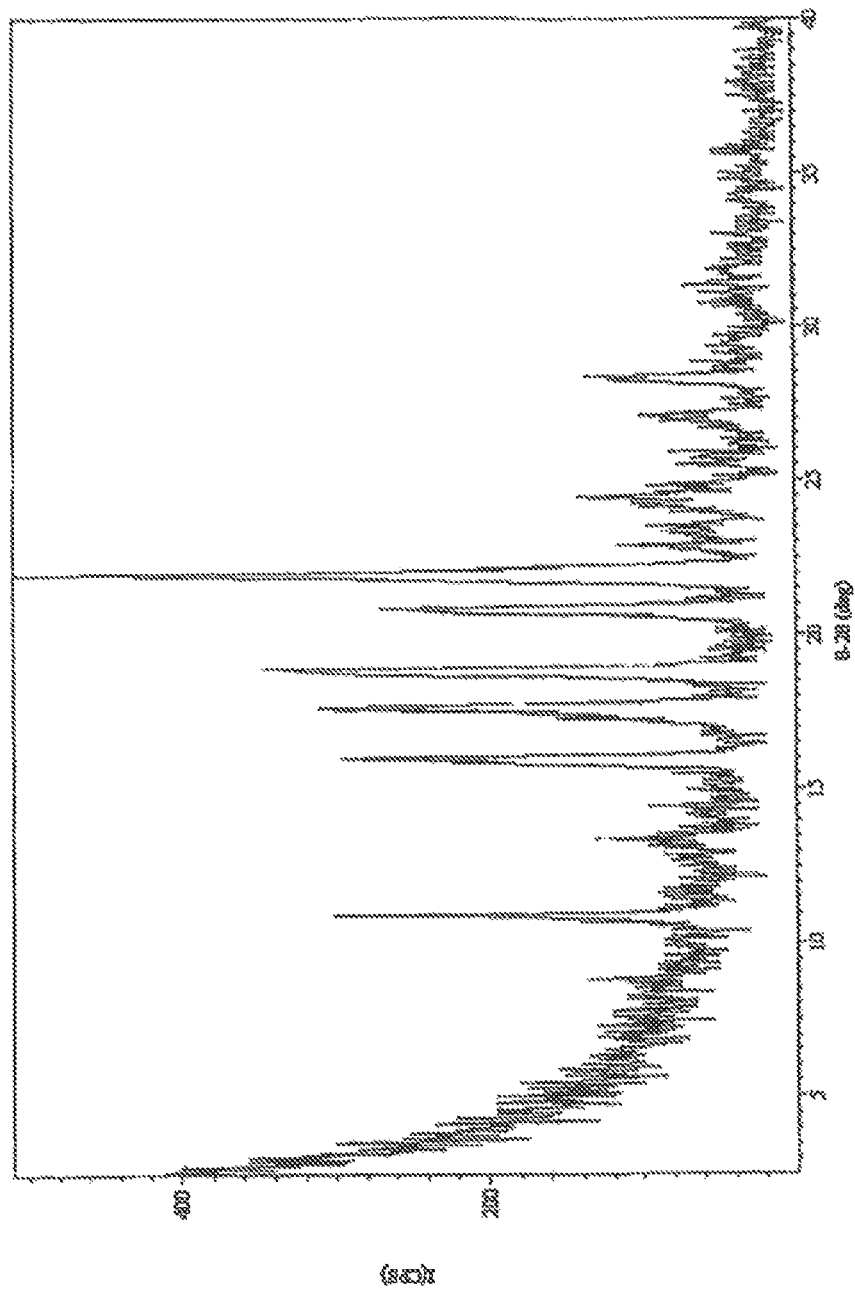
FIG. 7 is an XRPD pattern of sulfathiazole solidified from an ethanol/p-cymene emulsion.

A 500 μl aliquot of a saturated solution of sulfathiazole in ethanol at 50° C. was filtered hot and added to 500 μl of warm p-cymene in a pre-heated 1-dram vial on a hotplate at 55° C. The biphasic sample was then sonicated while evaporating until a precipitate appeared (40 minutes sonication, using a Cole-Palmer ultrasonic processor fitted with a 6 mm tip stainless steel probe, amplitude control set at 60). The solids obtained were filtered and analyzed by XRPD. The XRPD pattern was characteristic of sulfathiazole Form I (FIG. 7).

EXAMPLE 9

In this example a polymorph screen is carried out. Solutions of chemical substance A in the following solvents or solvent mixtures (with volume:volume ratio indicated) are prepared by robotic weighing of chemical substance and solvent delivery and mixing: acetone, acetonitrile, chloroform, 1,4-dioxane, ethanol, ethyl acetate, heptane, 2-butanone, methanol, nitromethane, tetrahydrofuran, toluene, water, dichloromethane, diethyl ether, isopropyl ether, cyclohexane, methylcyclohexane, isopropyl alcohol, trimethylpentane, n-octane, trichloroethane, trifluoroethanol, pyridine, 1-butanol, tetrachloroethylene, chlorobenzene, xylene, dibutyl ether, tetrachloroethane, p-cymene, dimethyl sulfoxide, formamide, dimethylformamide, 2:1 methanol:acetonitrile, 2:1 methanol:dichloromethane, 3:1 nm ethanol:ethyl acetate, 4:1 methanol:methyl-tert-butyl ether, 1:1 methanol:2-butanone, 3:1 trifluoroethanol:isopropyl acetate, 2:1 trifluoroethanol:isopropyl ether, 1:1 trifluoroethanol:nitromethane, 1:5 water:acetone, 1:4 water:acetonitrile, 1:5 water:dioxane, 1:9 water:2-propanol and 1:5 water:tetrahydrofuran.

Aliquots of 200 μL of each solution are delivered in duplicate using a liquid handler to the wells of a 96 well plate. Concentrations of the solutions are selected such that the final amount of chemical substance in each well is between 0.1 mg and 1.0 mg. The well plate body is made of polypropylene. The well plate is a thin bottom well plate suitable for x-ray diffraction analysis of crystals in the well plate. Two wells contain samples of an x-ray powder diffraction standard. The well plate solutions are left uncovered and are allowed to evaporate to dryness while being sonicated for 20 seconds every hour using a Misonix 3000 sonicator with microplate horn. Nitrogen flow into wells is used when evaporation needs to be facilitated. The well plate is mounted on edge on the stage of a Bruker D8 microdiffractometer with the well openings facing the x-ray source. The solids at the bottom of each well are analyzed by automated stage movement. It is expected that a useful variety of different solid forms of the chemical substance will be produced in the wells.

EXAMPLE 10

Cocrystals of fluoxetine HCl:benzoic acid were formed using the following procedures. A solution of fluoxetine HCl and benzoic acid in acetonitrile was prepared. A physical mixture of fluoxetine HCl and benzoic acid in a 1:1 molar ratio was used to make a solution having a concentration of about 200 mg/mL. The solution was placed in four 96-well plates. The only difference among well plates was the amount of solution put into each well. Two well plates were charged with 15 μL per well, and two plates were charged with 50 μL per well. One of the well plates containing 15 μL samples and one of the well plates containing 50 μL samples were sealed and left standing at room temp. The other well plate containing 15 μL samples and the other well plate containing 50 μL samples were sealed and sonicated with a Misonix 96-well plate sonicator.

None of the wells in the 15 μL plates (either standing or sonicated) nucleated (even after very strong sonication with the Misonix plate sonicator or the probe). The plate left standing at room temp with 50 μL volumes nucleated in about 15% of the wells nucleated on standing (but the majority of the wells had benzoic acid growth, not cocrystal nucleation). For the 50 μL plate that was sonicated, almost half of the wells nucleated (with only one well of benzoic acid and the rest as cocrystal).

In a system comprising a 1:1 molar ratio of fluoxetine HCl and benzoic acid in acetonitrile, concentrations of about 200 mg/ml of the API:guest mixture in CH$_3$CN (acetonitrile) were used. Nucleation could be caused by sonication in a concentration range of from about 35 to about 100 mg/ml. Sonication indicates a clear advantage in this case of intermediate concentrations. Almost all of the samples having a concentration of 200 mg/ml nucleated with sonication using either a probe or the well-plate sonicator. In contrast, about 15% of the wells in a plate at 200 mg/ml nucleated the cocrystal without sonication.

EXAMPLE 11

Cocrystal screening of chlorzoxazone is carried out using the following procedures. Solutions of chlorzoxazone and various guests are prepared in acetonitrile, methanol, aqueous ethanol, and acetone in 1:1 molar ratios having a concentrations of about 10 mg/mL. The guests used include benzoic acid, gallic acid, and 2,5-dihydroxybenzoic acid. Aliquots of 20 microliters of the solutions are placed in different capillary tubes. The samples are sonicated for 1 minute by placement of the capillary tubes in a sonication bath after the volume of the solutions are reduced to the point where both components are supersaturated. This concentration is calculated based on the solubility of the individual components. The sonication is repeated every hour for 24 hours as the solutions evaporate. A duplicate set of capillary tubes is allowed to evaporate at room temperature without sonication.

Solids are present in most of the capillary tubes and are analyzed by Raman spectroscopy and by x-ray powder diffraction. It is expected that a number of cocrystals are present in the sonicated capillary tubes and that different polymorphs, hydrates, or solvates of the cocrystals may also be present. It is expected that solids in the unsonicated capillary tubes will have a different variety of solid forms present compared to the sonicated samples and that there will not be as many cocrystals formed.

This example demonstrates the use of capillary tubes for cocrystallization. This example also demonstrations that samples having low concentrations and/or low volumes may be employed in a cocrystallization process.

EXAMPLE 12

Cocrystal and salt screening of imipramine hydrochloride is carried out using the following procedures. Solutions of imiprimine hydrochloride and various guests are prepared in acetonitrile, methanol, aqueous ethanol, and acetone in 1:1 molar ratios having a concentrations of about 10 mg/mL. The guests include benzoic acid, gallic acid, and 2,5-dihydroxybenzoic acid. Aliquots of 100 microliters of the solutions are placed in different wells of 96-well polypropylene plates that have thin walls. The plates are sonicated for 1 minute in a sonication bath after the volume of the solutions are reduced to the point where both components are supersaturated. This concentration is calculated based on the solubility of the individual components. The sonication is repeated every hour for 24 hours as the solutions continue to evaporate. A duplicate set of well plates is allowed to evaporate at room temperature without sonication.

Solids are present in most of the wells and are analyzed in situ, automatically by transmission x-ray powder diffraction through the well plates. It is expected that a number of cocrystals and/or salts are present in the sonicated plates and that different polymorphs, hydrates, solvates, desolvates, and dehydrates of the cocrystals and/or salts may also be present. It is expected that solids in the unsonicated plates will have a different variety of solid forms present compared to the sonicated samples and that there will not be as many cocrystals and/or salts formed.

All patents, test procedures, and other documents cited herein, including priority documents, are fully incorporated by reference to the extent such disclosure is not inconsistent with this invention and for all jurisdictions in which such incorporation is permitted.

While the present invention has been described and illustrated by reference to particular embodiments, it will be appreciated by those of ordinary skill in the art that the invention lends itself to many different variations not illustrated herein. For these reasons, then, reference should be made solely to the appended claims for purposes of determining the true scope of the present invention.

Although the appendant claims have single appendencies in accordance with U.S. patent practice, each of the features in any of the appendant dams can be combined with each of the features of other appendant claims or the main claim.

TABLE 8

10-camphorsulfonic acid
10-undecylenic acid
1-hydroxy-2-naphthoic acid
2,4-dihydroxybenzoic acid
2,5-dihydroxybenzoic acid
2-aminopropionic acid
2-ethylbutyrinc acid
2-furancarboxylic acid
2-mercaptobenzoic acid
3-methylbutanoic acid
3-phenylpropionic acid
4-aminobenzoic acid
4-aminosalicylic acid
4-hydroxybenzoic acid
adipic acid
alginic acid
anisic acid
arginine
ascorbic acid
asparagine
aspartic acid
aspirin
benzenesulfonic acid
benzoic acid
4-acetamidobenzoic acid
beta-alanine
camphoric acid
camphorsulfonic acid
carbonic acid TABLE 8-continued cholic acid
cinnamic acid
citric acid
cyclamic acid
cyclohexanecarboxylic acid
cyclohexylacetic acid
cysteine
diphenylacetic acid
dodecylsulfonic acid
ethane-1,2-disulfonic acid
ethanesulfonic acid
ethanesulfonic acid, 2-hydroxy
ethylenediaminetetraacetic acid
ethylsulfuric acid
fumaric acid
galactaric acid
gallic acid
gentisic acid
glucoheptonic acid
gluconic acid
glutamic Acid
glutamine
glutaric acid
glutaric acid, 2-oxo-
glycine
glycolic acid
hippuric acid
histidine
hydroxyproline
isoleucine
lactobionic acid
lauric acid
leucine
levulinic acid
lysine
maleic acid
malic acid
malonic acid
mandelic acid
m-methoxybenzoic acid
naphthalene-1,5-disulfonic acid
naphthalene-2-sulfonic acid
n-decanoic acid
niacin
nicotinic acid
n-tetradecanoic acid
oleic acid
o-methylbenzoic acid
orotic acid
orthoboric acid
o-toluic acid
p-acetamidobenzoic acid
palmitic acid
pamoic acid
phenoxyacetic acid
phenylacetic acid
phenylalanine
picric acid
pivalic acid
proline
p-toluenesulfonic acid
pyroglutamic acid
pyruvic acid
salicylic acid
sebacic acid
serine
sorbic acid
stearic acid
succinic acid
sulfosalicylic acid
tartaric acid
terephthalic acid
thiocyanic acid
threonine
tiglic acid
tryptophan
tyrosine
valeric acid
valine

TABLE 9

| Name | CAS # |
|---|---|
| Potassium bicarbonate | 298-14-6 |
| Potassium carbonate | 584-08-7 |
| Potassium chloride | 7447-40-7 |
| Potassium hydroxide | 1310-58-3 |
| Potassium metabisulfite | 16731-55-8 |
| Potassium nitrate | 7757-79-1 |
| Potassium nitrite | 7758-09-0 |
| Potassium permanganate | 7722-64-7 |
| Potassium persulfate | 7727-21-1 |
| Potassium phosphate, dibasic | 2139900 |
| Potassium Phosphate Monobasic | 7778-77-0 |
| potassium phosphate, tribasic, n-hydrate | 7778-53-2 |
| Potassium sulfate | 7778-80-5 |
| Sodium bicarbonate | 144-55-8 |
| Sodium bisulfate | 7631-90-5 |
| Sodium borohydride | 16940-66-2 |
| Sodium carbonate | 497-19-8 |
| Sodium Carbonate Monohydrate | 1486118 |
| Sodium chloride | 7647-14-5 |
| Sodium dithionite | 7775-14-6 |
| Sodium fluoride | 7681-49-4 |
| Sodium hexametaphosphate | 10124-56-8 |
| Sodium hydroxide | 1310-73-2 |
| Sodium hypochlorite | 7681-52-9 |
| Sodium Metabisulfite | 7681-57-4 |
| Disodium metasilicate | 6834-92-0 |
| sodium monophosphate | 7681-53-0 |
| Sodium nitrate | 7631-99-4 |
| Sodium nitrite | 7632-00-0 |
| sodium hydrogen phosphate | 7558-79-4 |
| Sodium Phosphate Monobasic | 7558-80-7 |
| Sodium Pyrophosphate | 7722-88-5 |
| Sodium silicate | 1344-09-8 |
| Sodium Sulfate Decahydrate | 7727-73-3 |
| Sodium sulfite | 7757-83-7 |
| Sodium Thiosulfate Pentahydrate | 10102-17-7 |
| Calcium acetate | 5743-26-0 |
| Calcium Carbonate | 471-34-1 |
| Calcium Chloride Dihydrate | 10035-04-8 |
| Calcium gluconate | 299-28-5 |
| Calcium hydroxide | 1305-62-0 |
| Calcium oxide | 1305-78-8 |
| Calcium phosphate, dibasic | 7757-93-9 |
| Calcium Phosphate Monobasic | 7758-23-8 |
| Calcium sulfate | 7778-18-9 |
| Magnesium hydroxide | 1309-42-8 |
| Magnesium Sulfate Heptahydrate | 10034-99-8 |
| Aluminum | 7429-90-5 |
| Aluminum ammonium sulfate | 7784-26-1 |
| Aluminum chloride | 7446-70-0 |
| Aluminum hydroxide | 21645-51-2 |
| Aluminum potassium sulfate, dodecahydrate | 7784-24-9 |
| Orthoboric acid | 10043-35-3 |
| formaldehyde | 50-00-0 |
| DL-Isoleucine | 443-79-8 |
| (2S,7S)-(−)-Cystine | 56-89-3 |
| DL-Alanine | 302-72-7 |
| beta-Alanine | 107-95-9 |
| (S)-(+)-Arginine | 74-79-3 |
| (S)-(−)-Cysteine | 52-90-4 |
| DL-Glutamic acid | 617-65-2 |
| Glycine | 56-40-6 |
| (S)-(−)-Histidine | 71-00-1 |
| (S)-(+)-Lysine | 56-87-1 |
| DL-Methionine | 59-51-8 |
| DL-Phenylalanine | 150-30-1 |
| (S)-(−)-Phenylalanine | 63-91-2 |
| D-(+)-Proline | 344-25-2 |
| (S)-(−)-Tryptophan | 73-22-3 |
| (S)-(−)-Tyrosine | 60-18-4 |
| Carvone | 99-49-0 |
| Citral | 5392-40-5 |
| Ethyl butyrate | 105-54-4 |
| Isobutyl propionate | 540-42-1 |
| Methyl butyrate | 623-42-7 |
| n-Propyl acetate | 109-60-4 |
| Isobutyl formate | 542-55-2 |
| Benzyl acetate | 140-11-4 |
| 6-Methyl-5-hepten-2-one | 110-93-0 |
| Butyl acetate | 123-86-4 |
| Ethyl acetoacetate | 141-97-9 |
| Isopentyl Acetate | 123-92-2 |
| Cinnamaldehyde | 104-55-2 |
| Methyl benzoate | 93-58-3 |
| Butyl sulfide | 544-40-1 |
| Ethyl benzoate | 93-89-0 |
| 2,4-Hexadienoic acid, potassium salt, (E,E)- | 24634-61-5 |
| Potassium bitartrate | 868-14-4 |
| Lauric acid | 143-07-7 |
| Benzyl benzoate | 120-51-4 |
| Picric acid | 88-89-1 |
| Benzoyl peroxide | 94-36-0 |
| Palmitic acid | 57-10-3 |
| Dibutyl phthalate | 84-74-2 |
| Stearic acid | 57-11-4 |
| Succinic anhydride | 108-30-5 |
| Diethylenetriamine | 111-40-0 |
| Diethanolamine | 111-42-2 |
| Benzaldehyde | 100-52-7 |
| Phenethylamine | 64-04-0 |
| Salicylylaldehyde | 90-02-8 |
| Sodium benzoate | 532-32-1 |
| Cinnamic acid | 621-82-9 |
| Triethanolamine | 102-71-6 |
| L-(+)-Tartaric Acid | 87-69-4 |
| Eugenol | 97-53-0 |
| D-mannitol | 69-65-8 |
| Butyl paraben | 94-26-8 |
| Benzoin | 119-53-9 |
| Diethyl phthalate | 84-66-2 |
| Oleic acid | 112-80-1 |
| Sodium lactate | 72-17-3 |
| Indole | 120-72-9 |
| ethyl lactate | 97-64-3 |
| quinoline | 91-22-5 |
| Thymol | 89-83-8 |
| Methyl anthranilate | 134-20-3 |
| Methyl salicylate | 119-36-8 |
| Diethyl malonate | 105-53-3 |
| Citric acid | 77-92-9 |
| Sodium dodecyl sulfate | 151-21-3 |
| Morpholine | 110-91-8 |
| Furfural | 98-01-1 |
| Niacin | 59-67-6 |
| Choline chloride | 67-48-1 |
| L-Menthol | 2216-51-5 |
| Meso-inositol | 87-89-8 |
| ethylenediaminetetraacetic acid | 60-00-4 |
| EDTA, calcium derivative, disodium salt | 62-33-9 |
| Calcium pantothenate | 137-08-6 |
| Riboflavin | 83-88-5 |
| Zinc carbonate | 3486-35-9 |
| Amyl alcohol | 71-41-0 |
| Mineral oil | 8012-95-1 |
| Triton(R) X-100 | 9002-93-1 |
| Acetaldehyde | 75-07-0 |
| Acetic Acid | 64-19-7 |
| Acetone | 67-64-1 |
| Acetophenone | 98-86-2 |
| 4-Aminobenzoic acid | 150-13-0 |
| Anisole | 100-66-3 |
| Vitamin C | 50-81-7 |
| Benzoic Acid | 65-85-0 |
| Biphenyl | 92-52-4 |
| 2-Methyl-1-propanol | 78-83-1 |
| n-Butanol | 71-36-3 |
| n-Butylamine | 109-73-9 |
| ethyl acetate | 141-78-6 |
| Caffeine | 58-08-2 |
| Chloroacetic Acid | 79-11-8 |
| Dichloroacetic Acid | 79-43-6 |
| Diethylamine | 109-89-7 |
| Ethanol Amine | 141-43-5 |
| n-Butyric Acid | 107-92-6 |
| Ethylenediamine | 107-15-3 |
| Formic acid | 64-18-6 |

TABLE 9-continued

| Name | CAS # |
|---|---|
| n-Hexanol | 111-27-3 |
| Methanol | 67-56-1 |
| Methyl Acetate | 79-20-9 |
| Methyl 4-hydroxybenzoate | 99-76-3 |
| m-Cresol | 108-39-4 |
| p-Cresol | 106-44-5 |
| Phenol | 108-95-2 |
| n-Propanol | 71-23-8 |
| Propionic Acid | 79-09-4 |
| Salicylic acid | 69-72-7 |
| Sucrose | 57-50-1 |
| Vanillin | 121-33-5 |
| Vitamin E | 59-02-9 |
| Potassium citrate, monohydrate | 1534146 |
| p-toluenesulfonic acid monohydrate | 6192-52-5 |
| D-(+)-Maltose | 69-79-4 |
| Tetrasodium ethylenediaminetetraacetate | 64-02-8 |
| Saccharin sodium | 128-44-9 |
| Sodium Acetate Trihydrate | 6131-90-4 |
| Quinine sulfate, dihydrate | 6119-70-6 |
| Sulfosalicylic acid, dihydrate | 5965-83-3 |
| L-(+)-Arginine monohydrochloride | 1119-34-2 |
| Procaine hydrochloride | 51-05-8 |
| Pyridoxine Hydrochloride | 58-56-0 |
| Thiamine hydrochloride | 67-03-8 |
| Propionaldehyde | 123-38-6 |
| Urea | 57-13-6 |
| 2-Propanol | 67-63-0 |
| Pyrrole | 109-97-7 |
| Sodium formate | 141-53-7 |
| Pyrrolidine | 123-75-1 |
| Methyl ethyl ketone | 78-93-3 |
| Ethyl formate | 109-94-4 |
| Propylene glycol | 57-55-6 |
| Thiourea | 62-56-6 |
| Ammonium acetate | 631-61-8 |
| Benzene | 71-43-2 |
| Sodium acetate | 127-09-3 |
| Cyclopentanone | 120-92-3 |
| Cyclohexane | 110-82-7 |
| piperidine | 110-89-4 |
| 2-Pentanone | 107-87-9 |
| hexane | 110-54-3 |
| Isoamyl Alcohol | 123-51-3 |
| Lactic acid | 50-21-5 |
| 2-Ethoxyethanol | 110-80-5 |
| Propionic acid, sodium salt | 137-40-6 |
| Potassium acetate | 127-08-2 |
| cyclohexyl amine | 108-91-8 |
| methyl methacrylate | 80-62-6 |
| methyl isobutyl ketone | 108-10-1 |
| Acetic anhydride | 108-24-7 |
| Isopropyl Acetate | 108-21-4 |
| 2,2'-Oxybisethanol | 111-46-6 |
| Benzyl alcohol | 100-51-6 |
| Resorcinol | 108-46-3 |
| 2-Butoxy ethanol | 111-76-2 |
| Cumene | 98-82-8 |
| 2-Amino-2-(hydroxymethyl)-1,3-propanediol | 77-86-1 |
| Phenethyl alcohol | 60-12-8 |
| 2-Ethyl-1-hexanol | 104-76-7 |
| 2-Octanol | 123-96-6 |
| 2-(2-Ethoxyethoxy)ethanol | 111-90-0 |
| 2,6-Dimethyl-4-heptanone | 108-83-8 |
| Benzophenone | 119-61-9 |
| D-(−)-Fructose | 57-48-7 |
| D-Glucose | 50-99-7 |
| D-Ribose | 50-69-1 |
| D-(+)-Xylose | 58-86-6 |
| Pectin sugar | 5328-37-0 |
| D-(+)-Lactose | 63-42-3 |
| Camphene | 79-92-5 |
| Isoquinoline | 119-65-3 |
| 2,4-Dimethylphenol | 105-67-9 |
| 2,5-Dimethylphenol | 95-87-4 |
| 2,6-Dimethylphenol | 576-26-1 |
| Methanesulfonic Acid | 75-75-2 |
| o-Methoxybenzoic Acid | 579-75-9 |
| Saccharin | 81-07-2 |
| Thiazole | 288-47-1 |
| Trifluoromethanesulfonic Acid | 1493-13-6 |
| Trimethylamine | 75-50-3 |
| Coumarin | 91-64-5 |
| Dimethylamine | 124-40-3 |
| Ethyl Alcohol | 64-17-5 |
| Butyl benzyl phthalate | 85-68-7 |
| 2,6-dimethylpyrazine | 108-50-9 |
| taurocholic acid | 81-24-3 |
| geraniol | 106-24-1 |
| linalool | 78-70-6 |
| ethyl isovalerate | 108-64-5 |
| ethyl 2-methylbutyrate | 7452-79-1 |
| 1-octen-3-ol | 3391-86-4 |
| ethyl 2-trans-4-cis decadienoate | 3025-30-7 |
| Dihydromyrcenol | 18479-58-8 |
| citronellal | 106-23-0 |
| linalyl acetate | 115-95-7 |
| 8-mercapto-p-menthan-3-one | 38462-22-5 |
| Ammonium citrate | 3012-65-5 |
| Ammonium bicarbonate | 1066-33-7 |
| Ammonium chloride | 12125-02-9 |
| Ammonium hydroxide | 1336-21-6 |
| Ammonium persulfate | 7727-54-0 |
| Ammonium phosphate, dibasic | 7783-28-0 |
| Ammonium Phosphate Monobasic | 7722-76-1 |
| Ammonium sulfate | 7783-20-2 |
| Ammonium sulfide | 12135-76-1 |
| Hydrazine | 302-01-2 |
| Nitric acid | 7697-37-2 |
| phosphoric acid | 7664-38-2 |
| Phosphorus oxychloride | 10025-87-3 |
| Hydriodic acid | 10034-85-2 |
| Hydrobromic acid | 10035-10-6 |
| Hydrochloric acid | 7647-01-0 |
| hydrogen peroxide | 7722-84-1 |
| Periodic Acid | 10450-60-9 |
| Sulfamic acid | 5329-14-6 |
| Sulfuric acid | 7664-93-9 |
| Sulfurous acid | 7782-99-2 |
| Dexpanthenol | 81-13-0 |
| 4-oxoisophorone | 1125-21-9 |
| Copper(II) sulfate | 7758-98-7 |
| ferric chloride | 7705-08-0 |
| Ferric oxide | 1309-37-1 |
| ferric sulfate | 10028-22-5 |
| Iron(II)Sulfate Heptahydrate | 7782-63-0 |
| Iron | 7439-89-6 |
| Manganese (II) Sulfate Monohydrate | 10034-96-5 |
| Nickel | 7440-02-0 |
| Titanium dioxide | 13463-67-7 |
| Zinc chloride | 7646-85-7 |
| Zinc oxide | 1314-13-2 |
| 1,1'-Azobisformamide | 123-77-3 |
| 1,3-Butanediol | 107-88-0 |
| 1-Methylnaphthalene | 90-12-0 |
| 2,6-Di-tert-Butyl-p-Cresol | 128-37-0 |
| 2,6-Dimethylpyridine | 108-48-5 |
| Disodium cyanodithioimidocarbonate | 138-93-2 |
| 3-Methyl-2-Cyclopentene-2-ol-one | 80-71-7 |
| 6-Methylcoumarin | 92-48-8 |
| acetoin | 513-86-0 |
| alpha-Phellandrene | 99-83-2 |
| alpha-Terpinene | 99-86-5 |
| Benzenesulfonic Acid | 98-11-3 |
| Benzothiazole | 95-16-9 |
| borates, tetrasodium salts | 1330-43-4 |
| Butyl butyrate | 109-21-7 |
| Butyl Mercaptan | 109-79-5 |
| Butyraldehyde | 123-72-8 |
| Capsaicin | 404-86-4 |
| Chloromethyl Methyl Ether | 107-30-2 |
| Cymene | 99-87-6 |
| Diallyl Disulfide | 2179-57-9 |
| Diethylaminoethanol | 100-37-8 |
| dimethyldisulfide | 624-92-0 |
| Dimethyl Succinate | 106-65-0 |

TABLE 9-continued

| Name | CAS # |
|---|---|
| Dimethyl Sulfate | 77-78-1 |
| Dimethyl Sulfide | 75-18-3 |
| Dipropyl Disulfide | 629-19-6 |
| Dipropyl Ketone | 123-19-3 |
| Ethyl Acrylate | 140-88-5 |
| Ethyl Butyl Ketone | 106-35-4 |
| Ethyl Propionate | 105-37-3 |
| Furfuryl Alcohol | 98-00-0 |
| gamma-Butyrolactone | 96-48-0 |
| Glutaraldehyde | 111-30-8 |
| glycerin | 56-81-5 |
| Glycolic Acid | 79-14-1 |
| Isobutyl Acetate | 110-19-0 |
| Isobutyl Isobutyrate | 97-85-8 |
| Isobutyraldehyde | 78-84-2 |
| Isoheptanol | 543-49-7 |
| Isophorone | 78-59-1 |
| Isopropyl Mercaptan | 75-33-2 |
| Methyl isobutenyl ketone | 141-79-7 |
| Methyl n-amyl ketone | 110-43-0 |
| methyl acrylate | 96-33-3 |
| Methyl Isobutyrate | 547-63-7 |
| Methyl Mercaptan | 74-93-1 |
| N,N-Dimethylethanolamine | 108-01-0 |
| n-Butyl Lactate | 138-22-7 |
| n-Hexyl Acetate | 142-92-7 |
| n-Valeraldehyde | 110-62-3 |
| Nitrous Oxide | 10024-97-2 |
| p-Anisaldehyde | 123-11-5 |
| 2-Methylcyclohexanone | 583-60-8 |
| Octanoic Acid | 124-07-2 |
| Oxalic Acid | 144-62-7 |
| Phenyl ether | 101-84-8 |
| Phenylmercaptan | 108-98-5 |
| Propargyl Alcohol | 107-19-7 |
| Propyl paraben | 94-13-3 |
| sec-Butyl Alcohol | 78-92-2 |
| Sodium Gluconate | 527-07-1 |
| Sodium Tripolyphosphate | 7758-29-4 |
| Tetrahydro-2-furanmethanol | 97-99-4 |
| Valeric Acid | 109-52-4 |
| 3,4-xylenol | 95-65-8 |
| 3-hexanol | 623-37-0 |
| 3-methyl-1-pentanol | 589-35-5 |
| 1,1-diethoxyethane | 105-57-7 |
| Aluminum Sulfate | 10043-01-3 |
| ammonium sulfite | 10196-04-0 |
| amyl butyrate | 540-18-1 |
| borneol | 507-70-0 |
| butyl formate | 592-84-7 |
| calcium peroxide | 1305-79-9 |
| n-Hexanoic Acid | 142-62-1 |
| cyclohexyl acetate | 622-45-7 |
| diacetyl | 431-03-8 |
| dimethyl carbonate | 616-38-6 |
| ethyl butyraldehyde | 97-96-1 |
| Ethyl crotonate | 623-70-1 |
| ethyl isobutyrate | 97-62-1 |
| ethyl nitrite | 109-95-5 |
| fumaric acid | 110-17-8 |
| hexaldehyde | 66-25-1 |
| isobutyric acid | 79-31-2 |
| methyl isovalerate | 556-24-1 |
| methyl propionate | 554-12-1 |
| methyl valeraldehyde | 123-15-9 |
| nitrosyl chloride | 2696-92-6 |
| octafluorocyclobutane | 115-25-3 |
| peroxyacetic acid | 79-21-0 |
| propyl formate | 110-74-7 |
| propyl mercaptan | 107-03-9 |
| Sodium aluminate | 1302-42-7 |
| sodium chlorite | 7758-19-2 |
| Terephthalic Acid | 100-21-0 |
| allyl isothiocyanate | 57-06-7 |
| Vitamin B1 | 59-43-8 |
| Valproic acid | 99-66-1 |
| Ethoxyquin | 91-53-2 |
| n-Amyl Ethyl Ketone | 106-68-3 |
| Nabam | 142-59-6 |
| Sodium sulfide | 1313-82-2 |
| Thiocyanic acid | 463-56-9 |
| 2-Methyl-5-(1-methylethenyl)-2-cyclohexene-1-one | 2244-16-8 |
| 4-(2,6,6-Trimethyl-2-cyclohexen-1-yl)-3-buten-2-one | 127-41-3 |
| 4-(2,6,6-trimethyl-1-cyclohexen-1-yl)-3-buten-2-one | 14901-07-6 |
| Isoamyl propionate | 105-68-0 |
| 3-Methylbutanoic acid | 503-74-2 |
| L-Menthone | 14073-97-3 |
| 4-Ethylphenol | 123-07-9 |
| o-cresol | 95-48-7 |
| dimethyl-Carbamodithioic acid, sodium salt | 128-04-1 |
| Anethole | 104-46-1 |
| Dimethyl terephthalate | 120-61-6 |
| propyl gallate | 121-79-9 |
| L-Ascorbic Acid Sodium Salt | 134-03-2 |
| 4-Hexylresorcinol | 136-77-6 |
| Estragole | 140-67-0 |
| L-monosodium glutamate | 142-47-2 |
| Malonaldehyde, sodium salt | 24382-04-5 |
| Butylated hydroxyanisole | 25013-16-5 |
| allyl 3-methylbutyrate | 2835-39-4 |
| DL-monosodium glutamate | 32221-81-1 |
| 3-Acetyl-6-methyl-2,4-pyrandione | 520-45-6 |
| L-Glutamic Acid | 56-86-0 |
| DL-alpha-tocopheryl acetate | 58-95-7 |
| D-limonene | 5989-27-5 |
| Calcium Acetate | 62-54-4 |
| Erythorbic Acid Monosodium Salt | 6381-77-7 |
| Ethyl methylphenylglycidate | 77-83-8 |
| 2,4,6-Trinitro-1,3-dimethyl-5-tert-butylbenzene | 81-15-2 |
| Dimethoxane | 828-00-2 |
| 3,5-Di-tert-butyl-4 hydroxybenzyl alcohol | 88-26-6 |
| 6-Methylquinoline | 91-62-3 |
| alpha-Methylbenzyl alcohol | 98-85-1 |
| Nicotinamide | 98-92-0 |
| 3,4-Dihydrocoumarin | 119-84-6 |
| Geranyl Acetate | 105-87-3 |
| Sodium (2-Ethylhexyl)Alcohol Sulfate | 126-92-1 |
| Cyclohexanol, 5-methyl-2-(1-methylethyl)-, (1alpha, 2beta,5alpha)- | 89-78-1 |
| (+)-Camphor | 464-49-3 |
| (1S)-(−)-alpha-Pinene | 7785-26-4 |
| 1,3-Dihydroxy-5-methylbenzene | 504-15-4 |
| 1,5-Naphthalenedisulfonic Acid Disodium Salt | 1655-29-4 |
| 1-Hydroxy-2-naphthoic Acid | 86-48-6 |
| 1-Penten-3-ol | 616-25-1 |
| 1-Phenyl-1-propanol | 93-54-9 |
| 10-Undecylenic Acid | 112-38-9 |
| 2'-Hydroxyacetophenone | 118-93-4 |
| 2,4-Dihydroxybenzoic Acid | 89-86-1 |
| 2-Acetylfuran | 1192-62-7 |
| 2-Furancarboxylic Acid | 88-14-2 |
| 2-Isopropylphenol | 88-69-7 |
| 2-Ketoglutaric Acid | 328-50-7 |
| 2-Ketovaline | 759-05-7 |
| 2-n-Propylphenol | 644-35-9 |
| 2-Naphthalenethiol | 91-60-1 |
| 2-Phenyl-1-propanol | 1123-85-9 |
| 3,3'-Thiodipropionic Acid | 111-17-1 |
| 3,5,5-Trimethylhexanal | 5435-64-3 |
| 3-Phenyl-1-propanol | 122-97-4 |
| 3-Phenylpropionic Acid | 501-52-0 |
| 4-Aminosalicylic Acid | 65-49-6 |
| 4-Ethoxyphenol | 622-62-8 |
| 4-Hydroxybenzoic Acid | 99-96-7 |
| 4-Phenyl-2-butanol | 2344-70-9 |
| 4-tert-Octylphenol | 140-66-9 |
| Allyl Cinnamate | 1866-31-5 |
| Allyl Mercaptan | 870-23-5 |
| alpha-L-Rhamnose | 3615-41-6 |
| Alpha-Terpineol | 98-55-5 |
| Anisic Acid | 100-09-4 |
| Benzalacetone | 122-57-6 |
| Benzaldehyde Dimethylacetal | 1125-88-8 |
| Benzyl Ether | 103-50-4 |
| Benzyl Formate | 104-57-4 |
| Benzyl Mercaptan | 100-53-8 |

TABLE 9-continued

| Name | CAS # |
|---|---|
| Benzyl Salicylate | 118-58-1 |
| Calcium Citrate | 813-94-5 |
| Calcium Glycerophosphate | 27214-00-2 |
| Calcium Hypophosphite | 7789-79-9 |
| Calcium Iodate | 7789-80-2 |
| Propanoic acid, 2-hydroxy-, calcium salt (2:1) | 814-80-2 |
| Calcium Phosphate Tribasic | 7758-87-4 |
| Calcium Propionate | 4075-81-4 |
| Calcium Pyrophosphate | 7790-76-3 |
| Cholic Acid | 81-25-4 |
| Choline | 123-41-1 |
| Choline Bitartrate | 87-67-2 |
| trans-Cinnamic Aldehyde | 14371-10-9 |
| Cinnamyl Alcohol | 104-54-1 |
| Citronellol | 106-22-9 |
| Copper(I)Iodide | 7681-65-4 |
| D-(+)-Glucono-1,5-lactone | 90-80-2 |
| D-(−)-Tartaric Acid | 147-71-7 |
| D-Isoascorbic Acid | 89-65-6 |
| D-Tyrosine | 556-02-5 |
| Sodium dehydroacetate | 4418-26-2 |
| Deoxycholic Acid | 83-44-3 |
| Dibenzyl Ketone | 102-04-5 |
| Diethyl L-(+)-Tartrate | 87-91-2 |
| Diethyl Succinate | 123-25-1 |
| Dimethylacetal | 534-15-6 |
| DL-Cystine | 923-32-0 |
| DL-Proline | 609-36-9 |
| DL-Tartaric Acid | 133-37-9 |
| DL-Tyrosine | 556-03-6 |
| DL-Valine | 516-06-3 |
| Enanthoic Acid | 111-14-8 |
| Erythorbic Acid Sodium Salt | 7378-23-6 |
| Ethyl 2-Aminobenzoate | 87-25-2 |
| Ethyl Cinnamate | 103-36-6 |
| Ethyl n-Valerate | 539-82-2 |
| Ethyl Phenylacetate | 101-97-3 |
| Ethyl Salicylate | 118-61-6 |
| Ethyl Sulfide | 352-93-2 |
| Ethyl Vanillin | 121-32-4 |
| Ethylene Mercaptan | 540-63-6 |
| Farnesene | 502-61-4 |
| Folic acid | 59-30-3 |
| gamma-Nonanolactone | 104-61-0 |
| gamma-Valerolactone | 108-29-2 |
| Gluconic Acid | 526-95-4 |
| Gluconic Acid Potassium Salt | 299-27-4 |
| Glutaric Acid | 110-94-1 |
| Guanosine-5′-monophosphate, disodium salt | 1333479 |
| Heliotropine | 120-57-0 |
| Hippuric Acid | 495-69-2 |
| Hydroquinone Dimethyl Ether | 150-78-7 |
| Inosine-5′-monophosphate Sodium Salt | 4691-65-0 |
| iso-Amyl Mercaptan | 541-31-1 |
| Isoamyl Salicylate | 87-20-7 |
| iso-Butyl n-Hexanoate | 105-79-3 |
| isovaleraldehyde | 590-86-3 |
| Isoamyl Benzoate | 94-46-2 |
| Isoamyl Formate | 110-45-2 |
| Isoamyl n-Butyrate | 106-27-4 |
| Isoamylamine | 107-85-7 |
| Isobutyl n-Butyrate | 539-90-2 |
| Isocaproic Acid | 646-07-1 |
| Isoeugenol | 97-54-1 |
| Isopropyl Benzoate | 939-48-0 |
| Isopropyl Formate | 625-55-8 |
| Isopropyl N-Butyrate | 638-11-9 |
| Isopropyl Propionate | 637-78-5 |
| isobutyl Mercaptan | 513-44-0 |
| L-(+)-Isoleucine | 73-32-5 |
| L-(−)-Apple Acid | 97-67-6 |
| L-2-Aminopropionic Acid | 56-41-7 |
| L-Aspartic acid | 56-84-8 |
| L-Carnitine | 541-15-1 |
| L-Cysteine Hydrochloride | 52-89-1 |
| L-Glutamic Acid Hydrochloride | 138-15-8 |
| L-Glutamine | 56-85-9 |
| L-Hydroxyproline | 51-35-4 |
| L-Proline | 147-85-3 |
| L-Serine | 56-45-1 |
| L-Threonine | 72-19-5 |
| L-Valine | 72-18-4 |
| N-Acetylglycine | 543-24-8 |
| n-Amyl Formate | 638-49-3 |
| n-Amyl n-Caproate | 540-07-8 |
| n-Butyl n-Caproate | 626-82-4 |
| n-Butyl Propionate | 590-01-2 |
| n-Butyl Salicylate | 2052-14-4 |
| n-Decanoic Acid | 334-48-5 |
| n-Hexyl Mercaptan | 111-31-9 |
| n-Propyl Benzoate | 2315-68-6 |
| n--Propyl Isobutyrate | 644-49-5 |
| n-Tetradecanoic Acid | 544-63-8 |
| Nitrilotriacetic Acid Trisodium Salt | 5064-31-3 |
| o-Toluenethiol | 137-06-4 |
| Orotic Acid | 65-86-1 |
| p-Acetamidobenzoic Acid | 556-08-1 |
| p-Anise Alcohol | 105-13-5 |
| Phenoxyacetic Acid | 122-59-8 |
| Phenyl Acetate | 122-79-2 |
| Piperine | 94-62-2 |
| Pivalic Acid | 75-98-9 |
| Potassium Benzoate | 582-25-2 |
| Potassium Diphosphate | 7320-34-5 |
| Potassium Hypophosphite | 7782-87-8 |
| Potassium Metaphosphate | 7790-53-6 |
| Potassium Sulfite | 10117-38-1 |
| Quinine Hydrochloride | 130-89-2 |
| sec-Amyl Alcohol | 6032-29-7 |
| Sodium D-Pantothenate | 867-81-2 |
| Di(2-ethylhexyl) sulfosuccinic acid, sodium salt | 577-11-7 |
| Sodium Sorbate | 7757-81-5 |
| Succinic acid, disodium salt | 150-90-3 |
| Sodium Taurocholate | 145-42-6 |
| Taurine | 107-35-7 |
| Thiamine Nitrate | 532-43-4 |
| Thioanisole | 100-68-5 |
| Tiglic Acid | 80-59-1 |
| Tri-n-butyrin | 60-01-5 |
| Triacetin | 102-76-1 |
| Trisodium Citrate | 68-04-2 |
| Veratraldehyde | 120-14-9 |
| Veratrole | 91-16-7 |
| Vitamin P | 520-26-3 |
| Vitamin U Chloride | 582174 |
| L-methionine | 63-68-3 |
| 2-Chloro-1-propanol | 78-89-7 |
| 2-Ethylbutyric acid | 88-09-5 |
| 2-Methylbutyraldehyde | 96-17-3 |
| 2-Methyl-5-ethylpyridine | 104-90-5 |
| n-propyl butyrate | 105-66-8 |
| Ethyl caprylate | 106-32-1 |
| Propyl propionate | 106-36-5 |
| 2-Methylpyrazine | 109-08-0 |
| 3,3,5-Trimethyl-1-cyclohexanol | 116-02-9 |
| Ethyl caproate | 123-66-0 |
| o-methoxybenzaldehyde | 135-02-4 |
| 2,4-Hexadienal | 142-83-6 |
| 3-Hexanone | 589-38-8 |
| 3-Methyl-2-butanol | 598-75-4 |
| Methyl isopropenyl ketone | 814-78-8 |
| 3-Methyl-2-butanethiol | 2084-18-6 |
| 3,5,5-Trimethylhexanol | 3452-97-9 |
| Methylglyoxal | 78-98-8 |
| Malonaldehyde | 542-78-9 |
| 1,4-Dithiane | 505-29-3 |
| Amylcinnamaldehyde | 122-40-7 |
| Benzyl cinnamate | 103-41-3 |
| tert-Butylhydroquinone | 1948-33-0 |
| Fusidic Acid Sodium Salt | 751-94-0 |
| Hydroxycitronellal | 107-75-5 |
| Musk ketone | 81-14-1 |
| L-Asparagine | 70-47-3 |
| phenethyl acetate | 103-45-7 |
| Riboflavin-5-Phosphate | 146-17-8 |
| Potassium Sodium Tartrate | 304-59-6 |

TABLE 9-continued

| Name | CAS # |
|---|---|
| Galactaric acid | 526-99-8 |
| Sodium Tartrate | 868-18-8 |
| trisodium phosphate | 7601-54-9 |
| Disodium Pytophosphate | 7758-16-9 |
| Magnesium chloride | 7786-30-3 |
| Sodium Polymethacrylate | 54193-36-1 |
| propiophenone | 93-55-0 |
| 2-ethylhexanoic acid | 149-57-5 |
| 3,7,7-trimethyl bicyclohep-3-ene | 13466-78-9 |
| 2,6-dimethyl-4-heptanol | 108-82-7 |
| 5-isopropyl-2-methyl-phenol | 499-75-2 |
| L-Bornyl acetate | 5655-61-8 |
| caryophyllene | 87-44-5 |
| hydroxymethylpyrone | 118-71-8 |
| neosperidin dihydrochalcone | 20702-77-6 |
| 2,2-Dibromo-3-nitrilopropionamide | 10222-01-2 |
| Xylitol | 87-99-0 |
| Sulfosalicylic acid | 97-05-2 |
| Riboflavin 5'-(dihydrogen phosphate), monosodium salt | 130-40-5 |
| Ethylenediaminetetraacetic acid, disodium salt | 139-33-3 |
| Gallic acid | 149-91-7 |
| Carbonic acid | 463-79-6 |
| Potassium carbonate, sesquihydrate | 6381-79-9 |
| Magnesium phosphate tribasic | 7757-87-1 |
| diallyl sulfide | 592-88-1 |
| ethyl 4-oxopentanoate | 539-88-8 |
| methyl caproate | 106-70-7 |
| isopropyl isobutyrate | 617-50-5 |
| diethyl hydroxybutanedioate | 2065419 |
| propyl isopentanoate | 557-00-6 |
| benzyl ethyl ether | 539-30-0 |
| isobutyl isopentanoate | 589-59-3 |
| propyl hexanoate | 626-77-7 |
| 4-methylquinoline | 491-35-0 |
| methyl cinnamate | 103-26-4 |
| cumic alcohol | 536-60-7 |
| thujone | 471-15-8 |
| dihydrocarveol | 619-01-2 |
| fenchyl alcohol | 1632-73-1 |
| Nerol | 106-25-2 |
| isopentyl isopentanoate | 659-70-1 |
| methyleugenol | 93-15-2 |
| methyl 2-naphthyl ketone | 93-08-3 |
| diphenyldisulfide | 882-33-7 |
| citronellyl acetate | 150-84-5 |
| menthyl acetate | 89-48-5 |
| menthyl isovalerate | 16409-46-4 |
| 5-Ethyl-3-hydroxy-4-methyl 2 (5H)-furanone | 698-10-2 |
| malic acid | 6915-15-7 |
| 3-methylbutanoic acid butyl ester | 109-19-3 |
| 3-phenyloxiranecarboxylic acid ethyl ester | 121-39-1 |
| 1,2-Benzisothiazol-3(2H)-one 1,1-dioxide, ammonium salt | 6381-61-9 |
| 1-methyl-4-(1-methylethyl)-1,4-Cyclohexadiene | 99-85-4 |
| 3-mercapto-2-Butanol | 54812-86-1 |
| (1R)-2,6,6-trimethylbicyclo[3.1.1]hept-2-ene | 7785-70-8 |
| (1S)-6,6-dimethyl-2-methylenebicyclo[3.1.1]heptane | 18172-67-3 |
| 1-methyl-4-(1-methylethylidene)cyclohexene | 586-62-9 |
| 1-(3-pyridinyl)ethanone | 350-03-8 |
| 1-pyrazinylethanone | 22047-25-2 |
| 1-(2-furyl)-2-propanone | 6975-60-6 |
| 1-Penten-3-one | 1629-58-9 |
| 2,3-pentanedione | 600-14-6 |
| 2,5-dimethylpyrazine | 123-32-0 |
| 2-isobutyl-3-methoxypyrazine | 24683-00-9 |
| 4-methyl-2,3-pentanedione | 7493-58-5 |
| 5-methylfurfural | 620-02-0 |
| Dimethyltrisulfide | 3658-80-8 |
| furfuryl acetate | 623-17-6 |
| furfurylmethylether | 13679-46-4 |
| terpinen-4-ol | 562-74-3 |
| Calcium sorbate | 7492-55-9 |
| Potassium lactate | 996-31-6 |
| 1-Hydroxyethylidene-1,1-diphosphonic acid | 2809-21-4 |
| L-glutamic acid monopotassium salt | 19473-49-5 |
| 3-methyl-2-buten-1-ol | 556-82-1 |
| phenylethanal | 122-78-1 |

| Name | CAS # |
|---|---|
| 4'-Methoxyacetophenone | 100-06-1 |
| L-borneol | 464-45-9 |
| 2,4-Hexadien-1-ol | 111-28-4 |
| D-Fenchone | 4695-62-9 |
| 3-Phenylpropyl formate | 104-64-3 |
| Cinnamyl formate | 104-65-4 |
| D-galacturonate | 685-73-4 |
| D-glucuronate | 1700908 |
| 5' IMP | 131-99-7 |
| 1-Methoxy-4-methylbenzene | 104-93-8 |
| 2-Methylbutanoic acid | 116-53-0 |
| 2,4,6-Tribromophenol | 118-79-6 |
| 3-Ethyl pyridine | 536-78-7 |
| Zinc acetate | 557-34-6 |
| Methyl pentanoate | 624-24-8 |
| Methylthioethane | 624-89-5 |
| 3-Penten-2-one | 625-33-2 |
| Glycocholic acid | 475-31-0 |
| m-Methoxybenzoic acid | 586-38-9 |
| alpha-Hydroxypropionic acid | 598-82-3 |
| Methyl 2-furoate | 611-13-2 |
| 2-Furancarboxylic acid, propyl ester | 615-10-1 |
| Benzylacetoacetic acid, ethyl ester | 620-79-1 |
| 2,5-Dimethyl pyrrole | 625-84-3 |
| 4-methyl-1,1'-biphenyl | 644-08-6 |
| p-Isopropylacetophenone | 645-13-6 |
| 4-methyl-thiazole | 693-95-8 |
| gamma-Decalactone | 706-14-9 |
| 2-acetylpyrrole | 1072-83-9 |
| 2-acetylpyridine | 1122-62-9 |
| tetramethyl-pyrazine | 1124-11-4 |
| Methyl 4-phenylbutyrate | 2046-17-5 |
| 2,3,6-trimethyl-phenol | 2416-94-6 |
| 2-Methoxypyrazine | 3149-28-8 |
| 2-Ethylfuran | 3208-16-0 |
| 2,3-dimethyl-pyrazine | 5910-89-4 |
| Thiophenethiol | 7774-74-5 |
| o-Tolyl isobutyrate | 36438-54-7 |
| cis-3-Hexenyl pyruvate | 68133-76-6 |
| cis-3-Hexenyl cis-3-hexenoate | 61444-38-0 |
| trans-2-Hexenyl isovalerate | 68698-59-9 |
| trans-2-Hexenyl formate | 53398-78-0 |
| trans-2-Hexenyl valerate | 56922-74-8 |
| 1-Octen-3-yl butyrate | 16491-54-6 |
| Methyl 4-(methylthio)butyrate | 53053-51-3 |
| 2,4-Octadien-1-ol | 18409-20-6 |
| 2,4-Nonadien-1-ol | 62488-56-6 |
| 2,4-Decadien-1-ol | 18409-21-7 |
| (e,z)-2,6-Nonadienyl acetate | 68555-65-7 |
| 3-Hexenal | 4440-65-7 |
| Tetrahydro-2-furanmethanol acetate | 637-64-9 |
| Methyl benzaldehyde | 1334-78-7 |
| Dodecylsulfonic acid | 1510-16-3 |
| Methylethyl disulfide | 4253-89-8 |
| Farnesol | 4602-84-0 |
| Thiobenzoic acid, S-methyl ester | 5925-68-8 |
| Hexyl benzoate | 6789-88-4 |
| 2,5-Diethyltetrahydrofuran | 41239-48-9 |
| Zinc hydrosulfite | 7779-86-4 |
| (2R,3S)-Tartaric Acid | 147-73-9 |
| Ethylsulfuric acid | 540-82-9 |
| 1,2,2-Trimethyl-1,3-cyclopentanedicarboxylic acid | 5394-83-2 |
| 2-Methyl-3-buten-2-ol | 115-18-4 |
| trans-2-Hexenal | 6728-26-3 |
| 4-Hexen-3-one | 2497-21-4 |
| 1-Hexen-3-ol | 4798-44-1 |
| 2-Methyl-1-butanethiol | 1878-18-8 |
| 4-Methylcyclohexanone | 589-92-4 |
| 3-Heptanol | 589-82-2 |
| o-methylanisole | 578-58-5 |
| trans-2-octenal | 2363-89-5 |
| 2,3,4-Trimethyl-3-pentanol | 3054-92-0 |
| Acetylacetaldehyde dimethyl acetal | 5436-21-5 |
| p-methylacetophenone | 122-00-9 |
| o-aminoacetophenone | 551-93-9 |
| 4-Propylphenol | 645-56-7 |
| 2,4-Dimethylanisole | 6738-23-4 |
| Benzyl methyl sulfide | 766-92-7 |

TABLE 9-continued

| Name | CAS # |
|---|---|
| Methyl phenylacetate | 101-41-7 |
| 4-Ethoxybenzaldehyde | 10031-82-0 |
| p-tolyl acetate | 140-39-6 |
| 2,6-Dimethoxyphenol | 91-10-1 |
| Isoborneol | 124-76-5 |
| Methyl 2-methoxybenzoate | 606-45-1 |
| Phenylacetaldehyde dimethyl acetal | 101-48-4 |
| 3-Phenylpropyl acetate | 122-72-5 |
| Ethyl 3-phenylpropionate | 2021-28-5 |
| Benzyl butyrate | 103-37-7 |
| Anisyl acetate | 104-21-2 |
| Isobutyl phenylacetate | 102-13-6 |
| p-vinylphenol | 2628-17-3 |
| o-tolyl acetate | 533-18-6 |
| 2,5-Dihydroxybenzoic acid | 490-79-9 |
| o-methoxyphenyl acetate | 613-70-7 |
| Lactobionic acid | 96-82-2 |
| Magnesium hydrogen phosphate trihydrate | 7782-75-4 |
| Iberverin | 505-79-3 |
| alpha-methylcinnamaldehyde | 101-39-3 |
| benzyl phenylacetate | 102-16-9 |
| 1,3-dimercaptopropane | 109-80-8 |
| p-cymen-8-ol | 1197-01-9 |
| phenethyl anthranilate | 133-18-6 |
| trihydroxybutyrophenone | 1421-63-2 |
| o-methoxycinnamaldehyde | 1504-74-1 |
| 3-propylidene phthalide | 17369-59-4 |
| trans,trans-2,4-decadienal | 25152-84-5 |
| piperonyl acetate | 326-61-4 |
| 2,3-hexanedione | 3848-24-6 |
| isopropyl phenylacetate | 4861-85-2 |
| ethyl 3-hydroxybutyrate | 5405-41-4 |
| furfural acetone | 623-15-4 |
| beta-(2-furyl)acrolein | 623-30-3 |
| linalyl anthranilate | 7149-26-0 |
| citral diethyl acetal | 7492-66-2 |
| allyl anthranilate | 7493-63-2 |
| acetyl tributyl citrate | 77-90-7 |
| butyl anthranilate | 7756-96-9 |
| cyclohexyl anthranilate | 7779-16-0 |
| isoamyl cinnamate | 7779-65-9 |
| isobutyl anthranilate | 7779-77-3 |
| carvyl acetate | 97-42-7 |
| carveol | 99-48-9 |
| 3-(Methylthio)propionaldehyde | 3268-49-3 |
| Alpha-damascone | 43052-87-5 |
| Dimethyldicarbonate | 4525-33-1 |
| Procaine | 59-46-1 |
| 5-hydroxy-6-methyl-3,4-pyridinedimethanol | 65-23-6 |
| 2-methoxy-Naphthalene | 93-04-9 |
| Methyl nicotinate | 93-60-7 |
| Ethyl benzoylacetate | 94-02-0 |
| Phenethyl benzoate | 94-47-3 |
| 2-methyl-pentanoic acid | 97-61-0 |
| Cyclohexanecarboxylic acid | 98-89-5 |
| Methyl b-phenylpropionate | 103-25-3 |
| Benzyl 3-methyl butanoate | 103-38-8 |
| Naphthalene-2-sulfonic acid | 120-18-3 |
| Methyl 4-methoxybenzoate | 121-98-2 |
| 3-Phenylprop-2-enyl cinnamate | 122-69-0 |
| 7-methyl-3-methylene-1,6-Octadiene | 123-35-3 |
| Levulinic acid | 123-76-2 |
| 2-Mercaptobenzoic acid | 147-93-3 |
| m-Dimethoxybenzene | 151-10-0 |
| 3-butyl-1(3H)-isobenzofuranone | 6066-49-5 |
| 5-Methylquinoxaline | 13708-12-8 |
| 2-Ethyl Pyrazine | 13925-00-3 |
| trimethyl-pyrazine | 14667-55-1 |
| 2-ethyl-3-methyl-pyrazine | 15707-23-0 |
| 2,3-diethyl-pyrazine | 15707-24-1 |
| 2,3-diethyl-5-methyl-pyrazine | 18138-04-0 |
| 2-Methylthiopyrazine | 21948-70-9 |
| 5-Methyl-3H-furan-2-one | 591-12-8 |
| cis-3-Hexen-1-ol | 928-96-1 |
| 3,7-Dimethyl-1,3,6-octatriene | 13877-91-3 |
| calcium cyclamate | 139-06-0 |
| aconitic acid | 499-12-7 |
| 2-Dehydrolinalool | 29171-20-8 |
| 2-Mercaptopropionic acid | 79-42-5 |
| 3-Methyl-2-butenal | 107-86-8 |
| Allylacetic acid | 591-80-0 |
| Allyl cyclohexylacetate | 4728-82-9 |
| Allyl cyclohexylpropionate | 2705-87-5 |
| Allyl phenoxyacetate | 7493-74-5 |
| Allyl phenylacetate | 1797-74-6 |
| Allyl alpha-ionone | 79-78-7 |
| Butyl butyrolactate | 7492-70-8 |
| Cinnamyl isobutyrate | 103-59-3 |
| Cinnamyl propionate | 103-56-0 |
| Dibenzyl disulfide | 150-60-7 |
| Isobornyl acetate | 125-12-2 |
| Methyl heptyne carbonate | 111-12-6 |
| Triethyl citrate | 77-93-0 |
| gamma-Undecalactone | 104-67-6 |
| alpha-Amylcinnamyl alcohol | 101-85-9 |
| 1,3,4,6,7,8-Hexahydro-4,6,6,7,8,8-hexamethyl cyclopenta[g][2]benzopyran | 1222-05-5 |
| 2-Ethylbutyl acetate | 10031-87-5 |
| Triphosphoric acid, pentapotassium salt | 13845-36-8 |
| L-(+)-Lactic acid | 79-33-4 |
| Mannitol | 87-78-5 |
| 2-Methoxy-4-methylphenol | 93-51-6 |
| 1,2,3-Propanetricarboxylic acid, 2-hydroxy-, disodium salt | 144-33-2 |
| Ethanesulfonic acid, 2-hydroxy-, monosodium salt | 1562-00-1 |
| 2-Methoxy-4-propylphenol | 2785-87-7 |
| 3,7-Dimethyl-3-octanol | 78-69-3 |
| 2-Pentyl furan | 3777-69-3 |
| Butanoic acid, 3-oxo-, butyl ester | 591-60-6 |
| 4-(4-Hydroxy-4-methyl pentyl)-3-cyclohexene-1-carboxaldehyde | 31906-04-4 |
| Methyl 3-oxo-2-pentylcyclopentaneacetate | 24851-98-7 |
| Naphthalene, 2-(2-methylpropoxy)- | 2173-57-1 |
| Perillol | 536-59-4 |
| 2-Acetyl-1-methylpyrrole | 932-16-1 |
| 4-Allyl-2,6-dimethoxyphenol | 6627-88-9 |
| Butyl levulinate | 2052-15-5 |
| D-(+)-Camphoric acid | 124-83-4 |
| D(+)-10-Camphorsulfonic acid | 3144-16-9 |
| L-(−)-Carvone | 6485-40-1 |
| (−)-Carvyl propionate | 97-45-0 |
| (−)-Caryophyllene oxide | 1139-30-6 |
| Cyclohexylacetic acid | 5292-21-7 |
| 3-Cyclopentylpropionic acid | 140-77-2 |
| (−)-Dihydrocarvyl acetate | 20777-49-5 |
| 3,3-Dimethylacrylic acid | 541-47-9 |
| 2,4-Dimethylbenzaldehyde | 15764-16-6 |
| 1,4-Dithiane-2,5-dial | 40018-26-6 |
| Ethanesulfonic acid | 594-45-6 |
| Ethyl butyrylacetate | 3249-68-1 |
| Ethyl (methylthio)acetate | 4455-13-4 |
| Ethyl pyruvate | 617-35-6 |
| Ethyl sorbate | 2396-84-1 |
| 5-Formyl-2-furansulfonic acid, sodium salt | 31795-44-5 |
| Furfuryl mercaptan | 98-02-2 |
| 1,6-Hexanedithiol | 1191-43-1 |
| trans-2-Hexenoic acid | 13419-69-7 |
| trans-2-Hexen-1-ol | 928-95-0 |
| 4-(4-Hydroxyphenyl)-2-butanone | 5471-51-2 |
| Isopulegol | 89-79-2 |
| Isopulegyl acetate | 89-49-6 |
| 2-Ketobutyric acid | 600-18-0 |
| (−)-Limonene | 5989-54-8 |
| 4-Methoxyphenylacetone | 122-84-9 |
| Methyl cyclohexanecarboxylate | 4630-82-4 |
| 3-Methylcyclohexanone | 591-24-2 |
| 3-Methyl-2-cyclohexen-1-one | 1193-18-6 |
| 3-Methyl-1,2-cyclopentanedione | 765-70-8 |
| 3-Methyl-2-cyclopenten-1-one | 2758-18-1 |
| N-Methyl-D-glucamine | 6284-40-8 |
| Methyl 3 (methylthio) propionate | 13532-18-8 |
| 4-Methyl-5-thiazoleethanol | 137-00-8 |
| 5-Methyl-2-thiophenecarboxaldehyde | 13679-70-4 |
| DL-3-Methylvaleric acid | 105-43-1 |
| (−)-Myrtenal | 564-94-3 |
| Nopol | 128-50-7 |

TABLE 9-continued

| Name | CAS # |
|---|---|
| gamma-Octanoic lactone | 104-50-7 |
| 3-Octanol | 589-98-0 |
| E-2-Octenoic acid | 1871-67-6 |
| Pamoic acid | 130-85-8 |
| 4-Phenyl-2-butyl acetate | 10415-88-0 |
| 1-Phenyl-1,2-propanedione | 579-07-7 |
| 2-Phenylpropyl butyrate | 80866-83-7 |
| 2-Phenylpropyl isobutyrate | 65813-53-8 |
| cis-2-Hexen-1-ol | 928-94-9 |
| Bis(methylthio)methane | 1618-26-4 |
| Magnesium carbonate hydroxide, Light | 39409-82-0 |
| N-Acetyl-L-methionine | 65-82-7 |
| 4-Methyl-5-vinylthiazole | 1759-28-0 |
| 2-Methyl-1-phenyl-2-propanol | 100-86-7 |
| 3-Methylpropionaldehyde | 104-53-0 |
| N-Benzyl-2-phenylethylamine | 3647-71-0 |
| 1-Phenylethyl propionate | 120-45-6 |
| 3-Phenylpropyl isobutyrate | 103-58-2 |
| Allyl hexanoate | 123-68-2 |
| alpha, 4-Dimethylbenzylalcohol | 536-50-5 |
| (−)-Menthyl lactate | 59259-38-0 |
| 2,6-Dimethylthiophenol | 118-72-9 |
| 2,4,5-Trimethylthiazole | 13623-11-5 |
| Ethyl 3-(methylthio)propionate | 13327-56-5 |
| Phenylethyl isovalerate | 140-26-1 |
| 2-Propylpyrazine | 18138-03-9 |
| 2-Methyltetrahydrofuran-3-one | 3188-00-9 |
| Ethyl 2-(methyldithio)propionate | 23747-43-5 |
| 3,4-Dimethyl-1,2-cyclopentanedione | 13494-06-9 |
| Difurfurylsulfide | 13678-67-6 |
| Difurfuryldisulfide | 4437-20-1 |
| 3-(Methylthio)propanol | 505-10-2 |
| Methyl phenyl disulfide | 14173-25-2 |
| 2-(Methyldithio)-isobutyraldehyde | 67952-60-7 |
| Methyl 2-thiofuroate | 13679-61-3 |
| 2-Isobutylthiazole | 18640-74-9 |
| 4-Methyl-5-thiazolylethyl acetate | 656-53-1 |
| 2-Acetylthiazole | 24295-03-2 |
| 2-Ethyl-3,5 (6)-dimethylpyrazine | 27043-05-6 |
| 5-Methyl-6,7-dihydro-5H-cyclopenta(b)pyrazine | 23747-48-0 |
| Cinnamyl acetate | 103-54-8 |
| 2,5-Dihydroxy-2,5-dimethyl-1,4-dithiane | 55704-78-4 |
| 5,6,7,8-Tetrahydroquinoxaline | 34413-35-9 |
| 2-Methyl-3-furanethiol | 28588-74-1 |
| Styrallyl acetate | 93-92-5 |
| 2-Methylhexanoic acid | 4536-23-6 |
| 2-Methylheptanoic acid | 1188-02-9 |
| 2,2,6-Trimethylcyclohexanone | 2408-37-9 |
| L-Tyrosine ethyl ester hydrochloride | 4089--07-0 |
| Ethyl 4-methoxybenzoate | 94-30-4 |
| 4-Ethylbenzaldehyde | 4748-78-1 |
| N-Ethyl-p-menthane-3-carboxamide | 39711-79-0 |
| 1-(2-Furyl)-1,3-butanedione | 25790-35-6 |
| Menthofuran | 494-90-6 |
| Methylsulfuric acid sodium salt | 512-42-5 |
| Sucrose diacetate hexaisobutyrate | 126-13-6 |
| N,2,3-Trimethyl-2-isopropylbutamide | 51115-67-4 |
| Tripropionin | 139-45-7 |
| (+/−)-Citronellic acid | 502-47-6 |
| 5-Acetyl-2,4-dimethylthiazole | 38205-60-6 |
| Neryl acetate | 141-12-8 |
| Benzyl propionate | 122-63-4 |
| 1R-(−)-Camphorsulfonic acid | 35963-20-3 |
| 3,4-Hexanedione | 4437-51-8 |
| cis-3-Hexenoic acid | 4219-24-3 |
| cis-4-Heptenal | 6728-31-0 |
| (E,)-2,6-nonadienal | 557-48-2 |
| trans-2,trans-6-Nonadienal | 17587-33-6 |
| 4-Methyl-2-pentenal | 5362-56-1 |
| cis-6-Nonenal | 2277-19-2 |
| Methyl propyl disulfide | 2179-60-4 |
| 8-p-Menthen-1-ol | 138-87-4 |
| p-Menthan-2-one | 499-70-7 |
| Bisabolene | 495-62-5 |
| Ethyl cyclohexanecarboxylate | 3289-28-9 |
| Phenylpyruvate | 156-06-9 |
| Hydroxypyruvate | 1113-60-6 |
| 4-Methyl-2-oxopentanoate | 816-66-0 |
| (+)-Neomenthol | 2216-52-6 |
| trans-Citral | 141-27-5 |
| Piperitenone | 491-09-8 |
| Sabinene hydrate | 546-79-2 |
| Perillyl aldehyde | 2111-75-3 |
| 2-Hydroxyethanesulfonate | 107-36-8 |
| Acetyl isovaleryl | 13706-86-0 |
| Acetyl valeryl | 96-04-8 |
| Butylidene phthalide | 551-08-6 |
| Carvacryl ethyl ether | 4732-13-2 |
| Ethyl vanillin propylene glycol acetal | 68527-76-4 |
| Hexyl hexanoate | 6378-65-0 |
| 2-Methyl-5-(methylthio)-furan | 13678-59-6 |
| 2-Methyl-4-pentenoic acid | 1575-74-2 |
| 2-Methyl-4-propyl-1,3-oxathiane | 67715-80-4 |
| 3-Methylthio-1-hexanol | 51755-66-9 |
| cis-6-Nonenol | 35854-86-5 |
| Rose oxide | 16409-43-1 |
| L-Linalool | 126-91-0 |
| 5,6-Dimethyl-8-isopropenylbicyclo[4.4.0]dec-1-en-3-one | 4674-50-4 |
| 2-Ethyl-3,5-dimethylpyrazine | 13925-07-0 |
| 2-Isopropylpyrazine | 29460-90-0 |
| 2-Isobutyl-3-methyl-pyrazine | 13925-06-9 |
| 2-Methoxy-3-sec-butyl-pyrazine | 24168-70-5 |
| 2-Methylthio-3(6)-methyl-pyrazine | 67952-65-2 |
| Benzylcarbinyl propionate | 122-70-3 |
| Bornyl acetate | 76-49-3 |
| furaneol | 3658-77-3 |
| Methoxycinnamaldehyde | 1963-36-6 |
| Methylphenol, hydrogen sulfate | 68127-34-4 |
| Lactitol monohydrate | 81025-04-9 |
| 2H-Pyrrole, 3,4-dihydro- | 5724-81-2 |
| 2-Butenal, 2-methyl-, (E)- | 497-03-0 |
| 2-Pentenal | 764-39-6 |
| Ethanethioic acid, S-methyl ester | 1534-08-3 |
| 2-Hexenal | 505-57-7 |
| 2-Methyl-2-pentenal | 623-36-9 |
| Cyclopentanethiol | 1679-07-8 |
| Butane, 2-ethoxy- | 2679-87-0 |
| S-Ethyl thioacetate | 625-60-5 |
| ethyl methyl carbonate | 623-53-0 |
| 3(2H)-Furanone, 2,5-dimethyl- | 14400-67-0 |
| Allyl propionate | 2408-20-0 |
| methyl 2-methylbutanoate | 868-57-5 |
| 2-Butanone, 1-(methylthio)- | 13678-58-5 |
| Ethanethioic acid, S-propyl ester | 2307-10-0 |
| 1,2-Butanedithiol | 16128-68-0 |
| 6-Methyl-3,5-heptadiene-2-one | 1604-28-0 |
| 2-Octen-4-one | 4643-27-0 |
| 2,5-dimethyl-3-furanthiol | 55764-23-3 |
| 2-Heptenoic acid | 18999-28-5 |
| Butanoic acid, 2-propenyl ester | 2051-78-7 |
| 6-Methyl-5-hepten-2-ol | 1569-60-4 |
| trans-2-Octen-4-ol | 20125-81-9 |
| cis-3-Octen-1-ol | 20125-84-2 |
| 1-Butanol, 2-methyl-, acetate | 624-41-9 |
| 4-methyl-alpha-methylstyrene | 1195-32-0 |
| trans-3-Phenyl-2-propen-1-ol | 4407-36-7 |
| Benzeneacetaldehyde, alpha-methyl- | 93-53-8 |
| Benzene, (2-methoxyethyl)- | 3558-60-9 |
| Cyclohexene, 1-methyl-4-(1-methylethenyl)-, (+−)- | 7705-14-8 |
| Phenol, 2-(methylthio)- | 1073-29-6 |
| 2-Hexen-1-yl acetate | 2497-18-9 |
| 3-Hexen-1-ol, acetate, (Z)- | 3681-71-8 |
| 5-Hydroxy-4-octanone | 496-77-5 |
| butyl 2-methylpropanoate | 97-87-0 |
| Benzofuran-2-carboxaldehyde | 4265-16-1 |
| DL-Lysine | 70-54-2 |
| 1-Hexanethiol, 2-ethyl- | 7341-17-5 |
| 2',4'-Dimethylacetophenone | 89-74-7 |
| 2-Pentylpyridine | 2294-76-0 |
| 1-Methoxy-4-propyl benzene | 104-45-0 |
| 1-Hydroxy-2-methoxy-4-ethyl benzene | 2785-89-9 |
| Nonalactone | 6008-27-1 |
| Cyclohexyl propionate | 6222-35-1 |
| Allyl 2-ethylbutyrate | 7493-69-8 |
| Butanoic acid, 3-oxo-, 2-methylpropyl ester | 7779-75-1 |

TABLE 9-continued

| Name | CAS # |
|---|---|
| n-Butyl pentanoate | 591-68-4 |
| 3,7-Dimethyl-1-octanol | 106-21-8 |
| 3-Buten-2-one, 3-methyl-4-phenyl- | 1901-26-4 |
| 2-Propenoic acid, 3-phenyl-, methyl ester, (E)- | 1754-62-7 |
| Benzene, 4-ethenyl-1,2-dimethoxy- | 6380-23-0 |
| Benzenepropanol, alpha,alpha-dimethyl- | 103-05-9 |
| Benzene, (butoxymethyl)- | 588-67-0 |
| Dimethyl anthranilate | 85-91-6 |
| 2-Hexanoylfuran | 14360-50-0 |
| Cyclohexyl butyrate | 1551-44-6 |
| Naphthalene, 2-ethoxy- | 93-18-5 |
| Acetoacetic acid isoamyl ester | 2308-18-1 |
| Propanoic acid, 2-methyl-, 4-methylphenyl ester | 103-93-5 |
| 4-(4-Methoxyphenyl)-2-butanone | 104-20-1 |
| Isobutyl benzoate | 120-50-3 |
| Benzene, 1,2-dimethoxy-4-(1-propenyl)- | 93-16-3 |
| Beta-Phenylethylmethylethylcarbinol | 10415-87-9 |
| 1,1-Dimethoxy-2-phenylpropane | 90-87-9 |
| Geranyl formate | 105-86-2 |
| Bornyl formate | 7492-41-3 |
| 6-Octen-1-ol, 3,7-dimethyl-, formate | 105-85-1 |
| Benzeneacetic acid, butyl ester | 122-43-0 |
| 3,5,9-Undecatrien-2-one, 6,10-dimethyl- | 141-10-6 |
| Anisyl propionate | 7549-33-9 |
| Butanoic acid, 3-phenyl-2-propenyl ester | 103-61-7 |
| 2-Propenoic acid, 3-phenyl-, 2-methylpropyl ester | 122-67-8 |
| Eugenyl acetate | 93-28-7 |
| 3-Methylbutyl phenylacetate | 102-19-2 |
| Benzoic acid, 2-(methylamino)-, 2-methylpropyl ester | 65505-24-0 |
| Phenoxy ethyl isobutyrate | 103-60-6 |
| Anisyl butyrate | 6963-56-0 |
| 2,6-Octadien-1-ol, 3,7-dimethyl-, propanoate, (Z)- | 105-91-9 |
| Isobornyl propionate | 2756-56-1 |
| 1,3,5-Trithiane, 2,2,4,4,6,6-hexamethyl- | 828-26-2 |
| Geranyl N-butyrate | 106-29-6 |
| Geranyl isobutyrate | 2345-26-8 |
| Thiophene, 2,2'-dithiobis- | 6911-51-9 |
| 2-Propenoic acid, 3-phenyl-, cyclohexyl ester | 7779-17-1 |
| Benzeneacetic acid, 3-phenyl-2-propenyl ester | 7492-65-1 |
| Anisyl phenylacetate | 102-17-0 |
| 2-Propenoic acid, 3-phenyl-, 3-phenylpropyl ester | 122-68-9 |
| Geranyl phenylacetate | 102-22-7 |
| hexyl 2-methylbutyrate | 10032-15-2 |
| 4-heptanolide | 105-21-5 |
| Neral | 106-26-3 |
| (E)-2-octenol | 18409-17-1 |
| Ethyl 3-hydroxyhexanoate | 2305-25-1 |
| isopropyl hexanoate | 2311-46-8 |
| hexyl butanoate | 2639-63-6 |
| bis(2-methyl-3-furyl)disulfide | 28588-75-2 |
| 3-hydroxy-4,5-dimethyl-2(5H)-furanone | 28664-35-9 |
| 2-acetyl-2-thiazoline | 29926-41-8 |
| (E,E)-2,4-octadienal | 30361-28-5 |
| geranyl acetone | 3796-70-1 |
| 1-octen-3-one | 4312-99-6 |
| 3-mercapto-2-pentanone | 67633-97-0 |
| (Z)-3-hexenal | 6789-80-6 |
| 4-hexanolide | 695-06-7 |
| 5-octanolide | 698-76-0 |
| delta-decalactone | 705-86-2 |
| 4-vinylguaiacol | 7786-61-0 |
| Amyl salicylate | 2050-08-0 |
| Cyclohexyl formate | 4351-54-6 |
| Dimethylbenzylcarbinyl acetate | 151-05-3 |
| Geranyl propionate | 105-90-8 |
| Terpinyl acetate | 80-26-2 |
| isopropyl 3-methylbutanoate | 32665-23-9 |
| isopropyl 2-methylbutanoate | 66576-71-4 |
| 3-Hexenyl 3-methylbutanoate | 10032-11-8 |
| Isoamyl 2-methylbutyrate | 27625-35-0 |
| 3-Octyl acetate | 4864-61-3 |
| Benzyl isobutyrate | 103-28-6 |
| Cis-3-hexenyl butyrate | 16491-36-4 |
| Cis-3-hexenyl lactate | 61931-81-5 |
| Citronellyl butyrate | 141-16-2 |
| Citronellyl propionate | 141-14-0 |
| Isoamyl hexanoate | 2198-61-0 |
| 1,3,5-Undecatriene | 16356-11-9 |
| 1-Benzyloxy-2-methoxy-4-propenyl benzene | 120-11-6 |
| 1-Octen-3-yl acetate | 198242 |
| 2-Acetyl-3-ethyl pyrazine | 32974-92-8 |
| 2-Isopropyl-4-methyl thiazole | 15679-13-7 |
| 2-Methyl-2-pentenoic acid | 3142-72-1 |
| 2-sec-butyl thiazole | 18277-27-5 |
| 4,5-Dimethyl thiazole | 3581-91-7 |
| 4-(2,6,6-Trimethyl-2-cyclohexen-1-yl)butan-2-one | 31499-72-6 |
| 4-(2,6,6-Trimethyl cyclohexa-1,3-dienyl)but-2-en-4-one | 23696-85-7 |
| Acetaldehyde phenethyl propyl acetal | 7493-57-4 |
| Acetaldehyde ethyl cis-3-hexenyl acetal | 28069-74-1 |
| Acetone propylene glycol acetal | 1193-11-9 |
| Acetyl isoeugenol | 93-29-8 |
| 2-Acetyl-5-methyl furan | 1193-79-9 |
| Allyl cyclohexylbutyrate | 7493-65-4 |
| Alpha, alpha-dimethylphenethyl butyrate | 10094-34-5 |
| Alpha,alpha-dimethyl phenethyl formate | 10058-43-2 |
| Alpha,beta-santalol | 11031-45-1 |
| Alpha-amyl cinnamaldehyde dimethyl acetal | 91-87-2 |
| Alpha-fenchyl acetate | 13851-11-1 |
| Alpha-furfuryl pentanoate | 36701-01-6 |
| Alpha-ionol | 25312-34-9 |
| 6-Methyl-alpha-ionone | 79-69-6 |
| Alpha-methyl-pisopropylphenylpropanaldehyde acetate | 103-95-7 |
| | 7493-78-9 |
| Alpha-piperitone | 6091-50-5 |
| Alpha-n-amyl-beta-phenyl acryl isovalerate | 7493-80-3 |
| 6-Amyl-alpha-pyrone | 27593-23-3 |
| Anisyl formate | 122-91-8 |
| Benzylcarbinyl 2-methyl butyrate | 24817-51-4 |
| Benzylcarbinyl 3-phenyl propenoate | 103-53-7 |
| Benzylcarbinyl alpha--toluate | 102-20-5 |
| Benzylcarbinyl butyrate | 103-52-6 |
| Benzylcarbinyl caproate | 6290-37-5 |
| Benzylcarbinyl formate | 104-62-1 |
| Benzylcarbinyl isobutyrate | 103-48-0 |
| Benzylcarbinyl salicylate | 87-22-9 |
| Benzylcarbinyl tiglate | 55719-85-2 |
| Benzyl dipropyl ketone | 7492-37-7 |
| Benzyl tiglate | 37526-88-8 |
| Beta-homocyclocitral | 472-66-2 |
| Beta-ionol | 22029-76-1 |
| 3-Phenylpropyl propanoate | 122-74-7 |
| Bois de rose oxide | 7392-19-0 |
| Butyl 2-methyl butyrate | 15706-73-7 |
| Butyl cinnamate | 538-65-8 |
| ortho-sec-Butyl cyclohexanone | 14765-30-1 |
| isobutyl cis-2-methyl-2-butenoate | 7779-81-9 |
| 5-n-Butyl-delta-valerolactone | 3301-94-8 |
| Campholenic aldehyde | 4501-58-0 |
| Cedran-8-yl acetate | 77-54-3 |
| Cinnamyl isovalerate | 140-27-2 |
| Cis-3-hexenyl benzoate | 25152-85-6 |
| Cis-3-hexenyl caproate | 31501-11-8 |
| Cis-3-hexenyl formate | 33467-73-1 |
| Cis-3-hexenyl isobutyrate | 41519-23-7 |
| Cis-3-hexenyl phenylacetate | 42436-07-7 |
| Cis-3-hexenyl propionate | 33467-74-2 |
| Cis-3-hexenyl tiglate | 67883-79-8 |
| Cis-3-hexenyl valerate | 35852-46-1 |
| cis-4-Hepten-1-ol | 6191-71-5 |
| Cis-5-octen-1-ol | 64275-73-6 |
| Citral dimethyl acetal | 7549-37-3 |
| Citronellyl isobutyrate | 97-89-2 |
| Citronellyl isovalerate | 68922-10-1 |
| Citronellyl valerate | 7540-53-6 |
| Citroxide | 7416-35-5 |
| Cocal | 21834-92-4 |
| p-Cresyl alpha-toluate | 101-94-0 |
| p-Cresyl isovalerate | 55066-56-3 |
| Dehydro-beta-cyclocitral | 116-26-7 |
| 8,8-Diethoxy--2,6-dimethyl-2-octanol | 7779-94-4 |
| 5,7-Dihydro-2-methyl thieno(3,4-d)pyrimidine | 36267-71-7 |
| 2,5-Dihydro-4,5-dimethyl-2-(2-methyl propyl)thiazole | 65894-83-9 |
| Dihydrojasmone | 1128-08-1 |

TABLE 9-continued

| Name | CAS # |
|---|---|
| Dihydroxyacetophenone | 28631-86-9 |
| 1,1-Dimethoxy-3,7-dimethyl-7-octanol | 141-92-4 |
| 3,7-Dimethyl-1,6-octadien-3-yl benzoate | 126-64-7 |
| 3,7-Dimethyl-1,6-octadien-3-yl butyrate | 78-36-4 |
| 3,7-Dimethyl-1,6-octadien-3-yl isobutyrate | 78-35-3 |
| 3,7-Dimethyl-1,6-octadien-3-yl propanoate | 144-39-8 |
| cis-3,7-Dimethyl-2,6-octadien-1-yl 2-methyl propanoate | 2345-24-6 |
| 2,4-Dimethyl-3-cyclohexene-1-carboxaldehyde | 68039-49-6 |
| 2,6-Dimethyl-5-hepten-1-al | 106-72-9 |
| trans,cis-2,6-Dodecadien-1-al | 21662-13-5 |
| Eglantal | 26643-91-4 |
| Ethyl E-2-hexenoate | 27829-72-7 |
| Ethyl tiglate | 5837-78-5 |
| Ethyl trans-4-decenoate | 76649-16-6 |
| 5-Ethyl-4-hydroxy-2-methyl-3[2H]furanone | 27538-09-6 |
| 2-Ethyl-4-methyl thiazole | 15679-12-6 |
| 2,6,10-Trimethyl-2,6,10-pentadecatrien-14-one | 762-29-8 |
| Guaiacyl phenyl acetate | 4112-89-4 |
| 3-Hepten-2-one | 1119-44-4 |
| trans-2-Hexen-1-ol | 2305-21-7 |
| Trans-2-hexenyl butyrate | 53398-83-7 |
| Hexyl phenylacetate | 5421-17-0 |
| Hexyl propionate | 2445-76-3 |
| Hydroxycitronellol | 107-74-4 |
| Isobutyl 2-butenoate | 589-66-2 |
| Isobutyl salicylate | 87-19-4 |
| Isodihydro lavandulal | 35158-25-9 |
| Isoeugenyl phenyl acetate | 120-24-1 |
| Isopropyl alpha-methylcrotonate | 1733-25-1 |
| p-Menth-1-en-8-yl propionate | 80-27-3 |
| Menthalactone | 13341-72-5 |
| 3-Methoxy-p-cymene | 1076-56-8 |
| Methyl 4-methyl pentanoate | 2412-80-8 |
| alpha-Methyl benzyl formate | 7775-38-4 |
| 2-Methylbutyl 2-methylbutanoate | 2445-78-5 |
| Methyl e-2-octenoate | 2396-85-2 |
| p-Methyl hydratropaldehyde | 99-72-9 |
| 3-(5-Methyl-2-furyl)butanal | 31704-80-0 |
| Nerol oxide | 1786-08-9 |
| trans,cis-2,6-Nonadien-1-ol | 7786-44-9 |
| trans-2-Octen-1-yl acetate | 3913-80-2 |
| 3-Octen-2-one | 1669-44-9 |
| 2-Phenyl-2-butenal | 4411-89-6 |
| 2-Propionylthiazole | 43039-98-1 |
| 1-Hydroxy-2-butanone | 5077-67-8 |
| 2-Butanone, 3-hydroxy-, (+−)- | 52217-02-4 |
| Thiazole, 2,5-dimethyl- | 4175-66-0 |
| Butanethioic acid, S-methyl ester | 2432-51-1 |
| 2,4-Hexadienoic acid, methyl ester, (E,E)- | 689-89-4 |
| Benzeneacetaldehyde, 4-methyl- | 104-09-6 |
| Bicyclo[4.1.0]hept-3-ene, 3,7,7-trimethyl-, (1S)- | 498-15-7 |
| Ethyl 3-hexenoate | 2396-83-0 |
| 1H-Pyrrole, 1-(2-furanylmethyl)- | 1438-94-4 |
| 6-Octenal, 3,7-dimethyl-, (R)- | 2385-77-5 |
| Ethanethioic acid, S-(2-furanylmethyl) ester | 13678-68-7 |
| 6-Octen-1-ol, 3,7-dimethyl-, (R)- | 1117-61-9 |
| 6-Octen-1-ol, 3,7-dimethyl-, (S)- | 7540-51-4 |
| DL-Tetrahydrofurfuryl propionate | 637-65-0 |
| Benzenepentanol | 10521-91-2 |
| Cyclohexaneethanol, acetate | 21722-83-8 |
| Benzyl isobutyl ketone | 5349-62-2 |
| Butanoic acid, 3-oxo-, phenylmethyl ester | 5396-89-4 |
| 1,2-Ethanediamine, N,N″-bis(phenylmethyl)- | 140-28-3 |
| 2-Ethyl-3-hydroxy-4-pyrone | 1110651 |
| Dicyclohexyl disulfide | 2550-40-5 |
| Tetrahydrofurfuryl butyrate | 2217-33-6 |
| Thujone | 546-80-5 |
| Benzyl alcohol, alpha-methyl-, butyrate | 3460-44-4 |
| Citronellyl tiglate | 24717-85-9 |
| Lactitol | 585-86-4 |
| Nonivamide | 2444-46-4 |
| 2-Acetoxy-3-butanone | 4906-24-5 |
| 3-Acetyl-2,5-dimethylthiophene | 230378 |
| 3-Acetyl-2,5dimethylfuran | 10599-70-9 |
| 4-Acetyl-6-t-butyl-1,1-dimethylindan | 13171-00-1 |
| Allyl 2-furoate | 4208-49-5 |
| Allyl sorbate | 7493-75-6 |
| Allyl thiopropionate | 41820-22-8 |
| Allyl tiglate | 7493-71-2 |
| Amylcyclohexyl acetate | 67874-72-0 |
| Benzaldehyde glyceryl acetal | 1319-88-6 |
| Benzaldehyde propylene glycol acetal | 2568-25-4 |
| Bornyl isovalerate | 76-50-6 |
| 1,3-Butanedithiol | 24330-52-7 |
| 2,3-Butanedithiol | 4532-64-3 |
| Butyl cinnamic aldehyde | 7492-44-6 |
| Cinnamyl benzoate | 5320-75-2 |
| Citral ethylene glycol acetal | 66408-78-4 |
| Citronellyloxyacetaldehyde | 7492-67-3 |
| Citronellyl phenylacetate | 139-70-8 |
| Cyclohexyl isovalerate | 7774-44-9 |
| Decalactone | 5579-78-2 |
| 2,5-Dimethyl-4-methoxy-3(2H)-furanone | 4077-47-8 |
| 6,10-Dimethyl-9-undecen-2-one | 4433-36-7 |
| 2-Ethoxythiazole | 15679-19-3 |
| Ethyl 2-mercaptopropionate | 19788-49-9 |
| Ethyl 2-methyl-4-pentenoate | 53399-81-8 |
| Ethyl 3-(2-furyl)propanoate | 94278-27-0 |
| Ethyl cyclohexanepropionate | 10094-36-7 |
| Ethyl (p-tolyloxy)acetate | 67028-40-4 |
| 3-Ethyl-2-hydroxy-2-cyclopenten-1-one | 21835-01-8 |
| Ethylene brassylate | 105-95-3 |
| 2-Ethylfenchol | 18368-91-7 |
| Furfuryl 3-methylbutanoate | 13678-60-9 |
| Furfuryl butyrate | 623-21-2 |
| Furfuryl isopropyl sulfide | 1883-78-9 |
| Furfuryl methyl sulfide | 1438-91-1 |
| Furfuryl propionate | 623-19-8 |
| Furfuryl thiopropionate | 59020-85-8 |
| Geranyl acetoacetate | 10032-00-5 |
| Geranyl benzoate | 94-48-4 |
| Geranyl isovalerate | 109-20-6 |
| delta-Hexalactone | 823-22-3 |
| trans-3-Hexenal | 69112-21-6 |
| cis-3-Hexenyl anthranilate | 65405-76-7 |
| trans-2-Hexenyl propionate | 53398-80-4 |
| 5-(cis-3-Hexenyl) dihydro-5-methyl-2(3H)furanone | 70851-61-5 |
| Hexyl 2-formate | 39251-86-0 |
| Hexyl crotonate | 19089-92-0 |
| Hexyl formate | 629-33-4 |
| Isoamyl 3-(2-furyl)propionate | 7779-67-1 |
| Isoamyl pyruvate | 7779-72-8 |
| Isobutyl furylpropionate | 105-01-1 |
| Isohexenyl cyclohexenyl carboxaldehyde | 37677-14-8 |
| p-isopropyl phenylacetaldehyde | 4395-92-0 |
| Linalyl cinnamate | 78-37-5 |
| Linalyl formate | 115-99-1 |
| Linalyl isovalerate | 1118-27-0 |
| Linalyl phenylacetate | 7143-69-3 |
| Maltol isobutyrate | 65416-14-0 |
| Methyl 2-methylpentanoate | 2177-77-7 |
| Methyl 3-hydroxyhexanoate | 21188-58-9 |
| Methyl 3-nonenoate | 13481-87-3 |
| Methyl furfuryl disulfide | 57500-00-2 |
| Methyl p-tert butylphenylacetate | 3549-23-3 |
| 3-Methyl-1,2-cyclohexanedione | 3008-43-3 |
| alpha-Methylanisalacetone | 104-27-8 |
| 2-Methylbutyl isovalerate | 2445-77-4 |
| 4-Methylnonanoic acid | 45019-28-1 |
| 4-Methyloctanoic acid | 54947-74-9 |
| 2-Methyltetrahydrothiophen-3-one | 13679-85-1 |
| 3-(Methylthio)butanal | 16630-52-7 |
| 4-(Methylthio)butanol | 20582-85-8 |
| 4-Methylthio-2-butanone | 34047-39-7 |
| 4-Methylthio-4-methyl-2-pentanone | 23550-40-5 |
| Neryl butyrate | 999-40-6 |
| Neryl formate | 2142-94-1 |
| Neryl isovalerate | 3915-83-1 |
| Octahydrocoumarin | 4430-31-3 |
| Phenethyl 2-furoate | 7149-32-8 |
| 1-Phenyl-2-pentanol | 705-73-7 |
| Phenylacetaldehyde diisobutylacetal | 68345-22-2 |
| Phenylacetaldehyde glyceryl acetal | 29895-73-6 |
| 2-(3-Phenylpropyl)pyridine | 2110-18-1 |
| Propyl phenylacetate | 4606-15-9 |

TABLE 9-continued

| Name | CAS # |
| --- | --- |
| Pyrazineethanethiol | 35250-53-4 |
| Ethyl 2-methyl pentanoate | 39255-32-8 |
| Methyl 2,4-decadienoate | 4493-42-9 |
| alpha-isomethyl ionone | 127-51-5 |
| 5-Methyl hexanoic acid | 628-46-6 |
| Ethyl 3-methyl pentanoate | 5870-68-8 |
| Ethyl 2-methyl-3,4-pentadienoate | 60523-21-9 |
| 3-Nonen-2-one | 14309-57-0 |
| 5-Methyl-3-hexen-2-one | 5166-53-0 |
| Maltol propionate | 68555-63-5 |
| 2-Methyl-3-(2-furyl) acrolein | 874-66-8 |
| Ethyl 3(2-furyl)propanoate | 10031-90-0 |
| 2-Phenyl-3-(2-furyl)-propenal | 57568-60-2 |
| 4-Methyl-2-pentyl-1,3-dioxolane | 1599-49-1 |
| 2-Ethyl-4,5-dimethyl oxazole | 53833-30-0 |
| Isobornyl isovalerate | 7779-73-9 |
| Theophylline-7-acetic acid | 652-37-9 |
| Ethyl trans-2-octenoate | 7367-82-0 |
| DL-Arginine | 7200-25-1 |
| Allyl Crotonate | 20474-93-5 |
| 2-Methoxystyrene | 612-15-7 |
| Magnesium Fumarate | 7704-71-4 |
| 2-Propionylpyrrole | 1073-26-3 |
| 2-methyl-1,3-dithiolane | 5616-51-3 |
| 2-ethyl-5-methyl pyrazine | 13360-64-0 |
| 2-methyl-3-(dimercaptomethyl)-furan | 65505-17-1 |
| Magnesium gluconate | 3632-91-5 |
| Manganese gluconate | 6485-39-8 |
| Erythritol | 149-32-6 |
| D-Arabinose | 28697-53-2 |
| D-Galactose | 59-23-4 |
| D-(+)-Mannose | 3458-28-4 |
| Sorbitol | 50-70-4 |
| Aspartame | 22839-47-0 |
| Cyclamic Acid | 100-88-9 |
| Dulcin | 150-69-6 |
| Glucose-1-phosphate Dipotassium Salt | 29732-59-0 |
| L-(+)-Arabinose | 87-72-9 |
| Fructose-6-Phosphate | 643-13-0 |
| D-Maltose Monohydrate | 6363-53-7 |
| Ribose | 24259-59-4 |
| Fructose 1,6-Diphosphate Disodium Salt | 26177-85-5 |
| Saccharin sodium, dihydrate | 6155-57-3 |
| 1,2-Benzisothiazol-3(2H)-one 1,1-dioxide, calcium salt | 6485-34-3 |
| 1,2-Benzisothiazolin-3-one 1,1-dioxide, potassium salt | 10332-51-1 |
| zeranol | 26538-44-3 |
| beta-D-fructopyranose | 7660-25-5 |
| D-fructose 1,6-bisphosphate | 488-69-7 |
| Ribose 5-phosphate | 4300-28-1 |
| Arabinose | 147-81-9 |
| Saccharin, sodium salt hydrate | 82385-42-0 |
| Maltitol | 585-88-6 |
| D-Fructose 1-phosphate | 15978-08-2 |
| D-Sorbitol 6-phosphate | 108392-12 |
| alpha-D-Xylose | 31178-70-8 |
| Inositol 1-phosphate | 573-35-3 |

TABLE 10

| Name | CAS # |
| --- | --- |
| Sodium Metabisulfite | 7681-57-4 |
| sodium hydrogen phosphate | 7558-79-4 |
| Sodium Phosphate Monobasic | 7558-80-7 |
| Sodium thiosulfate | 7772-98-71 |
| Orthoboric acid | 10043-35-3 |
| Diethanolamine | 111-42-2 |
| Benzaldehyde | 100-52-7 |
| Sorbic acid | 110-44-1 |
| L-(+)-Tartaric Acid | 87-69-4 |
| D-mannitol | 69-65-8 |
| Butyl paraben | 94-26-8 |
| Thymol | 89-83-8 |

TABLE 10-continued

| Name | CAS # |
| --- | --- |
| Methyl salicylate | 119-36-8 |
| Citric acid | 77-92-9 |
| Creatinine | 60-27-5 |
| Vitamin C | 50-81-7 |
| Benzoic Acid | 65-85-0 |
| Methyl 4-hydroxybenzoate | 99-76-3 |
| m-Cresol | 108-39-4 |
| p-Cresol | 106-44-5 |
| Aspirin | 50-78-2 |
| Phenol | 108-95-2 |
| Sucrose | 57-50-1 |
| Potassium citrate, monohydrate | 1534146 |
| Sodium acetate | 127-09-3 |
| Lactic acid | 50-21-5 |
| Propionic acid, sodium salt | 65-85 |
| Benzyl alcohol | 100-51-6 |
| Phenethyl alcohol | 60-12-8 |
| Cholesterol | 57-88-5 |
| D-Glucose | 50-99-7 |
| Sorbitol | 50-70-4 |
| Aspartame | 22839-47-0 |
| Saccharin | 81-07-2 |
| 2,6-Di-tert-Butyl-p-Cresol | 128-37-0 |
| 4-Chloro-3-methylphenol | 59-50-7 |
| glycerin | 56-81-5 |
| Propyl paraben | 94-13-3 |
| fumaric acid | 110-17-8 |
| dabco | 280-57-9 |
| p-Phenylenediamine | 106-50-3 |
| Anethole | 4180-23-8 |
| propyl gallate | 121-79-9 |
| L-monosodium glutamate | 142-47-2 |
| Butylated hydroxyanisole | 25013-16-5 |
| Cyclohexanol, 5-methyl-2-(1-methylethyl)-, (1alpha,2beta,5alpha)- | 89-78-1 |
| alpha-Thioglycerol | 96-27-5 |
| Sodium dehydroacetate | 4418-26-2 |
| Ethyl 4-hydroxybenzoate | 120-47-8 |
| Ethyl Vanillin | 121-32-4 |
| Triacetin | 102-76-1 |
| Potassium sorbate | 590-00-1 |
| Triethyl citrate | 77-93-0 |
| (S)-(+)-Arginine | 74-79-3 |
| Glycine | 56-40-6 |
| (S)-(−)-Histidine | 71-00-1 |
| (S)-(+)-Lysine | 56-87-1 |
| Quinone | 106-51-4 |
| Naphthalene, 2-ethoxy- | 93-18-5 |
| Methanesulfonic Acid | 75-75-2 |
| DL-Tartaric Acid | 133-37-9 |
| Cyclarnic acid | 100-88-9 |
| (S)-(−)-Phenylalanine | 63-91-2 |
| (S)-(−)-Tyrosine | 60-18-4 |
| Carvone | 99-49-0 |
| Ethyl butyrate | 105-54-4 |
| 6-Methyl-5-hepten-2-one | 110-93-0 |
| Ethyl acetoacetate | 141-97-9 |
| Methyl benzoate | 93-58-3 |
| Phenylacetic Acid | 103-82-2 |
| Adipic acid | 124-04-9 |
| Ethyl benzoate | 93-89-0 |
| Benzyl benzoate | 120-51-4 |
| Pyruvic acid | 127-17-3 |
| Succinic acid | 110-15-6 |
| Indole | 120-72-9 |
| Methyl anthranilate | 134-20-3 |
| Diethyl malonate | 105-53-3 |
| Niacin | 59-67-6 |
| Meso-inositol | 87-89-8 |
| 4-Aminobenzoic acid | 150-13-0 |
| Anisole | 100-66-3 |
| Urea | 57-13-6 |
| Pyrrolidine | 123-75-1 |
| Cyclopentanone | 120-92-3 |
| Acetic anhydride | 108-24-7 |
| Benzophenone | 119-61-9 |
| D-(−)-Fructose | 57-48-7 |
| D-(+)-Xylose | 58-86-6 |

TABLE 10-continued

| Name | CAS # |
|---|---|
| o-Methoxybenzoic Acid | 579-75-9 |
| linalool | 78-70-6 |
| ethyl isovalerate | 108-64-5 |
| 1,1'-Azobisformamide | 123-77-3 |
| 6-Methylcoumarin | 92-48-8 |
| acetoin | 513-86-0 |
| alpha-Phellandrene | 99-83-2 |
| Cymene | 99-87-6 |
| Dimethyl Succinate | 106-65-0 |
| p-Anisaldehyde | 123-11-5 |
| Phenyl ether | 101-84-8 |
| Tetrahydro-2-furanmethanol | 97-99-4 |
| Valerie Acid | 109-52-4 |
| 3,4-xylenol | 95-65-8 |
| 1,1-diethoxyethane | 105-57-7 |
| ethyl butyraldehyde | 97-96-1 |
| Ethyl crotonate | 623-70-1 |
| ethyl isobutyrate | 97-62-1 |
| methyl isovalerate | 556-24-1 |
| methyl propionate | 554-12-1 |
| methyl valeraldehyde | 123-15-9 |
| 4-(2,6,6-Trimethyl-2 cyclohexen-1-yl)-3-buten-2-one | 127-41-3 |
| 4-(2,6,6-trimethyl-1 cyclohexen-1-yl)-3-buten-2-one | 14901-07-6 |
| Maleic acid | 110-16-7 |
| 3-Methylbutanoic acid | 503-74-2 |
| L-Glutamic Acid | 56-86-0 |
| D-limonene | 5989-27-5 |
| 1-Phenyl-1-propanol | 93-54-9 |
| 2'-Hydroxyacetophenone | 118-93-4 |
| 2,4-Dihydroxybenzoic Acid | 89-86-1 |
| 2-Phenyl-1-propanol | 1123-85-9 |
| 3-Phenylpropionic Acid | 501-52-0 |
| 4-Ethoxyphenol | 622-62-8 |
| Alpha-Terpineol | 98-55-5 |
| Benzaldehyde Dimethylacetal | 1125-88-8 |
| Benzyl Ether | 103-50-4 |
| Benzyl Formate | 104-57-4 |
| Benzyl Salicylate | 118-58-1 |
| Cinnamyl Alcohol | 104-54-1 |
| D-(+)-Glucono-1,5-lactone | 4253-68-3 |
| D-Isoascorbic Acid | 89-65-6 |
| 2,3-Naphthalenediol | 92-44-4 |
| Diethyl Succinate | 123-25-1 |
| Ethyl 2-Aminobenzoate | 87-25-2 |
| Ethyl Cinnamate | 103-36-6 |
| Ethyl Phenylacetate | 101-97-3 |
| Ethyl Salicylate | 118-61-6 |
| gamma-Valerolactone | 108-29-2 |
| Hydroquinone Dimethyl Ether | 150-78-7 |
| Isocaproic Acid | 646-07-1 |
| Isoeugenol | 97-54-1 |
| Isopropyl Benzoate | 939-48-0 |
| L-(+)-Isoleucine | 73-32-5 |
| L-Malic acid | 97-67-6 |
| L-2-Aminopropionic Acid | 56-41-7 |
| L-Carnitine | 541-15-1 |
| L-Glutamine | 56-85-9 |
| L-Hydroxyproline | 51-35-4 |
| L-Proline | 147-85-3 |
| L-Serine | 56-45-1 |
| L-Threonine | 72-19-5 |
| L-Valine | 72-18-4 |
| Phenoxyacetic Acid | 122-59-8 |
| Veratrole | 91-16-7 |
| 2-Ethylbutyric acid | 88-09-5 |
| 2-Methylpyrazine | 109-08-0 |
| o-methoxybenzaldehyde | 135-02-4 |
| L-Leucine | 61-90-5 |
| L-Asparagine | 70-47-3 |
| propiophenone | 93-55-0 |
| 5-isopropyl-2-methyl-phenol | 499-75-2 |
| Xylitol | 87-99-0 |
| ethyl 4-oxopentanoate | 539-88-8 |
| methyl cinnamate | 103-26-4 |
| cumic alcohol | 536-60-7 |
| methyl 2-naphthyl ketone | 93-08-3 |
| 1-methyl-4-(1-methylethyl)1,4-Cyclohexadiene | 99-85-4 |
| en-ethylene diamine | |
| Caffeine | 58-08-2 |
| 5-methylfurfural | 620-02-0 |
| furfuryl acetate | 623-17-6 |
| terpinen-4-ol | 10482-56-1 |
| phenylethanal | 122-78-1 |
| 4'-Methoxyacetophenone | 100-06-1 |
| D-Fenchone | 4695-62-9 |
| 1-Methoxy-4-methylbenzene | 104-93-8 |
| o-methylanisole | 578-58-5 |
| Acetylacetaldehyde dimethyl acetal | 5436-21-5 |
| p-methylacetophenone | 122-00-9 |
| Methyl phenylacetate | 101-41-7 |
| 4-Ethoxybenzaldehyde | 10031-82-0 |
| p-tolyl acetate | 140-39-6 |
| 2,6-Dimethoxyphenol | 91-10-1 |
| Methyl 2-methoxybenzoate | 606-45-1 |
| alpha-methylcinnamaldehyde | 101-39-3 |
| 2-methoxycinnamaldehyde | 60125-24-8 |
| Potassium bicarbonate | 298-14-6 |
| piperonyl acetate | 326-61-4 |
| 2,3-hexanedione | 3848-24-6 |
| furfural acetone | 623-15-4 |
| trans beta-(2-furyl)acrolein | 623-30-3 |
| carveol | 99-48-9 |
| Methyl nicotinate | 93-60-7 |
| Ethyl benzoylacetate | 94-02-0 |
| Methyl 4-methoxybenzoate | 121-98-2 |
| Levulinic acid | 123-76-2 |
| m-Dimethoxybenzene | 151-10-0 |
| 2-acetylpyridine | 1122-62-9 |
| tetramethyl-pyrazine | 1124-11-4 |
| 2,3-dimethyl-pyrazine | 5910-89-4 |
| trimethyl-pyrazine | 14667-55-1 |
| 2-ethyl-3-methyl-pyrazine | 15707-23-0 |
| 5-Methyl-3H-furan-2-one | 591-12-8 |
| 2-Methoxy-4-methylphenol | 93-51-6 |
| piperazine | 110-85-0 |
| 2-Methoxy-4-propylphenol | 2785-87-7 |
| Naphthalene, 2-(2 methylpropoxy)- | 2173-57-1 |
| 2-Acetyl-1-methylpyrrole | 932-16-1 |
| 3,3-Dimethylacrylic acid | 541-47-9 |
| Ethyl sorbate | 2396-84-1 |
| 4-(4-Hydroxyphenyl)-2-butanone | 5471-51-2 |
| 4-Methoxyphenylacetone | 122-84-9 |
| (−)-Myrtenal | 564-94-3 |
| 3-Phenylpropionaldehyde | 104-53-0 |
| 1-Phenylethyl propionate | 120-45-6 |
| 2-Methyltetrahydrofuran-3-one | 3188-00-9 |
| Cinnamyl acetate | 103-54-8 |
| Styrallyl acetate | 93-92-5 |
| Ethyl 4-methoxybenzoate | 94-30-4 |
| Benzyl propionate | 122-63-4 |
| Phenylpyruvate | 156-06-9 |
| furaneol | 3658-77-3 |
| methyl 2-methylbutanoate | 868-57-5 |
| Benzeneacetaldehyde, alpha methyl- | 93-53-8 |
| Dimethyl anthranilate | 85-91-6 |
| 1,1-Dimethoxy-2-phenylpropane | 90-87-9 |
| 4-hexanolide | 695-06-7 |
| Dimethylbenzylcarbinyl acetate | 151-05-3 |
| Benzyl isobutyrate | 103-28-6 |
| Acetyl isoeugenol | 93-29-8 |
| 2-Acetyl-5-methyl furan | 1193-79-9 |
| Alpha-methyl-p isopropylphenylpropanaldehyde | 103-95-7 |
| Benzylcarbinyl formate | 104-62-1 |
| p-Cresyl alpha-toluate | 101-94-0 |
| Potassium bisulfate | 7646-93-7 |
| Potassium carbonate | 584-08-7 |
| Potassium chloride | 7447-40-7 |
| Potassium hydroxide | 1310-58-3 |
| Ethyl tiglate | 5837-78-5 |
| Nerol oxide | 1786-08-9 |
| DL-Tetrahydrofurfuryl propionate | 637-65-0 |
| Benzaldehyde propylene glycol acetal | 2568-25-4 |
| 2-Methyl-3-(2-furyl) acrolein | 874-66-8 |
| vanillin | 121-33-5 |
| Cholic acid | 81-25-4 |
| R-Carvone | 6485-40-1 |

TABLE 10-continued

| Name | CAS # |
|---|---|
| Potassium nitrate | 7757-79-1 |
| Potassium permanganate | 7722-64-7 |
| Potassium persulfate | 7727-21-1 |
| Potassium phosphate, dibasic | 2139900 |
| Potassium Phosphate Monobasic | 7778-77-0 |
| Potassium sulfate | 7778-80-5 |
| Sodium bicarbonate | 144-55-8 |
| Sodium bisulfite | 7631-90-5 |
| Sodium carbonate | 497-19-8 |
| Sodium chloride | 7647-14-5 |
| Sodium dithionite | 7775-14-6 |
| Sodium hydroxide | 1310-73-2 |
| Sodium nitrite | 7632-00-0 |
| Sodium Pyrophosphate | 7722-88-5 |
| Sodium sulfate | 7757-82-6 |
| Sodium sulfite | 7757-83-7 |
| Sodium thiocyanate | 540-72-7 |
| Calcium Carbonate | 471-34-1 |
| Calcium chloride | 10043-52-4 |
| Calcium gluconate | 299-28-5 |
| Calcium hydroxide | 1305-62-0 |
| Calcium phosphate, dibasic | 7757-93-9 |
| Calcium sulfate | 7778-18-9 |
| N-Methyl-D-glucamine | 6284-40-8 |
| Calcium oxide | 1305-78-8 |
| Calcium Phosphate Monobasic | 7758-23-8 |
| Magnesium chloride hexahydrate | 7791-18-6 |
| Magnesium sulfate | 7487-88-9 |
| Magnesium Sulfate Heptahydrate | 10034-99-8 |
| Aluminum chloride hexahydrate | 7784-13-6 |
| aluminum nitrate nonahydrate | 7784-27-2 |
| Aluminum potassium sulfate, dodecahydrate | 7784-24-9 |
| Aluminum sulfate, octadecahydrate | 7784-31-8 |
| (S)-(–)-Cysteine | 52-90-4 |
| p-Toluenesulfonic Acid | 104-15-4 |
| Potassium bitartrate | 868-14-4 |
| DL-aspartic acid | 617-45-8 |
| p-Dimethylaminobenzaldehyde | 100-10-7 |
| Sodium salicylate | 54-21-7 |
| Benzoin | 119-53-9 |
| Sodium dodecyl sulfate | 151-21-3 |
| L-Menthol | 2216-51-5 |
| Tiron | 149-45-1 |
| Riboflavin | 83-88-5 |
| Sodium Acetate Trihydrate | 6131-90-4 |
| Disodium Succinate Hexahydrate | 6106-21-4 |
| Disodium ethylenediaminetetraacetate dihydrate | 6381-92-6 |
| sodium citrate, dihydrate | 1545801 |
| Sodium potassium tartrate, tetrahydrate | 6381-59-5 |
| L-(f)-Arginine monohydrochloride | 1119-34-2 |
| Ethylenediamine dihydrochloride | 333-18-6 |
| Sodium formate | 141-53-7 |
| Sodium acetate | 127-09-3 |
| Potassium acetate | 127-08-2 |
| Ammonium citrate | 3012-65-5 |
| Ammonium bicarbonate | 1066-33-7 |
| Ammonium chloride | 12125-02-9 |
| Ammonium nitrate | 6484-52-2 |
| Ammonium persulfate | 7727-54-0 |
| Ammonium sulfate | 7783-20-2 |
| Zinc chloride | 7646-85-7 |
| Sulfuric acid, zinc salt(1:1), heptahydrate | 7446-20-0 |
| Sodium Tripolyphosphate | 7758-29-4 |
| ammonium benzoate | 1863-63-4 |
| ammonium bisulfite | 10192-30-0 |
| 1,5-Naphthalenedisulfonic Acid Disodium Salt | 1655-29-4 |
| 4-Hydroxybenzoic Acid | 99-96-7 |
| Diphenylacetic Acid | 117-34-0 |
| Glutaric Acid | 110-94-1 |
| L-(–)-Fucose | 2438-80-4 |
| L-Cysteine Hydrochloride | 52-89-1 |
| L-Histidine Hydrochloride Monohydrate | 1880304 |
| o-Toluic Acid | 118-90-1 |
| Pivalic Acid | 75-98-9 |
| Pyruvic Acid Sodium Salt | 113-24-6 |
| Potassium bromide | 2139626 |
| Sodium Dithionate Dihydrate | 7631-94-9 |
| Sodium Malonate | 141-95-7 |
| Trisodium Citrate | 68-04-2 |
| Potassium Sodium Tartrate | 304-59-6 |
| Potassium Citrate | 866-84-2 |
| D-Maltose Monohydrate | 6363-53-7 |
| Cyclohexaamylose | 10016-20-3 |
| Dodecyl sulfate, lithium salt | 2044-56-6 |
| Manganese chloride | 2145076 |
| methyl-urea | 598-50-5 |
| beta-Cyclodextrin | 7585-39-9 |
| Triphosphoric acid, pentapotassium salt | 13845-36-8 |
| Glycine ethyl ester hydrochloride | 623-33-6 |
| L-Histidine methyl ester dihydrochloride | 7389-87-9 |
| L-Leucine methyl ester hydrochloride | 7517-19-3 |
| D-Lysine hydrochloride | 7274-88-6 |
| 2-Naphthalenesulfonic acid sodium salt | 532-02-5 |
| calcium nitrate tetrahydrate | 13477-34-4 |
| Vitamin B1 | 59-43-8 |
| Zinc Acetate Dihydrate | 5970-45-6 |
| Potassium fluoride | 7789-23-3 |
| Potassium iodate | 2139718 |
| Potassium iodide | 7681-11-0 |
| Potassium thiocyanate | 333-20-0 |
| Sodium bromide | 7647-15-6 |
| Sodium fluoride | 7681-49-4 |
| Sodium iodide | 7681-82-5 |
| Sodium nitrate | 7631-99-4 |
| Calcium acetate | 5743-26-0 |
| Trichloroacetic acid | 76-03-9 |
| Ammonium acetate | 631-61-8 |
| Ammonium fluoride | 12125-01-8 |
| DL-malic acid | 617-48-1 |
| t-Butyl Alcohol | 75-65-0 |
| beta-Alanine | 107-95-9 |
| (S)-(–)-Tryptophan | 73-22-3 |
| Malonic acid | 141-82-2 |
| Phenethylamine | 64-04-0 |
| Salicylylaldehyde | 90-02-8 |
| Sodium benzoate | 532-32-1 |
| Mandelic acid | 90-64-2 |
| Calcium pantothenate | 137-08-6 |
| Chloroacetic Acid | 79-11-8 |
| Ethanol Amine | 141-43-5 |
| Salicylic acid | 69-72-7 |
| Saccharin sodium | 128-44-9 |
| Thiamine hydrochloride | 67-03-8 |
| 2,2'-Oxybisethanol | 111-46-6 |
| Resorcinol | 108-46-3 |
| 2-Amino-2-(hydroxymethyl)-1,3 propanediol | 77-86-1 |
| 2,5-Dimethylphenol | 95-87-4 |
| Ammonium Phosphate Monobasic | 7722-76-1 |
| 1,3-Butanediol | 107-88-0 |
| Glycolic Acid | 79-14-1 |
| Sodium Gluconate | 527-07-1 |
| Terephthalic Acid | 100-21-0 |
| L-Ascorbic Acid Sodium Salt | 134-03-2 |
| 3-Acetyl-6-methyl-2,4 pyrandione | 520-45-6 |
| Calcium Acetate | 62-54-4 |
| Nicotinamide | 98-92-0 |
| 1-Hydroxy-2-naphthoic Acid | 86-48-6 |
| 2-Isopropylphenol | 88-69-7 |
| 4-Aminosalicylic Acid | 65-49-6 |
| Calcium Glycerophosphate | 27214-00-2 |
| Erythorbic Acid Sodium Salt | 7378-23-6 |
| Gluconic Acid Potassium Salt | 299-27-4 |
| Orotic Acid | 65-86-1 |
| p-Anise Alcohol | 105-13-5 |
| Potassium Benzoate | 582-25-2 |
| Taurine | 107-35-7 |
| Thiamine Nitrate | 532-43-4 |
| 3,3,5-Trimethyl-1-cyclohexanol | 116-02-9 |
| tert-Butylhydroquinone | 1948-33-0 |
| Sulfosalicylic acid | 97-05-2 |
| Gallic acid | 149-91-7 |
| L-borneol | 464-45-9 |
| Isoborneol | 124-76-5 |
| 2,5-Dihydroxybenzoic acid, Gentisic acid | 490-79-9 |
| 5-hydroxy-6-methyl-1,3,4-pyridinedimethanol | 65-23-6 |
| Naphthalene-2-sulfonic acid | 120-18-3 |

TABLE 10-continued

| Name | CAS # |
|---|---|
| Ethanesulfonic acid, 2 hydroxy-, monosodium salt | 1562-00-1 |
| Pamoic acid | 130-85-8 |
| 2,4-Dimethylphenol | 105-67-9 |
| 3,5-Dihydroxyacetophenone | 51863-60-6 |
| Eugenol | 97-53-0 |
| n-Butyric Acid | 107-92-6 |
| Hydroquinone | 123-31-9 |
| Sodium acetate | 127-09-3 |
| Lactic acid | 50-21-5 |
| Propionic acid, sodium salt | 65-85 |
| Benzyl alcohol | 100-51-6 |
| Phenethyl alcohol | 60-12-8 |
| Cholesterol | 57-88-5 |
| D-Glucose | 50-99-7 |
| Sorbitol | 50-70-4 |
| Aspartame | 22839-47-0 |
| Saccharin | 81-07-2 |
| 2,6-Di-tert-Butyl-p-Cresol | 128-37-0 |
| 4-Chloro-3-methylphenol | 59-50-7 |
| glycerin | 56-81-5 |
| Propyl paraben | 94-13-3 |
| fumaric acid | 110-17-8 |
| dabco | 280-57-9 |
| p-Phenylenediamine | 106-50-3 |
| Anethole | 4180-23-8 |
| propyl gallate | 121-79-9 |
| L-monosodium glutamate | 142-47-2 |
| Butylated hydroxyanisole | 25013-16-5 |
| Cyclohexanol, 5-methyl-2-(1 methylethyl)-, (1alpha,2beta,5alpha)- | 89-78-1 |
| alpha-Thioglycerol | 96-27-5 |
| Sodium dehydroacetate | 4418-26-2 |
| Ethyl 4-hydroxybenzoate | 120-47-8 |
| Ethyl Vanillin | 121-32-4 |
| Triacetin | 102-76-1 |
| Potassium sorbate | 590-00-1 |
| Triethyl citrate | 77-93-0 |
| (S)-(+)-Arginine | 74-79-3 |
| Glycine | 56-40-6 |
| (S)-(−)-Histidine | 71-00-1 |
| (S)-(+)-Lysine | 56-87-1 |
| Quinone | 106-51-4 |
| Naphthalene, 2-ethoxy- | 93-18-5 |
| Methanesulfonic Acid | 75-75-2 |
| DL-Tartaric Acid | 133-37-9 |
| Cyclamic acid | 100-88-9 |
| (S)-(−)-Phenylalanine | 63-91-2 |
| (S)-(−)-Tyrosine | 60-18-4 |
| Carvone | 99-49-0 |
| Ethyl butyrate | 105-54-4 |
| 6-Methyl-5-hepten-2-one | 110-93-0 |
| Ethyl acetoacetate | 141-97-9 |
| Methyl benzoate | 93-58-3 |
| Phenylacetic Acid | 103-82-2 |
| Adipic acid | 124-04-9 |
| Ethyl benzoate | 93-89-0 |
| Benzyl benzoate | 120-51-4 |
| Pyruvic acid | 127-17-3 |
| Succinic acid | 110-15-6 |
| Indole | 120-72-9 |
| Methyl anthranilate | 134-20-3 |
| Diethyl malonate | 105-53-3 |
| Niacin | 59-67-6 |
| Meso-inositol | 87-89-8 |
| 4-Aminobenzoic acid | 150-13-0 |
| Anisole | 100-66-3 |
| Urea | 57-13-6 |
| Pyrrolidine | 123-75-1 |
| Cyclopentanone | 120-92-3 |
| Acetic anhydride | 108-24-7 |
| Benzophenone | 119-61-9 |
| D-(−)-Fructose | 57-48-7 |
| D-(+)-Xylose | 58-86-6 |
| o-Methoxybenzoic Acid | 579-75-9 |
| linalool | 78-70-6 |
| ethyl isovalerate | 108-64-5 |
| 1,1′-Azobisformamide | 123-77-3 |
| 6-Methylcournarin | 92-48-8 |

TABLE 10-continued

| Name | CAS # |
|---|---|
| acetoin | 513-86-0 |
| alpha-Phellandrene | 99-83-2 |
| Cymene | 99-87-6 |
| Dimethyl Succinate | 106-65-0 |
| p-Anisaldehyde | 123-11-5 |
| Phenyl ether | 101-84-8 |
| Tetrahydro-2-furanmethanol | 97-99-4 |
| Valeric Acid | 109-52-4 |
| 3,4-xylenol | 95-65-8 |
| 1,1-diethoxyethane | 105-57-7 |
| ethyl butyraldehyde | 97-96-1 |
| Ethyl crotonate | 623-70-1 |
| ethyl isobutyrate | 97-62-1 |
| methyl isovalerate | 556-24-1 |
| methyl propionate | 554-12-1 |
| methyl valeraldehyde | 123-15-9 |
| 4-(2,6,6-Trimethyl-2 cyclohexen-1-yl)-3-buten-2-one | 127-41-3 |
| 4-(2,6,6-trimethyl-1 cyclohexen-1-yl)-3-buten-2-one | 14901-07-6 |
| Maleic acid | 110-16-7 |
| 3-Methylbutanoic acid | 503-74-2 |
| L-Glutamic Acid | 56-86-0 |
| D-limonene | 5989-27-5 |
| 1-Pheny1-1-propanol | 93-54-9 |
| 2′-Hydroxyacetophenone | 118-93-4 |
| 2,4-Dihydroxybenzoic Acid | 89-86-1 |
| 2-Pheny1-1-propanol | 1123-85-9 |
| 3-Phenylpropionic Acid | 501-52-0 |
| 4-Ethoxyphenol | 622-62-8 |
| Alpha-Terpineol | 98-55-5 |
| Benzaldehyde Dimethylacetal | 1125-88-8 |
| Benzyl Ether | 103-50-4 |
| Benzyl Formate | 104-57-4 |
| Benzyl Salicylate | 118-58-1 |
| Cinnamyl Alcohol | 104-54-1 |
| D-(+)-Glucono-1,5-lactone | 4253-68-3 |
| D-Isoascorbic Acid | 89-65-6 |
| 2,3-Naphthalenediol | 92-44-4 |
| Diethyl Succinate | 123-25-1 |
| Ethyl 2-Aminobenzoate | 87-25-2 |
| Ethyl Cinnamate | 103-36-6 |
| Ethyl Phenylacetate | 101-97-3 |
| Ethyl Salicylate | 118-61-6 |
| gamma-Valerolactone | 108-29-2 |
| Hydroquinone Dimethyl Ether | 150-78-7 |
| Isocaproic Acid | 646-07-1 |
| Isoeugenol | 97-54-1 |
| Isopropyl Benzoate | 939-48-0 |
| L-(+)-Isoleucine | 73-32-5 |
| L-Malic acid | 97-67-6 |
| L-2-Aminopropionic Acid | 56-41-7 |
| L-Carnitine | 541-15-1 |
| L-Glutamine | 56-85-9 |
| L-Hydroxyproline | 51-35-4 |
| L-Proline | 147-85-3 |
| L-Serine | 56-45-1 |
| L-Threonine | 72-19-5 |
| L-Valine | 72-18-4 |
| Phenoxyacetic Acid | 122-59-8 |
| Veratrole | 91-16-7 |
| 2-Ethylbutyric acid | 88-09-5 |
| 2-Methylpyrazine | 109-08-0 |
| o-methoxybenzaldehyde | 135-02-4 |
| L-Leucine | 61-90-5 |
| L-Asparagine | 70-47-3 |
| propiophenone | 93-55-0 |
| 5-isopropyl-2-methyl-phenol | 499-75-2 |
| Xylitol | 87-99-0 |
| ethyl 4-oxopentanoate | 539-88-8 |
| methyl cinnamate | 103-26-4 |
| cumic alcohol | 536-60-7 |
| methyl 2-naphthyl ketone | 93-08-3 |
| 1-methyl-4-(1-methylethyl)-1,4-Cyclohexadiene | 99-85-4 |
| en-ethylene diamine | |
| Caffeine | 58-08-2 |
| 5-methylfurfural | 620-02-0 |
| furfuryl acetate | 623-17-6 |
| terpinen-4-ol | 10482-56-1 |
| phenylethanal | 122-78-1 |

TABLE 10-continued

| Name | CAS # |
|---|---|
| 4'-Methoxyacetophenone | 100-06-1 |
| D-Fenchone | 4695-62-9 |
| 1-Methoxy-4-methylbenzene | 104-93-8 |
| o-methylanisole | 578-58-5 |
| Acetylacetaldehyde dimethyl acetal | 5436-21-5 |
| p-methylacetophenone | 122-00-9 |
| Methyl phenylacetate | 101-41-7 |
| 4-Ethoxybenzaldehyde | 10031-82-0 |
| p-tolyl acetate | 140-39-6 |
| 2,6-Dmethoxyphenol | 91-10-1 |
| Methyl 2-methoxybenzoate | 606-45-1 |
| alpha-methylcinnamaldehyde | 101-39-3 |
| 2-methoxycinnamaldehyde | 60125-24-8 |
| Potassium bicarbonate | 298-14-6 |
| piperonyl acetate | 326-61-4 |
| 2,3-hexanedione | 3848-24-6 |
| furfural acetone | 623-15-4 |
| trans beta-(2-fury)acrolein | 623-30-3 |
| carveol | 99-48-9 |
| Methyl nicotinate | 93-60-7 |
| Ethyl benzoylacetate | 94-02-0 |
| Methyl 4-methoxybenzoate | 121-98-2 |
| Levulinic acid | 123-76-2 |
| m-Dimethoxybenzene | 151-10-0 |
| 2-acetylpyridine | 1122-62-9 |
| tetramethyl-pyrazine | 1124-11-4 |
| 2,3-dimethyl-pyrazine | 5910-89-4 |
| trimethyl-pyrazine | 14667-55-1 |
| 2-ethyl-3-methyl-pyrazine | 15707-23-0 |
| 5-Methyl-3H-furan-2-one | 591-12-8 |
| 2-Methoxy-4-methylphenol | 93-51-6 |
| piperazine | 110-85-0 |
| 2-Methoxy-4-propylphenol | 2785-87-7 |
| Naphthalene, 2-(2-methylpropoxy)- | 2173-57-1 |
| 2-Acetyl-1-methylpyrrole | 932-16-1 |
| 3,3-Dimethylacrylic acid | 541-47-9 |
| Ethyl sorbate | 2396-84-1 |
| 4-(4-Hydroxyphenyl)-2-butanone | 5471-51-2 |
| 4-Methoxyphenylacetone | 122-84-9 |
| (−)-Myrtenal | 564-94-3 |
| 3-Phenylpropionaldehyde | 104-53-0 |
| 1-Phenylethyl propionate | 120-45-6 |
| 2-Methyltetrahydrofuran-3-one | 3188-00-9 |
| Cinnamyl acetate | 103-54-8 |
| Styrallyl acetate | 93-92-5 |
| Ethyl 4-methoxybenzoate | 94-30-4 |
| Benzyl propionate | 122-63-4 |
| Phenylpyruvate | 156-06-9 |
| furaneol | 3658-77-3 |
| methyl 2-methylbutanoate | 868-57-5 |
| Benzeneacetaldehyde, alpha methyl- | 93-53-8 |
| Dimethyl anthranilate | 85-91-6 |
| 1,1-Dimethoxy-2-phenylpropane | 90-87-9 |
| 4-hexanolide | 695-06-7 |
| Dimethylbenzylcarbinyl acetate | 151-05-3 |
| Benzyl isobutyrate | 103-28-6 |
| Acetyl isoeugenol | 93-29-8 |
| 2-Acetyl-5-methyl furan | 1193-79-9 |
| Alpha-methyl-pisopropylphenylpropanaldehyde | 103-95-7 |
| Benzylcarbinyl formate | 104-62-1 |
| p-Cresyl alpha-toluate | 101-94-0 |
| Potassium bisulfate | 7646-93-7 |
| Potassium carbonate | 584-08-7 |
| Potassium chloride | 7447-40-7 |
| Potassium hydroxide | 1310-58-3 |
| Ethyl tiglate | 5837-78-5 |
| Nerol oxide | 1786-08-9 |
| DL-Tetrahydrofurfuryl propionate | 637-65-0 |
| Benzaldehyde propylene glycol acetal | 2568-25-4 |
| 2-Methyl-3-(2-furyl) acrolein | 874-66-8 |
| vanillin | 121-33-5 |
| Cholic acid | 81-25-4 |
| R-Carvone | 6485-40-1 |
| Potassium nitrate | 7757-79-1 |
| Potassium permanganate | 7722-64-7 |
| Potassium persulfate | 7727-21-1 |
| Potassium phosphate, dibasic | 2139900 |
| Potassium Phosphate Monobasic | 7778-77-0 |
| Potassium sulfate | 7778-80-5 |
| Sodium bicarbonate | 144-55-8 |
| Sodium bisulfite | 7631-90-5 |
| Sodium carbonate | 497-19-8 |
| Sodium chloride | 7647-14-5 |
| Sodium dithionite | 7775-14-6 |
| Sodium hydroxide | 1310-73-2 |
| Sodium nitrite | 7632-00-0 |
| Sodium Pyrophosphate | 7722-88-5 |
| Sodium sulfate | 7757-82-6 |
| Sodium sulfite | 7757-83-7 |
| Sodium thiocyanate | 540-72-7 |
| Calcium Carbonate | 471-34-1 |
| Calcium chloride | 10043-52-4 |
| Calcium gluconate | 299-28-5 |
| Calcium hydroxide | 1305-62-0 |
| Calcium phosphate, dibasic | 7757-93-9 |
| Calcium sulfate | 7778-18-9 |
| N-Methyl-D-glucamine | 6284-40-8 |
| Calcium oxide | 1305-78-8 |
| Calcium Phosphate Monobasic | 7758-23-8 |
| Magnesium chloride hexahydrate | 7791-18-6 |
| Magnesium sulfate | 7487-88-9 |
| Magnesium Sulfate Heptahydrate | 10034-99-8 |
| Aluminum chloride hexahydrate | 7784-13-6 |
| aluminum nitrate nonahydrate | 7784-27-2 |
| Aluminum potassium sulfate, dodecahydrate | 7784-24-9 |
| Aluminum sulfate, octadecahydrate | 7784-31-8 |
| (S)-(−)-Cysteine | 52-90-4 |
| p-Toluenesulfonic Acid | 104-15-4 |
| Potassium bitartrate | 868-14-4 |
| DL-aspartic acid | 617-45-8 |
| p-Dimethylaminobenzaldehyde | 100-10-7 |
| Sodium salicylate | 54-21-7 |
| Benzoin | 119-53-9 |
| Sodium dodecyl sulfate | 151-21-3 |
| L-Menthol | 2216-51-5 |
| Tiron | 149-45-1 |
| Riboflavin | 83-88-5 |
| Sodium Acetate Trihydrate | 6131-90-4 |
| Disodium Succinate Hexahydrate | 6106-21-4 |
| Disodium ethylenediaminetetraacetate dihydrate | 6381-92-6 |
| sodium citrate, dihydrate | 1545801 |
| Sodium potassium tartrate, tetrahydrate | 6381-59-5 |
| L-(+)-Arginine monohydrochloride | 1119-34-2 |
| Ethylenediamine dihydrochloride | 333-18-6 |
| Sodium formate | 141-53-7 |
| Sodium acetate | 127-09-3 |
| Potassium acetate | 127-08-2 |
| Ammonium citrate | 3012-65-5 |
| Ammonium bicarbonate | 1066-33-7 |
| Ammonium chloride | 12125-02-9 |
| Ammonium nitrate | 6484-52-2 |
| Ammonium persulfate | 7727-54-0 |
| Ammonium sulfate | 7783-20-2 |
| Zinc chloride | 7646-85-7 |
| Sulfuric acid, zinc salt (1:1), heptahydrate | 7446-20-0 |
| Sodium Tripolyphosphate | 7758-29-4 |
| ammonium benzoate | 1863-63-4 |
| ammonium bisulfite | 10192-30-0 |
| 1,5-Naphthalenedisulfonic Acid Disodium Salt | 1655-29-4 |
| 4-Hydroxybenzoic Acid | 99-96-7 |
| Diphenylacetic Acid | 117-34-0 |
| Glutaric Acid | 110-94-1 |
| L-(−)-Fucose | 2438-80-4 |
| L-Cysteine Hydrochloride | 52-89-1 |
| L-Histidine Hydrochloride Monohydrate | 1880304 |
| o-Toluic Acid | 118-90-1 |
| Pivalic Acid | 75-98-9 |
| Pyruvic Acid Sodium Salt | 113-24-6 |
| Potassium bromide | 2139626 |
| Sodium Dithionate Dihydrate | 7631-94-9 |
| Sodium Malonate | 141-95-7 |
| Trisodium Citrate | 68-04-2 |
| Potassium Sodium Tartrate | 304-59-6 |
| Potassium Citrate | 866-84-2 |
| D-Maltose Monohydrate | 6363-53-7 |
| Cyclohexaamylose | 10016-20-3 |

TABLE 10-continued

| Name | CAS # |
|---|---|
| Dodecyl sulfate, lithium salt | 2044-56-6 |
| Manganese chloride | 2145076 |
| methyl-urea | 598-50-5 |
| beta-Cyclodextrin | 7585-39-9 |
| Triphosphoric acid, pentapotassium salt | 13845-36-8 |
| Glycine ethyl ester hydrochloride | 623-33-6 |
| L-Histidine methyl ester dihydrochloride | 7389-87-9 |
| L-Leucine methyl ester hydrochloride | 7517-19-3 |
| D-Lysine hydrochloride | 7274-88-6 |
| 2-Naphthalenesulfonic acid sodium salt | 532-02-5 |
| calcium nitrate tetrahydrate | 13477-34-4 |
| Vitamin B1 | 59-43-8 |
| Zinc Acetate Dihydrate | 5970-45-6 |
| Potassium fluoride | 7789-23-3 |
| Potassium iodate | 2139718 |
| Potassium iodide | 7681-11-0 |
| Potassium thiocyanate | 333-20-0 |
| Sodium bromide | 7647-15-6 |
| Sodium fluoride | 7681-49-4 |
| Sodium iodide | 7681-82-5 |
| Sodium nitrate | 7631-99-4 |
| Calcium acetate | 5743-26-0 |
| Trichloroacetic acid | 76-03-9 |
| Ammonium acetate | 631-61-8 |
| Ammonium fluoride | 12125-01-8 |
| DL-malic acid | 617-48-1 |
| t-Butyl Alcohol | 75-65-0 |
| beta-Alanine | 107-95-9 |
| (S)-(−)-Tryptophan | 73-22-3 |
| Malonic acid | 141-82-2 |
| Phenethylamine | 64-04-0 |
| Salicylylaldehyde | 90-02-8 |
| Sodium benzoate | 532-32-1 |
| Mandelic acid | 90-64-2 |
| Calcium pantothenate | 137-08-6 |
| Chloroacetic Acid | 79-11-8 |
| Ethanol Amine | 141-43-5 |
| Salicylic acid | 69-72-7 |
| Saccharin sodium | 128-44-9 |
| Thiamine hydrochloride | 67-03-8 |
| 2,2'-Oxybisethanol | 111-46-6 |
| Resorcinol | 108-46-3 |
| 2-Amino-2-(hydroxymethyl)-1,3-propanediol | 77-86-1 |
| 2,5-Dimethylphenol | 95-87-4 |
| Ammonium Phosphate Monobasic | 7722-76-1 |
| 1,3-Butanediol | 107-88-0 |
| Glycolic Acid | 79-14-1 |
| Sodium Gluconate | 527-07-1 |
| Terephthalic Acid | 100-21-0 |
| L-Ascorbic Acid Sodium Salt | 134-03-2 |
| 3-Acetyl-6-methyl-2,4-pyrandione | 520-45-6 |
| Calcium Acetate | 62-54-4 |
| Nicotinamide | 98-92-0 |
| 1-Hydroxy-2-naphthoic Acid | 86-48-6 |
| 2-isopropylphenol | 88-69-7 |
| 4-Aminosalicylic Acid | 65-49-6 |
| Calcium Glycerophosphate | 27214-00-2 |
| Erythorbic Acid Sodium Salt | 7378-23-6 |
| Gluconic Acid Potassium Salt | 299-27-4 |
| Orotic Acid | 65-86-1 |
| p-Anise Alcohol | 105-13-5 |
| Potassium Benzoate | 582-25-2 |
| Taurine | 107-35-7 |
| Thiamine Nitrate | 532-43-4 |
| 3,3,5-Trimethyl-1-cyclohexanol | 116-02-9 |
| tert-Butylhydroquinone | 1948-33-0 |
| Sulfosalicylic acid | 97-05-2 |
| Gallic acid | 149-91-7 |
| L-borneol | 464-45-9 |
| Isoborneol | 124-76-5 |
| 2,5-Dihydroxybenzoic acid, Gentisic acid | 490-79-9 |
| 5-hydroxy-6-methyl-3,4-pyridinedimethanol | 65-23-6 |
| Naphthalene-2-sulfonic acid | 120-18-3 |
| Ethanesulfonic acid, 2-hydroxy-, monosodium salt | 1562-00-1 |
| Pamoic acid | 130-85-8 |
| 2,4-Dimethylphenol | 105-67-9 |
| 3,5-Dihydroxyacetophenone | 51863-60-6 |
| Eugenol | 97-53-0 |
| n-Butyric Acid | 107-92-6 |
| Hydroquinone | 123-31-9 |
| Propionic Acid | 79-09-4 |
| meta-Phenylenediamine | 108-45-2 |
| Oxalic Acid | 144-62-7 |
| n-Hexanoic Acid | 142-62-1 |
| 2-Furancarboxylic Acid | 88-14-2 |
| 4"-N itroacetanilide | 104-04-1 |
| D-(−)-Tartaric Acid | 147-71-7 |
| p-Acetamidobenzoic Acid | 556-08-1 |
| Galactaric acid | 526-99-8 |
| D-glucuronate | 1700908 |
| Lactobionic acid | 96-82-2 |
| p-Formylacetanilide | 122-85-0 |
| 2-Mercaptobenzoic acid | 147-93-3 |
| Propanoic acid, 2-hydroxy-, calcium salt (2:1), (S)- | 28305-25-1 |
| D(+)-10-Camphorsulfonic acid | 3144-16-9 |
| 3-Cyclopentylpropionic acid | 140-77-2 |
| 1R-(−)-Camphorsulfonic acid | 35963-20-3 |
| DL-Lysine | 70-54-2 |
| Cinnamic acid | 621-82-9 |
| Triethanolamine | 102-71-6 |
| Acetic Acid | 64-19-7 |
| Dichioroacetic Acid | 79-43-6 |
| Diethylamine | 109-89-7 |
| Diethylaminoethanol | 100-37-8 |
| N-(2-Hydroxyethyl)Morpholine | 622-40-2 |
| Octanoic Acid | 124-07-2 |
| isobutyric acid | 79-31-2 |
| Anisic Acid | 100-09-4 |
| Betaine | 107-43-7 |
| Enanthoic Acid | 111-14-8 |
| Hippuric Acid | 495-69-2 |
| Tiglic Acid | 80-59-1 |
| Cyclohexanecarboxylic acid | 98-89-5 |
| m-Methoxybenzoic acid | 586-38-9 |
| D-(+)-Camphoric acid | 124-83-4 |
| N-(2-Hydroxyethyl)pyrrolidine | 2955-88-6 |
| Sodium Metabisulfite | 7681-57-4 |
| sodium hydrogen phosphate | 7558-79-4 |
| Sodium Phosphate Monobasic | 7558-80-7 |
| Sodium thiosulfate | 7772-98-71 |
| Orthoboric acid | 10043-35-3 |
| Diethanolamine | 111-42-2 |
| Benzaldehyde | 100-52-7 |
| Sorbic acid | 110-44-1 |
| L-(+)-Tartaric Acid | 87-69-4 |
| D-mannitol | 69-65-8 |
| Butyl paraben | 94-26-8 |
| Thymol | 89-83-8 |
| Methyl salicylate | 119-36-8 |
| Citric acid | 77-92-9 |
| Creatinine | 60-27-5 |
| Vitamin C | 50-81-7 |
| Benzoic Acid | 65-85-0 |
| Methyl 4-hydroxybenzoate | 99-76-3 |
| m-Cresol | 108-39-4 |
| p-Cresol | 106-44-5 |
| Aspirin | 50-78-2 |
| Phenol | 108-95-2 |
| Sucrose | 57-50-1 |
| Potassium citrate, monohydrate | 1534146 |
| Sodium acetate | 127-09-3 |
| Lactic acid | 50-21-5 |
| Propionic acid, sodium salt | 65-85 |
| Benzyl alcohol | 100-51-6 |
| Phenethyl alcohol | 60-12-8 |
| Cholesterol | 57-88-5 |
| D-Glucose | 50-99-7 |
| Sorbitol | 50-70-4 |
| Aspartame | 22839-47-0 |
| Saccharin | 81-07-2 |
| 2,6-Di-tert-Butyl-p-Cresol | 128-37-0 |
| 4-Chloro-3-methylphenol | 59-50-7 |
| glycerin | 56-81-5 |
| Propyl paraben | 94-13-3 |
| fumaric acid | 110-17-8 |
| dabco | 280-57-9 |

TABLE 10-continued

| Name | CAS # |
|---|---|
| p-Phenylenediamine | 106-50-3 |
| Anethole | 4180-23-8 |
| propyl gallate | 121-79-9 |
| L-monosodium glutamate | 142-47-2 |
| Butylated hydroxyanisole | 25013-16-5 |
| Cyclohexanol, 5-methyl-2-(1-methylethyl)-, (1alpha,2beta,5alpha)- | 89-78-1 |
| alpha-Thioglycerol | 96-27-5 |
| Sodium dehydroacetate | 4418-26-2 |
| Ethyl 4-hydroxybenzoate | 120-47-8 |
| Ethyl Vanillin | 121-32-4 |
| Triacetin | 102-76-1 |
| Potassium sorbate | 590-00-1 |
| Triethyl citrate | 77-93-0 |
| (S)-(+)-Arginine | 74-79-3 |
| Glycine | 56-40-6 |
| (S)-(−)-Histidine | 71-00-1 |
| (S)-(+)-Lysine | 56-87-1 |
| Quinone | 106-51-4 |
| Naphthalene, 2-ethoxy- | 93-18-5 |
| Methanesulfonic Acid | 75-75-2 |
| DL-Tartaric Acid | 133-37-9 |
| Cyclamic acid | 100-88-9 |
| (S)-(−)-Phenylalanine | 63-91-2 |
| (S)-(−)-Tyrosine | 60-18-4 |
| Carvone | 99-49-0 |
| Ethyl butyrate | 105-54-4 |
| 6-Methyl-5-hepten-2-one | 110-93-0 |
| Ethyl acetoacetate | 141-97-9 |
| Methyl benzoate | 93-58-3 |
| Phenylacetic Acid | 103-82-2 |
| Adipic acid | 124-04-9 |
| Ethyl benzoate | 93-89-0 |
| Benzyl benzoate | 120-51-4 |
| Pyruvic acid | 127-17-3 |
| Succinic acid | 110-15-6 |
| Indole | 120-72-9 |
| Methyl anthranilate | 134-20-3 |
| Diethyl malonate | 105-53-3 |
| Niacin | 59-67-6 |
| Meso-inositol | 87-89-8 |
| 4-Aminobenzoic acid | 150-13-0 |
| Anisole | 100-66-3 |
| Urea | 57-13-6 |
| Pyrrolidine | 123-75-1 |
| Cyclopentanone | 120-92-3 |
| Acetic anhydride | 108-24-7 |
| Benzophenone | 119-61-9 |
| D-(−)-Fructose | 57-48-7 |
| D-(+)-Xylose | 58-86-6 |
| o-Methoxybenzoic Acid | 579-75-9 |
| linalool | 78-70-6 |
| ethyl isovalerate | 108-64-5 |
| 1,1'-Azobisformamide | 123-77-3 |
| 6-Methylcoumarin | 92-48-8 |
| acetoin | 513-86-0 |
| alpha-Phellandrene | 99-83-2 |
| Cymene | 99-87-6 |
| Dimethyl Succinate | 106-65-0 |
| p-Anisaidehyde | 123-11-5 |
| Phenyl ether | 101-84-8 |
| Tetrahydro-2-furanmethanol | 97-99-4 |
| Valeric Acid | 109-52-4 |
| 3,4-xylenol | 95-65-8 |
| 1,1-diethoxyethane | 105-57-7 |
| ethyl butyraldehyde | 97-96-1 |
| Ethyl crotonate | 623-70-1 |
| ethyl isobutyrate | 97-62-1 |
| methyl isovalerate | 556-24-1 |
| methyl propionate | 554-12-1 |
| methyl valeraldehyde | 123-15-9 |
| 4-(2,6,6-Trimethyl-2 cyclohexen-1-yl)-3-buten-2-one | 127-41-3 |
| 4-(2,6,6-trimethyl-1 cyclohexen-1-yl)-3-buten-2-one | 14901-07-6 |
| Maleic acid | 110-16-7 |
| 3-Methylbutanoic acid | 503-74-2 |
| L-Glutamic Acid | 56-86-0 |
| D-limonene | 5989-27-5 |
| 1-Phenyl-1-propanol | 93-54-9 |
| 2'-Hydroxyacetophenone | 118-93-4 |
| 2,4-Dihydroxybenzoic Acid | 89-86-1 |
| 2-Phenyl-1-propanol | 1123-85-9 |
| 3-Phenylpropionic Acid | 501-52-0 |
| 4-Ethoxyphenol | 622-62-8 |
| Alpha-Terpineol | 98-55-5 |
| Benzaldehyde Dimethylacetal | 1125-88-8 |
| Benzyl Ether | 103-50-4 |
| Benzyl Formate | 104-57-4 |
| Benzyl Salicylate | 118-58-1 |
| Cinnamyl Alcohol | 104-54-1 |
| D-(+)-Glucono-1,5-lactone | 4253-68-3 |
| D-Isoascorbic Acid | 89-65-6 |
| 2,3-Naphthalenediol | 92-44-4 |
| Diethyl Succinate | 123-25-1 |
| Ethyl 2-Aminobenzoate | 87-25-2 |
| Ethyl Cinnamate | 103-36-6 |
| Ethyl Phenylacetate | 101-97-3 |
| Ethyl Salicylate | 118-61-6 |
| gamma-Valerolactone | 108-29-2 |
| Hydroquinone Dimethyl Ether | 150-78-7 |
| Isocaproic Acid | 646-07-1 |
| Isoeugenol | 97-54-1 |
| Isopropyl Benzoate | 939-48-0 |
| L-(+)-Isoleucine | 73-32-5 |
| L-Malic acid | 97-67-6 |
| L-2-Aminopropionic Acid | 56-41-7 |
| L-Carnitine | 541-15-1 |
| L-Glutamine | 56-85-9 |
| L-Hydroxyproline | 51-35-4 |
| L-Proline | 147-85-3 |
| L-Serine | 56-45-1 |
| L-Threonine | 72-19-5 |
| L-Valine | 72-18-4 |
| Phenoxyacetic Acid | 122-59-8 |
| Veratrole | 91-16-7 |
| 2-Ethylbutyric acid | 88-09-5 |
| 2-Methylpyrazine | 109-08-0 |
| o-methoxybenzaldehyde | 135-02-4 |
| L-Leucine | 61-90-5 |
| L-Asparagine | 70-47-3 |
| propiophenone | 93-55-0 |
| 5-isopropyl-2-methyl-phenol | 499-75-2 |
| Xylitol | 87-99-0 |
| ethyl 4-oxopentanoate | 539-88-8 |
| methyl cinnamate | 103-26-4 |
| cumic alcohol | 536-60-7 |
| methyl 2-naphthyl ketone | 93-08-3 |
| 1-methyl-4-(1-methylethyl) 1, 4-Cyclohexadiene en-ethylene diamine | 99-85-4 |
| Caffeine | 58-08-2 |
| 5-methylfurfural | 620-02-0 |
| furfuryl acetate | 623-17-6 |
| terpinen-4-ol | 10482-56-1 |
| phenylethanal | 122-78-1 |
| 4'-Methoxyacetophenone | 100-06-1 |
| D-Fenchone | 4695-62-9 |
| 1-Methoxy-4-methylbenzene | 104-93-8 |
| o-methylanisole | 578-58-5 |
| Acetylacetaldehyde dimethyl acetal | 5436-21-5 |
| p-methylacetophenone | 122-00-9 |
| Methyl phenylacetate | 101-41-7 |
| 4-Ethoxybenzaldehyde | 10031-82-0 |
| p-tolyl acetate | 140-39-6 |
| 2,6-Dimethoxyphenol | 91-10-1 |
| Methyl 2-methoxybenzoate | 606-45-1 |
| alpha-methylcinnamaldehyde | 101-39-3 |
| 2-methoxycinnamaldehyde | 60125-24-8 |
| Potassium bicarbonate | 298-14-6 |
| piperonyl acetate | 326-61-4 |
| 2,3-hexanedione | 3848-24-6 |
| furfural acetone | 623-15-4 |
| trans beta-(2-furyl)acrolein | 623-30-3 |
| carveol | 99-48-9 |
| Methyl nicotinate | 93-60-7 |
| Ethyl benzoylacetate | 94-02-0 |
| Methyl 4-methoxybenzoate | 121-98-2 |
| Levulinic acid | 123-76-2 |

TABLE 10-continued

| Name | CAS # |
| --- | --- |
| m-Dimethoxybenzene | 151-10-0 |
| 2-acetylpyridine | 1122-62-9 |
| tetramethyl-pyrazine | 1124-11-4 |
| 2,3-dimethyl-pyrazine | 5910-89-4 |
| trimethyl-pyrazine | 14667-55-1 |
| 2-ethyl-3-methyl-pyrazine | 15707-23-0 |
| 5-Methyl-3H-furan-2-one | 591-12-8 |
| 2-Methoxy-4-methylphenol | 93-51-6 |
| piperazine | 110-85-0 |
| 2-Methoxy-4-propylphenol | 2785-87-7 |
| Naphthalene, 2-(2 methylpropoxy)- | 2173-57-1 |
| 2-Acetyl-1-methylpyrrole | 932-16-1 |
| 3,3-Dimethylacrylic acid | 541-47-9 |
| Ethyl sorbate | 2396-84-1 |
| 4-(4-Hydroxyphenyl)-2-butanone | 5471-51-2 |
| 4-Methoxyphenylacetone | 122-84-9 |
| (−)-Myrtenal | 564-94-3 |
| 3- Phenylpropionaldehyde | 104-53-0 |
| 1-Phenylethyl propionate | 120-45-6 |
| 2-Methyltetrahydrofuran-3-one | 3188-00-9 |
| Cinnamyl acetate | 103-54-8 |
| Styrallyl acetate | 93-92-5 |
| Ethyl 4-methoxybenzoate | 94-30-4 |
| Benzyl propionate | 122-63-4 |
| Phenylpyruvate | 156-06-9 |
| furaneol | 3658-77-3 |
| methyl 2-methylbutanoate | 868-57-5 |
| Benzeneacetaldehyde, alpha methyl- | 93-53-8 |
| Dimethyl anthranilate | 85-91-6 |
| 1,1-Dimethoxy-2-phenylpropane | 90-87-9 |
| 4-hexanolide | 695-06-7 |
| Dimethylbenzylcarbinyl acetate | 151-05-3 |
| Benzyl isobutyrate | 103-28-6 |
| Acetyl isoeugenol | 93-29-8 |
| 2-Acetyl-5-methyl furan | 1193-79-9 |
| Alpha-methyl-pisopropylphenylpropanaldehyde | 103-95-7 |
| Benzylcarbinyl formate | 104-62-1 |
| p-Cresyl alpha-toluate | 101-94-0 |
| Potassium bisulfate | 7646-93-7 |
| Potassium carbonate | 584-08-7 |
| Potassium chloride | 7447-40-7 |
| Potassium hydroxide | 1310-58-3 |
| Ethyl tiglate | 5837-78-5 |
| Nerol oxide | 1786-08-9 |
| DL-Tetrahydrofurfuryl propionate | 637-65-0 |
| Benzaldehyde propylene glycol acetal | 2568-25-4 |
| 2-Methyl-3-(2-furyl) acrolein | 874-66-8 |
| vanillin | 121-33-5 |
| Cholic acid | 81-25-4 |
| R-Carvone | 6485-40-1 |
| Potassium nitrate | 7757-79-1 |
| Potassium permanganate | 7722-64-7 |
| Potassium persulfate | 7727-21-1 |
| Potassium phosphate, dibasic | 2139900 |
| Potassium Phosphate Monobasic | 7778-77-0 |
| Potassium sulfate | 7778-80-5 |
| Sodium bicarbonate | 144-55-8 |
| Sodium bisulfite | 7631-90-5 |
| Sodium carbonate | 497-19-8 |
| Sodium chloride | 7647-14-5 |
| Sodium dithionite | 7775-14-6 |
| Sodium hydroxide | 1310-73-2 |
| Sodium nitrite | 7632-00-0 |
| Sodium Pyrophosphate | 7722-88-5 |
| Sodium sulfate | 7757-82-6 |
| Sodium sulfite | 7757-83-7 |
| Sodium thiocyanate | 540-72-7 |
| Calcium Carbonate | 471-34-1 |
| Calcium chloride | 10043-52-4 |
| Calcium gluconate | 299-28-5 |
| Calcium hydroxide | 1305-62-0 |
| Calcium phosphate, dibasic | 7757-93-9 |
| Calcium sulfate | 7778-18-9 |
| N-Methyl-D-glucamine | 6284-40-8 |
| Calcium oxide | 1305-78-8 |
| Calcium Phosphate Monobasic | 7758-23-8 |
| Magnesium chloride hexahydrate | 7791-18-6 |
| Magnesium sulfate | 7487-88-9 |
| Magnesium Sulfate Heptahydrate | 10034-99-8 |
| Aluminum chloride hexahydrate | 7784-13-6 |
| aluminum nitrate nonahydrate | 7784-27-2 |
| Aluminum potassium sulfate, dodecahydrate | 7784-24-9 |
| Aluminum sulfate, octadecahydrate | 7784-31-8 |
| (S)-(−)-Cysteine | 52-90-4 |
| p-Toluenesulfonic Acid | 104-15-4 |
| Potassium bitartrate | 868-14-4 |
| DL-aspartic acid | 617-45-8 |
| p-Dimethylaminobenzaldehyde | 100-10-7 |
| Sodium salicylate | 54-21-7 |
| Benzoin | 119-53-9 |
| Sodium dodecyl sulfate | 151-21-3 |
| L-Menthol | 2216-51-5 |
| Tiron | 149-45-1 |
| Riboflavin | 83-88-5 |
| Sodium Acetate Trihydrate | 6131-90-4 |
| Disodium Succinate Hexahydrate | 6106-21-4 |
| Disodium ethylenediaminetetraacetatedihydrate | 6381-92-6 |
| sodium citrate, dihydrate | 1545801 |
| Sodium potassium tartrate, tetrahydrate | 6381-59-5 |
| L-(+)-Arginine monohydrochloride | 1119-34-2 |
| Ethylenediamine dihydrochloride | 333-18-6 |
| Sodium formate | 141-53-7 |
| Sodium acetate | 127-09-3 |
| Potassium acetate | 127-08-2 |
| Ammonium citrate | 3012-65-5 |
| Ammonium bicarbonate | 1066-33-7 |
| Ammonium chloride | 12125-02-9 |
| Ammonium nitrate | 6484-52-2 |
| Ammonium persulfate | 7727-54-0 |
| Ammonium sulfate | 7783-20-2 |
| Zinc chloride | 7646-85-7 |
| Sulfuric acid, zinc salt(1:1), heptahydrate | 7446-20-0 |
| Sodium Tripolyphosphate | 7758-29-4 |
| ammonium benzoate | 1863-63-4 |
| ammonium bisulfite | 10192-30-0 |
| 1,5-Naphthalenedisulfonic Acid Disodium Salt | 1655-29-4 |
| 4-Hydroxybenzoic Acid | 99-96-7 |
| Diphenylacetic Acid | 117-34-0 |
| Glutaric Acid | 110-94-1 |
| L-(−)-Fucose | 2438-80-4 |
| L-Cysteine Hydrochloride | 52-89-1 |
| L-Histidine Hydrochloride Monohydrate | 1880304 |
| o-Toluic Acid | 118-90-1 |
| Pivalic Acid | 75-98-9 |
| Pyruvic Acid Sodium Salt | 113-24-6 |
| Potassium bromide | 2139626 |
| Sodium Dithionate Dihydrate | 7631-94-9 |
| Sodium Malonate | 141-95-7 |
| Trisodium Citrate | 68-04-2 |
| Potassium Sodium Tartrate | 304-59-6 |
| Potassium Citrate | 866-84-2 |
| D-Maltose Monohydrate | 6363-53-7 |
| Cyclohexaamylose | 10016-20-3 |
| Dodecyl sulfate, lithium salt | 2044-56-6 |
| Manganese chloride | 2145076 |
| methyl-urea | 598-50-5 |
| beta-Cyclodextrin | 7585-39-9 |
| Triphosphoric acid, pentapotassium salt | 13845-36-8 |
| Glycine ethyl ester hydrochloride | 623-33-6 |
| L-Histidine methyl ester dihydrochloride | 7389-87-9 |
| L-Leucine methyl ester hydrochloride | 7517-19-3 |
| D-Lysine hydrochloride | 7274-88-6 |
| 2-Naphthalenesulfonic acid sodium salt | 532-02-5 |
| calcium nitrate tetrahydrate | 13477-34-4 |
| Vitamin B1 | 59-43-8 |
| Zinc Acetate Dihydrate | 5970-45-6 |
| Potassium fluoride | 7789-23-3 |
| Potassium iodate | 2139718 |
| Potassium iodide | 7681-11-0 |
| Potassium thiocyanate | 333-20-0 |
| Sodium bromide | 7647-15-6 |
| Sodium fluoride | 7681-49-4 |
| Sodium iodide | 7681-82-5 |
| Sodium nitrate | 7631-99-4 |
| Calcium acetate | 5743-26-0 |
| Trichloroacetic acid | 76-03-9 |

TABLE 10-continued

| Name | CAS # |
| --- | --- |
| Ammonium acetate | 631-61-8 |
| Ammoniu rii fluoride | 12125-01-8 |
| DL-malic acid | 617-48-1 |
| t-Butyl Alcohol | 75-65-0 |
| beta-Alanine | 107-95-9 |
| (S)-(−)-Tryptophan | 73-22-3 |
| Malonic acid | 141-82-2 |
| Phenethylamine | 64-04-0 |
| Salicylylaldehyde | 90-02-8 |
| Sodium benzoate | 532-32-1 |
| Mandelic acid | 90-64-2 |
| Calcium pantothenate | 137-08-6 |
| Chloroacetic Acid | 79-11-8 |
| Ethanol Amine | 141-43-5 |
| Salicylic acid | 69-72-7 |
| Saccharin sodium | 128-44-9 |
| Thiamine hydrochloride | 67-03-8 |
| 2,2'-Oxybisethanol | 111-46-6 |
| Resorcinol | 108-46-3 |
| 2-Amino-2-(hydroxymethyl)-1,3 propanediol | 77-86-1 |
| 2,5-Dimethylphenol | 95-87-4 |
| Ammonium Phosphate Monobasic | 7722-76-1 |
| 1,3-Butanediol | 107-88-0 |
| Glycolic Acid | 79-14-1 |
| Sodium Gluconate | 527-07-1 |
| Terephthalic Acid | 100-21-0 |
| L-Ascorbic Acid Sodium Salt | 134-03-2 |
| 3-Acetyl-6-methyl-2,4 pyrandione | 520-45-6 |
| Calcium Acetate | 62-54-4 |
| Nicotinamide | 98-92-0 |
| 1-Hydroxy-2-naphthoic Acid | 86-48-6 |
| 2-Isopropylphenol | 88-69-7 |
| 4-Aminosalicylic Acid | 65-49-6 |
| Calcium Glycerophosphate | 27214-00-2 |
| Erythorbic Acid Sodium Salt | 7378-23-6 |
| Gluconic Acid Potassium Salt | 299-27-4 |
| Orotic Acid | 65-86-1 |
| p-Anise Alcohol | 105-13-5 |
| Potassium Benzoate | 582-25-2 |
| Taurine | 107-35-7 |
| Thiamine Nitrate | 532-43-4 |
| 3,3,5-Trimethyl-1-cyclohexanol | 116-02-9 |
| tert-Butylhydroquinone | 1948-33-0 |
| Sulfosalicylic acid | 97-05-2 |
| Gallic acid | 149-91-7 |
| L-borneol | 464-45-9 |
| Isoborneol | 124-76-5 |
| 2,5-Dihydroxybenzoic acid, Gentisic acid | 490-79-9 |
| 5-hydroxy-6-methyl-3,4-pyridinedimethanol | 65-23-6 |
| Naphthalene-2-sulfonic acid | 120-18-3 |
| Ethanesulfonic acid, 2 hydroxy-, monosodium salt | 1562-00-1 |
| Pamoic acid | 130-85-8 |
| 2,4-Dimethylphenol | 105-67-9 |
| 3,5-Dihydroxyacetophenone | 51863-60-6 |
| Eugenol | 97-53-0 |
| n-Butyric Acid | 107-92-6 |
| Hydroquinone | 123-31-9 |
| Propionic Acid | 79-09-4 |
| meta-Phenylenediamine | 108-45-2 |
| Oxalic Acid | 144-62-7 |
| n-Hexanoic Acid | 142-62-1 |
| 2-Furancarboxylic Acid | 88-14-2 |
| 4'-Nitroacetanilide | 104-04-1 |
| D-(−)-Tartaric Acid | 147-71-7 |
| p-Acetamidobenzoic Acid | 556-08-1 |
| Galactaric acid | 526-99-8 |
| D-glucuronate | 1700908 |
| Lactobionic acid | 96-82-2 |
| p-Formylacetanilide | 122-85-0 |
| 2-Mercaptobenzoic acid | 147-93-3 |
| Propanoic acid, 2-hydroxy-, calcium salt (2:1), (S)- | 28305-25-1 |
| D(+)-10-Camphorsulfonic acid | 3144-16-9 |
| 3-Cyclopentylpropionic acid | 140-77-2 |
| 1R-(−)-Camphorsulfonic acid | 35963-20-3 |
| DL-Lysine | 70-54-2 |
| Cinnamic acid | 621-82-9 |
| Triethanolamine | 102-71-6 |
| Acetic Acid | 64-19-7 |
| Dichloroacetic Acid | 79-43-6 |
| Diethylamine | 109-89-7 |
| Diethylaminoethanol | 100-37-8 |
| N-(2-Hydroxyethyl)Morpholine | 622-40-2 |
| Octanoic Acid | 124-07-2 |
| isobutyric acid | 79-31-2 |
| Anisic Acid | 100-09-4 |
| Betaine | 107-43-7 |
| Enanthoic Acid | 111-14-8 |
| Hippuric Acid | 495-69-2 |
| Tiglic Acid | 80-59-1 |
| Cyclohexanecarboxylic acid | 98-89-5 |
| m-Methoxybenzoic acid | 586-38-9 |
| D-(+)-Camphoric acid | 124-83-4 |
| N-(2-Hydroxyethyl)pyrrolidine | 2955-88-6 |

What is claimed is:

1. A cocrystal of fluoxetine hydrochloride and benzoic acid, wherein the cocrystal is prepared by sonicating a solution of fluoxetine hydrochloride and benzoic acid in acetonitrile.

2. A method of making a cocrystal of fluoxetine hydrochloride and benzoic acid, comprising:
sonicating a solution of fluoxetine hydrochloride and benzoic acid in acetonitrile.

3. The method of claim 2, wherein the fluoxetine hydrochloride and benzoic acid are in about a 1:1 molar ratio.

4. The method of claim 2, wherein the solution contains about 35 mg/mL to about 200 mg/mL fluoxetine hydrochloride and benzoic acid.

5. The method of claim 2, wherein the solution contains about 35 mg/mL to about 100 mg/mL fluoxetine hydrochloride and benzoic acid.

* * * * *